United States Patent
Schnee et al.

(10) Patent No.: US 12,083,190 B2
(45) Date of Patent: *Sep. 10, 2024

(54) RABIES VACCINE

(71) Applicant: CureVac SE, Tübingen (DE)

(72) Inventors: Margit Schnee, Constance (DE);
Thomas Kramps, Tübingen (DE);
Lothar Stitz, Rottenburg (DE);
Benjamin Petsch, Tübingen (DE)

(73) Assignee: CureVac SE, Tübingen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/746,844

(22) Filed: May 17, 2022

(65) Prior Publication Data

US 2022/0288239 A1    Sep. 15, 2022

Related U.S. Application Data

(60) Division of application No. 16/865,107, filed on May 1, 2020, now Pat. No. 11,369,694, which is a division of application No. 15/048,356, filed on Feb. 19, 2016, now Pat. No. 10,682,426, which is a continuation of application No. PCT/EP2014/002298, filed on Aug. 21, 2014.

(30) Foreign Application Priority Data

Aug. 21, 2013  (WO) ................. PCT/EP2013/002517

(51) Int. Cl.
| | | |
|---|---|---|
| *A61K 39/12* | (2006.01) | |
| *A61K 9/00* | (2006.01) | |
| *A61K 39/205* | (2006.01) | |
| *A61K 39/42* | (2006.01) | |
| *A61K 48/00* | (2006.01) | |
| *C07K 14/005* | (2006.01) | |
| *C07K 16/10* | (2006.01) | |
| *C12N 7/00* | (2006.01) | |
| *A61K 39/00* | (2006.01) | |

(52) U.S. Cl.
CPC ........ *A61K 48/0075* (2013.01); *A61K 9/0021* (2013.01); *A61K 39/12* (2013.01); *A61K 39/205* (2013.01); *A61K 39/42* (2013.01); *C07K 14/005* (2013.01); *C07K 16/10* (2013.01); *C12N 7/00* (2013.01); *A61K 2039/53* (2013.01); *A61K 2039/54* (2013.01); *A61K 2039/545* (2013.01); *A61K 2039/552* (2013.01); *C12N 2760/20134* (2013.01)

(58) Field of Classification Search
None
See application file for complete search history.

(56) References Cited

U.S. PATENT DOCUMENTS

| | | |
|---|---|---|
| 8,217,016 B2 | 7/2012 | Hoerr et al. |
| 8,383,340 B2 | 2/2013 | Ketterer et al. |
| 8,703,906 B2 | 4/2014 | Baumhof et al. |
| 8,968,746 B2 | 3/2015 | Baumhof et al. |
| 9,155,788 B2 | 10/2015 | Hoerr et al. |
| 9,226,959 B2 | 1/2016 | Kramps et al. |
| 9,234,013 B2 | 1/2016 | Thess et al. |
| 9,314,535 B2 | 4/2016 | Baumhof et al. |
| 9,352,028 B2 | 5/2016 | Barner et al. |
| 9,402,887 B2 | 8/2016 | Probst et al. |
| 9,421,255 B2 | 8/2016 | Baumhof et al. |
| 9,433,669 B2 | 9/2016 | Hoerr et al. |
| 9,433,670 B2 | 9/2016 | Hoerr et al. |
| 9,439,956 B2 | 9/2016 | Hoerr et al. |
| 9,447,431 B2 | 9/2016 | Thess et al. |
| 9,463,228 B2 | 10/2016 | Hoerr et al. |
| 9,572,874 B2 | 2/2017 | Fotin-Mleczek et al. |
| 9,616,084 B2 | 4/2017 | Mutzke |
| 9,623,095 B2 | 4/2017 | Kallen et al. |
| 9,655,955 B2 | 5/2017 | Hoerr et al. |
| 9,669,089 B2 | 6/2017 | Thess et al. |
| 9,683,233 B2 | 6/2017 | Thess |
| 9,688,729 B2 | 6/2017 | Kramps et al. |

(Continued)

FOREIGN PATENT DOCUMENTS

| | | |
|---|---|---|
| WO | WO 2002/085434 | 10/2002 |
| WO | WO 2003/059381 | 7/2003 |

(Continued)

OTHER PUBLICATIONS

US 11,458,100 B2, 10/2022, Ketterer et al. (withdrawn)

(Continued)

*Primary Examiner* — Benjamin P Blumel
(74) *Attorney, Agent, or Firm* — Parker Highlander PLLC

(57) ABSTRACT

The present invention relates to an mRNA sequence, comprising a coding region, encoding at least one antigenic peptide or protein of Rabies virus or a fragment, variant or derivative thereof. Additionally the present invention relates to a composition comprising a plurality of mRNA sequences comprising a coding region, encoding at least one antigenic peptide or protein of Rabies virus or a fragment, variant or derivative thereof.

Furthermore it also discloses the use of the mRNA sequence or the composition comprising a plurality of mRNA sequences for the preparation of a pharmaceutical composition, especially a vaccine, e.g. for use in the prophylaxis or treatment of Rabies virus infections. The present invention further describes a method of treatment or prophylaxis of rabies using the mRNA sequence.

18 Claims, 18 Drawing Sheets

Specification includes a Sequence Listing.

(56) References Cited

U.S. PATENT DOCUMENTS

| | | |
|---|---|---|
| 9,737,595 B2 | 8/2017 | Lorenz et al. |
| 9,839,697 B2 | 12/2017 | Thess et al. |
| 9,890,391 B2 | 2/2018 | Thess et al. |
| 9,907,862 B2 | 3/2018 | Baumhof et al. |
| 9,974,845 B2 | 5/2018 | Fotin-Mleczek et al. |
| 10,010,592 B2 | 7/2018 | Thess et al. |
| 10,017,826 B2 | 7/2018 | von der Mülbe et al. |
| 10,047,375 B2 | 8/2018 | Thess |
| 10,080,809 B2 | 9/2018 | Thess |
| 10,111,967 B2 | 10/2018 | Fotin-Mleczek et al. |
| 10,111,968 B2 | 10/2018 | Thess et al. |
| 10,117,920 B2 | 11/2018 | Fotin-Mleczek et al. |
| 10,150,797 B2 | 12/2018 | Kramps et al. |
| 10,166,283 B2 | 1/2019 | Thess et al. |
| 10,172,935 B2 | 1/2019 | Kallen et al. |
| 10,188,748 B2 | 1/2019 | von der Mülbe et al. |
| 10,232,024 B2 | 3/2019 | Thess et al. |
| 10,293,058 B2 | 5/2019 | Fotin-Mleczek et al. |
| 10,293,060 B2 | 5/2019 | Baumhof |
| 10,307,472 B2 | 6/2019 | Fotin-Mleczek et al. |
| 10,369,216 B2 | 8/2019 | Fotin-Mleczek et al. |
| 10,434,154 B2 | 10/2019 | Probst et al. |
| 10,434,158 B2 | 10/2019 | Fotin-Mleczek et al. |
| 10,441,653 B2 | 10/2019 | Hoerr et al. |
| 10,501,768 B2 | 12/2019 | Eber et al. |
| 10,517,827 B2 | 12/2019 | Eber et al. |
| 10,568,958 B2 | 2/2020 | Baumhof et al. |
| 10,568,972 B2 | 2/2020 | von der Mülbe et al. |
| 10,588,959 B2 | 3/2020 | Kallen et al. |
| 10,596,252 B2 | 3/2020 | Kallen et al. |
| 10,610,605 B2 | 4/2020 | Thess et al. |
| 10,648,017 B2 | 5/2020 | Wochner |
| 10,653,768 B2 | 5/2020 | Mutzke et al. |
| 10,653,799 B2 | 5/2020 | Thess et al. |
| 10,682,406 B2 | 6/2020 | Thess et al. |
| 10,682,426 B2 * | 6/2020 | Schnee ............... A61K 39/205 |
| 10,711,315 B2 | 7/2020 | von der Mülbe et al. |
| 10,729,654 B2 | 8/2020 | Eber et al. |
| 10,729,761 B2 | 8/2020 | Kallen et al. |
| 10,738,306 B2 | 8/2020 | Thess |
| 10,751,424 B2 | 8/2020 | Baumhof et al. |
| 10,760,070 B2 | 9/2020 | Funkner et al. |
| 10,780,054 B2 | 9/2020 | Ketterer et al. |
| 10,799,577 B2 | 10/2020 | Thess et al. |
| 10,799,602 B2 | 10/2020 | Baumhof |
| 10,837,039 B2 | 11/2020 | Wochner et al. |
| 10,869,935 B2 | 12/2020 | Fotin-Mleczek et al. |
| 10,898,584 B2 | 1/2021 | Schlake et al. |
| 10,898,589 B2 | 1/2021 | Thess et al. |
| 10,912,826 B2 | 2/2021 | Thess et al. |
| 10,918,740 B2 | 2/2021 | Fotin-Mleczek et al. |
| 10,988,754 B2 | 4/2021 | Fotin-Mleczek et al. |
| 11,034,729 B2 | 6/2021 | Kramps et al. |
| 11,078,247 B2 | 8/2021 | Fotin-Mleczek et al. |
| 11,110,156 B2 | 9/2021 | Thess et al. |
| 11,110,157 B2 | 9/2021 | Fotin-Mleczek et al. |
| 11,110,166 B2 | 9/2021 | Fotin-Mleczek et al. |
| 11,135,312 B2 | 10/2021 | von der Mülbe et al. |
| 11,141,474 B2 | 10/2021 | Rauch et al. |
| 11,141,476 B2 | 10/2021 | Rauch |
| 11,149,278 B2 | 10/2021 | Thess et al. |
| 11,179,337 B2 | 11/2021 | Eber et al. |
| 11,225,682 B2 | 1/2022 | Reichert et al. |
| 11,241,493 B2 | 2/2022 | Rauch et al. |
| 11,248,223 B2 | 2/2022 | Yazdan Panah et al. |
| 11,254,951 B2 | 2/2022 | Thess |
| 11,266,735 B2 | 3/2022 | Kallen et al. |
| 11,268,157 B2 | 3/2022 | von der Mülbe et al. |
| 11,274,293 B2 | 3/2022 | Funkner et al. |
| 11,279,923 B2 | 3/2022 | Funkner et al. |
| 11,286,492 B2 | 3/2022 | Thess et al. |
| 11,345,920 B2 | 5/2022 | Thess et al. |
| 11,369,691 B2 | 6/2022 | von der Mülbe et al. |
| 11,369,694 B2 | 6/2022 | Schnee et al. |
| 11,384,375 B2 | 7/2022 | Roos et al. |
| 11,413,346 B2 | 8/2022 | Rauch et al. |
| 11,421,038 B2 | 8/2022 | Hoerr et al. |
| 11,433,027 B2 | 9/2022 | Eber et al. |
| 11,446,250 B2 | 9/2022 | Ketterer et al. |
| 11,458,193 B2 | 10/2022 | Lorenz et al. |
| 11,458,195 B2 | 10/2022 | Fotin-Mleczek et al. |
| 11,464,836 B2 | 10/2022 | Horscroft et al. |
| 11,464,847 B2 | 10/2022 | Jasny et al. |
| 2005/0032730 A1 | 2/2005 | Von der Mulbe et al. |
| 2005/0059624 A1 | 3/2005 | Hoerr et al. |
| 2005/0250723 A1 | 11/2005 | Hoerr et al. |
| 2006/0188490 A1 | 8/2006 | Hoerr et al. |
| 2007/0280929 A1 | 12/2007 | Hoerr et al. |
| 2008/0025944 A1 | 1/2008 | Hoerr et al. |
| 2008/0171711 A1 | 7/2008 | Hoerr et al. |
| 2008/0267873 A1 | 10/2008 | Hoerr et al. |
| 2009/0324584 A1 | 12/2009 | Hoerr et al. |
| 2010/0047261 A1 | 2/2010 | Hoerr et al. |
| 2010/0048883 A1 | 2/2010 | Ketterer et al. |
| 2010/0189729 A1 | 7/2010 | Hoerr et al. |
| 2010/0203076 A1 | 8/2010 | Fotin-Mleczek et al. |
| 2010/0291156 A1 | 11/2010 | Barner et al. |
| 2010/0305196 A1 | 12/2010 | Probst et al. |
| 2011/0053829 A1 | 3/2011 | Baumhof et al. |
| 2011/0250225 A1 | 10/2011 | Fotin-Mleczek et al. |
| 2012/0021043 A1 | 1/2012 | Kramps et al. |
| 2012/0258046 A1 | 10/2012 | Mutzke |
| 2013/0129754 A1 | 5/2013 | Thess et al. |
| 2013/0142818 A1 | 6/2013 | Baumhof et al. |
| 2013/0195867 A1 | 8/2013 | Hoerr et al. |
| 2013/0259879 A1 | 10/2013 | Baumhof et al. |
| 2013/0280283 A1 | 10/2013 | Lorenz et al. |
| 2013/0295043 A1 | 11/2013 | Kallen et al. |
| 2013/0336998 A1 | 12/2013 | Kallen et al. |
| 2015/0037326 A1 | 2/2015 | Butler-Ransohoff et al. |
| 2015/0050302 A1 | 2/2015 | Thess |
| 2015/0057340 A1 | 2/2015 | Thess et al. |
| 2015/0093413 A1 * | 4/2015 | Thess ............... A61K 39/145 536/23.7 |
| 2015/0118183 A1 | 4/2015 | Baumhof |
| 2015/0118264 A1 | 4/2015 | Baumhof et al. |
| 2015/0165006 A1 | 6/2015 | Thess et al. |
| 2015/0184195 A1 | 7/2015 | Thess et al. |
| 2015/0218554 A1 | 8/2015 | Thess |
| 2015/0306249 A1 | 10/2015 | Baumhof et al. |
| 2015/0320847 A1 | 11/2015 | Thess et al. |
| 2016/0130345 A1 | 5/2016 | Fotin-Mleczek et al. |
| 2016/0166668 A1 | 6/2016 | Kallen et al. |
| 2016/0166678 A1 | 6/2016 | Kallen et al. |
| 2016/0166710 A1 | 6/2016 | Baumhof |
| 2016/0166711 A1 | 6/2016 | Schnee et al. |
| 2016/0168207 A1 | 6/2016 | Kramps |
| 2016/0168227 A1 | 6/2016 | Kallen et al. |
| 2016/0235864 A1 | 8/2016 | Schlake et al. |
| 2016/0304883 A1 | 10/2016 | Grund et al. |
| 2016/0304938 A1 | 10/2016 | Wochner |
| 2016/0326575 A1 | 11/2016 | Von Der Mülbe et al. |
| 2016/0331844 A1 | 11/2016 | Fotin-Mleczek et al. |
| 2017/0014496 A1 | 1/2017 | Fotin-Mleczek et al. |
| 2017/0326225 A1 | 11/2017 | Rauch et al. |
| 2018/0125952 A1 | 5/2018 | Fotin-Mleczek et al. |
| 2018/0126003 A1 | 5/2018 | Hoerr |
| 2018/0148727 A1 | 5/2018 | Grund et al. |
| 2018/0208957 A1 | 7/2018 | Roos et al. |
| 2018/0237786 A1 | 8/2018 | Schlake et al. |
| 2018/0237817 A1 | 8/2018 | Roos et al. |
| 2018/0296663 A1 | 10/2018 | Hipp et al. |
| 2018/0312545 A1 | 11/2018 | Baumhof et al. |
| 2018/0371392 A1 | 12/2018 | Mayer et al. |
| 2019/0017100 A1 | 1/2019 | Wochner et al. |
| 2019/0024096 A1 | 1/2019 | Schmid et al. |
| 2019/0049414 A1 | 2/2019 | Wochner et al. |
| 2019/0083602 A1 | 3/2019 | Roos et al. |
| 2019/0100784 A1 | 4/2019 | Eber et al. |
| 2019/0177714 A1 | 6/2019 | Kunze et al. |
| 2019/0185859 A1 | 6/2019 | Fotin-Mleczek et al. |
| 2019/0194760 A1 | 6/2019 | Koch et al. |
| 2019/0225971 A1 | 7/2019 | Williams |
| 2019/0336608 A1 | 11/2019 | Baumhof et al. |

(56) References Cited

U.S. PATENT DOCUMENTS

| | | |
|---|---|---|
| 2019/0336611 A1 | 11/2019 | Baumhof et al. |
| 2019/0343942 A1 | 11/2019 | Fotin-Mleczek et al. |
| 2019/0351047 A1 | 11/2019 | Jasny et al. |
| 2019/0381180 A1 | 12/2019 | Baumhof et al. |
| 2020/0016264 A1 | 1/2020 | Hoerr et al. |
| 2020/0023076 A1 | 1/2020 | Fotin-Mleczek et al. |
| 2020/0085852 A1 | 3/2020 | Fotin-Mleczek |
| 2020/0085944 A1 | 3/2020 | Heidenreich et al. |
| 2020/0149026 A1 | 5/2020 | Horscroft et al. |
| 2020/0163878 A1 | 5/2020 | Baumhof et al. |
| 2020/0392572 A1 | 12/2020 | Yazdan Panah et al. |
| 2021/0030864 A1 | 2/2021 | Petsch et al. |
| 2021/0069315 A1 | 3/2021 | Baumhof et al. |
| 2021/0162037 A1 | 6/2021 | Jasny et al. |
| 2021/0170017 A1 | 6/2021 | Lutz et al. |
| 2021/0180106 A1 | 6/2021 | Wochner et al. |
| 2021/0205434 A1 | 7/2021 | Petsch et al. |
| 2021/0260178 A1 | 8/2021 | Jasny et al. |
| 2021/0261897 A1 | 8/2021 | Yazdan Panah et al. |
| 2021/0308238 A1 | 10/2021 | Hoerr et al. |
| 2021/0361761 A1 | 11/2021 | Lutz et al. |
| 2021/0403925 A1 | 12/2021 | Chevessier-Tünnesen et al. |
| 2022/0040281 A1 | 2/2022 | Schwendt et al. |
| 2022/0073962 A1 | 3/2022 | Schwenger et al. |
| 2022/0133908 A1 | 5/2022 | Rejman et al. |
| 2022/0144877 A1 | 5/2022 | Heinz et al. |
| 2022/0211838 A1 | 7/2022 | Oostvogels et al. |
| 2022/0296628 A1 | 9/2022 | Thess et al. |
| 2022/0313813 A1 | 10/2022 | Rauch et al. |

FOREIGN PATENT DOCUMENTS

| | | |
|---|---|---|
| WO | WO 2006/015789 | 2/2006 |
| WO | WO 2009/127230 | 10/2009 |
| WO | WO 2010/088927 | 8/2010 |
| WO | WO 2011/069528 | 6/2011 |
| WO | WO 2011/069587 | 6/2011 |
| WO | WO 2011/144358 | 11/2011 |
| WO | WO 2012/013326 | 2/2012 |
| WO | WO 2012/019630 | 2/2012 |
| WO | WO 2012/019780 | 2/2012 |
| WO | WO 2012/089338 | 7/2012 |
| WO | WO 2012/113513 | 8/2012 |
| WO | WO 2012/116714 | 9/2012 |
| WO | WO 2012/116715 | 9/2012 |
| WO | WO 2012/116810 | 9/2012 |
| WO | WO 2012/116811 | 9/2012 |
| WO | WO 2013/113501 | 8/2013 |
| WO | WO 2013/113502 | 8/2013 |
| WO | WO 2013/113736 | 8/2013 |
| WO | WO 2013/120626 | 8/2013 |
| WO | WO 2013/120627 | 8/2013 |
| WO | WO 2013/120628 | 8/2013 |
| WO | WO 2013/120629 | 8/2013 |
| WO | WO 2013/143698 | 10/2013 |
| WO | WO 2013/143699 | 10/2013 |
| WO | WO 2013/143700 | 10/2013 |
| WO | WO 2013/174409 | 11/2013 |
| WO | WO 2015/024665 | 2/2015 |
| WO | WO 2015/101414 | 7/2015 |
| WO | WO 2015/149944 | 10/2015 |

OTHER PUBLICATIONS

Amann et al., "A new rabies vaccine based on a recombinant ORF virus (parapovirus) expressing the rabies virus glycoprotein," *J. Virol.*, 87(3):1618-1630, 2013.

Bauer et al., "The impact of intragenic CpG content on gene expression," *Nucleic Acids Research*, 38(12):3891-3908, 2010.

Etl et al., "Novel Vaccines to Human Rabies," *PLoS Neglected Trop. Dis.*, 3(9):e515, 2009.

Fotin-Mleczek et al., "Highly potent mRNA based cancer vaccines represent an attractive platform for combination therapies supporting an improved therapeutic effect," *The Journal of Gene Medicine*, 14(6):428-439, 2012.

Paolazzi et al., "Rabies vaccine. Developments employing molecular biology methods," Molecular Biotechnology, 11:137-147, 1999.

PCT International Search Report and Written Opinion issued in International Application No. PCT/EP2014/002298, mailed Oct. 29, 2014.

Petsch et al., "Protective efficacy of in vitro synthesized, specific mRNA vaccines against influenza A virus infection," *Nature Biotechnology*, 30(12):1210-1216, 2012.

Schlake et al., "Developing mRNA-vaccine technologies," *RNA Biology*, 9(11):1319-1330, 2012.

Tordo et al., "Walking along the rabies genome: is the large G-L intergenic region a remnant gene?" *Proceedings of the National Academy of Sciences of the United States of America*, 83(11):3914-3918, 1986.

Wang et al., "Post-exposure prophylaxis vaccination rate and risk factors of human rabies in mainland China: a meta-analysis", *Epidemiol. Infect.*, 147(e64):1-6, 2018.

GenBank Accession No. GU936866.1, Nov. 8, 2010.

UniProt Accession No. P08667, Jun. 15, 2010.

\* cited by examiner

R2403: RAV-G(GC)-muag-A64-C30-histoneSL

GGGAGAAAGCUUACCAUGGUGCCCCAGGCCCUGCUCUUCGUCCCGCUGCUGGUGUUCCCC
CUCUGCUUCGGCAAGUUCCCCAUCUACACCAUCCCCGACAAGCUGGGGCCGUGGAGCCCC
AUCGACAUCCACCACCUGUCCUGCCCCAACAACCUCGUGGUCGAGGACGAGGGCUGCACC
AACCUGAGCGGGUUCUCCUACAUGGAGCUGAAGGUGGGCUACAUCAGCGCCAUCAAGAUG
AACGGGUUCACGUGCACCGGCGUGGUCACCGAGGCGGAGACCUACACGAACUUCGUGGGC
UACGUGACCACCACCUUCAAGCGGAAGCACUUCCGCCCCACGCCGGACGCCUGCCGGGCC
GCCUACAACUGGAAGAUGGCCGGGGACCCCCGCUACGAGGAGUCCCUCCACAACCCCUAC
CCCGACUACCACUGGCUGCGGACCGUCAAGACCACCAAGGAGAGCCUGGUGAUCAUCUCC
CCGAGCGUGGCGGACCUCGACCCCUACGACCGCUCCCUGCACAGCCGGGUCUUCCCCGGC
GGGAACUGCUCCGGCGUGGCCGUGAGCUCCACGUACUGCAGCACCAACCACGACUACACC
AUCUGGAUGCCCGAGAACCCGCGCCUGGGGAUGUCCUGCGACAUCUUCACCAACAGCCGG
GGCAAGCGCGCCUCCAAGGGCAGCGAGACGUGCGGGUUCGUCGACGAGCGGGGCCUCUAC
AAGUCCCUGAAGGGGGCCUGCAAGCUGAAGCUCUGCGGCGUGCUGGGCCUGCGCCUCAUG
GACGGGACCUGGGUGGCGAUGCAGACCAGCAACGAGACCAAGUGGUGCCCCCCCGGCCAG
CUGGUCAACCUGCACGACUUCCGGAGCGACGAGAUCGAGCACCUCGUGGUGGAGGAGCUG
GUCAAGAAGCGCGAGGAGUGCCUGGACGCCCUCGAGUCCAUCAUGACGACCAAGAGCGUG
UCCUUCCGGCGCCUGAGCCACCUGCGGAAGCUCGUGCCCGGGUUCGGCAAGGCCUACACC
AUCUUCAACAAGACCCUGAUGGAGGCCGACGCCCACUACAAGUCCGUCCGCACGUGGAAC
GAGAUCAUCCCGAGCAAGGGGUGCCUGCGGGUGGGCGGCCGCUGCCACCCCACGUCAAC
GGGGUGUUCUUCAACGGCAUCAUCCUCGGGCCCGACGGCAACGUGCUGAUCCCCGAGAUG
CAGUCCAGCCUGCUCCAGCAGCACAUGGAGCUGCUGGUCUCCAGCGUGAUCCCGCUCAUG
CACCCCCUGGCGGACCCCUCCACCGUGUUCAAGAACGGGGACGAGGCCGAGGACUUCGUC
GAGGUGCACCUGCCCGACGUGCACGAGCGGAUCAGCGGCGUCGACCUCGGCCUGCCGAAC
UGGGGGAAGUACGUGCUGCUCUCCGCCGGCGCCCUGACCGCCCUGAUGCUGAUCAUCUUC
CUCAUGACCUGCUGGCGCCGGGUGAACCGGAGCGAGCCCACGCAGCACAACCUGCGCGGG
ACCGGCCGGGAGGUCUCCGUGACCCCGCAGAGCGGGAAGAUCAUCUCCAGCUGGGAGUCC
UACAAGAGCGGCGGCGAGACCGGGCUGUGAGGACUAGUUAUAAGACUGACUAGCCCGAUG
GGCCUCCCAACGGGCCCUCCUCCCCUCCUUGCACCGAGAUUAAUAAAAAAAAAAAAAAAA
AAAAAAAAAAAAAAAAAAAAAAAAAAAAAAAAAAAAAAAAAAAAAAUGCAUCCCCCCC
CCCCCCCCCCCCCCCCCCCCCCAAAGGCUCUUUUCAGAGCCACCAGAAUU

Fig. 1

R2507: 32L-RAV-G(GC)-albumin7-A64-C30-histoneSL

```
GGGGCGCUGCCUACGGAGGUGGCAGCCAUCUCCUUCUCGGCAUCAAGCUUACCAUGGUGC
CCCAGGCCCUGCUCUUCGUCCCGCUGCUGGUGUUCCCCCUCUGCUUCGGCAAGUUCCCCA
UCUACACCAUCCCCGACAAGCUGGGGCCGUGGAGCCCCAUCGACAUCCACCACCUGUCCU
GCCCCAACAACCUCGUGGUCGAGGACGAGGGCUGCACCAACCUGAGCGGGUUCUCCUACA
UGGAGCUGAAGGUGGGCUACAUCAGCGCCAUCAAGAUGAACGGGUUCACGUGCACCGGCG
UGGUCACCGAGGCGGAGACCUACACGAACUUCGUGGGCUACGUGACCACCACCUUCAAGC
GGAAGCACUUCCGCCCCACGCCGGACGCCUGCCGGGCCGCCUACAACUGGAAGAUGGCCG
GGGACCCCGCUACGAGGAGUCCCUCCACAACCCCUACCCCGACUACCACUGGCUGCGGA
CCGUCAAGACCACCAAGGAGAGCCUGGUGAUCAUCUCCCCGAGCGUGGCGGACCUCGACC
CCUACGACCGCUCCCUGCACAGCCGGGUCUUCCCCGGCGGGAACUGCUCCGGCGUGGCCG
UGAGCUCCACGUACUGCAGCACCAACCACGACUACACCAUCUGGAUGCCCGAGAACCCGC
GCCUGGGGAUGUCCUGCGACAUCUUCACCAACAGCCGGGGCAAGCGCGCCUCCAAGGGCA
GCGAGACGUGCGGGUUCGUCGACGAGCGGGGCCUCUACAAGUCCCUGAAGGGGGCCUGCA
AGCUGAAGCUCUGCGGCGUGCUGGGCCUGCGCCUCAUGGACGGGACCUGGGUGGCGAUGC
AGACCAGCAACGAGACCAAGUGGUGCCCCCCGGCCAGCUGGUCAACCUGCACGACUUCC
GGAGCGACGAGAUCGAGCACCUCGUGGUGGAGGAGCUGGUCAAGAAGCGCGAGGAGUGCC
UGGACGCCCUCGAGUCCAUCAUGACGACCAAGAGCGUGUCCUUCCGGCGCCUGAGCCACC
UGCGGAAGCUCUGCCCGGGUUCGGCAAGGCCUACACCAUCUUCAACAAGACCCUGAUGG
AGGCCGACGCCCACUACAAGUCCGUCCGCACGUGGAACGAGAUCAUCCCGAGCAAGGGGU
GCCUGCGGGUGGGCGGCCGCUGCCACCCCCACGUCAACGGGGUGUUCUUCAACGGCAUCA
UCCUCGGGCCCGACGGCAACGUGCUGAUCCCCGAGAUGCAGUCCAGCCUGCUCCAGCAGC
ACAUGGAGCUGCUGGUCUCCAGCGUGAUCCCGCUCAUGCACCCCUGGCGGACCCCUCCA
CCGUGUUCAAGAACGGGGACGAGGCCGAGGACUUCGUCGAGGUGCACCUGCCCGACGUGC
ACGAGCGGAUCAGCGGCGUCGACCUCGGCCUGCCGAACUGGGGGAAGUACGUGCUGCUCU
CCGCCGGCGCCCUGACCGCCCUGAUGCUGAUCAUCUUCCUCAUGACCUGCUGGCGCCGGG
UGAACCGGAGCGAGCCCACGCAGCACAACCUGCGCGGGACCGGCCGGGAGGUCUCCGUGA
CCCCGCAGAGCGGGAAGAUCAUCUCCAGCUGGGAGUCCUACAAGAGCGGCGGCGAGACCG
GGCUGUGAGGACUAGUGCAUCACAUUUAAAAGCAUCUCAGCCUACCAUGAGAAUAAGAGA
AAGAAAAUGAAGAUCAAUAGCUUAUUCAUCUCUUUUUCUUUUUCGUUGGUGUAAAGCCAA
CACCCUGUCUAAAAACAUAAAUUUCUUUAAUCAUUUGCCUCUUUUCUCUGUGCUUCAA
UUAAUAAAAAUGGAAAGAACCUAGAUCUAAAAAAAAAAAAAAAAAAAAAAAAAAAAA
AAAAAAAAAAAAAAAAAAAAAAAAAAAAAAAAUGCAUCCCCCCCCCCCCCCCCCCC
CCCCCCCCCAAAGGCUCUUUUCAGAGCCACCAGAAUU
```

Fig. 2

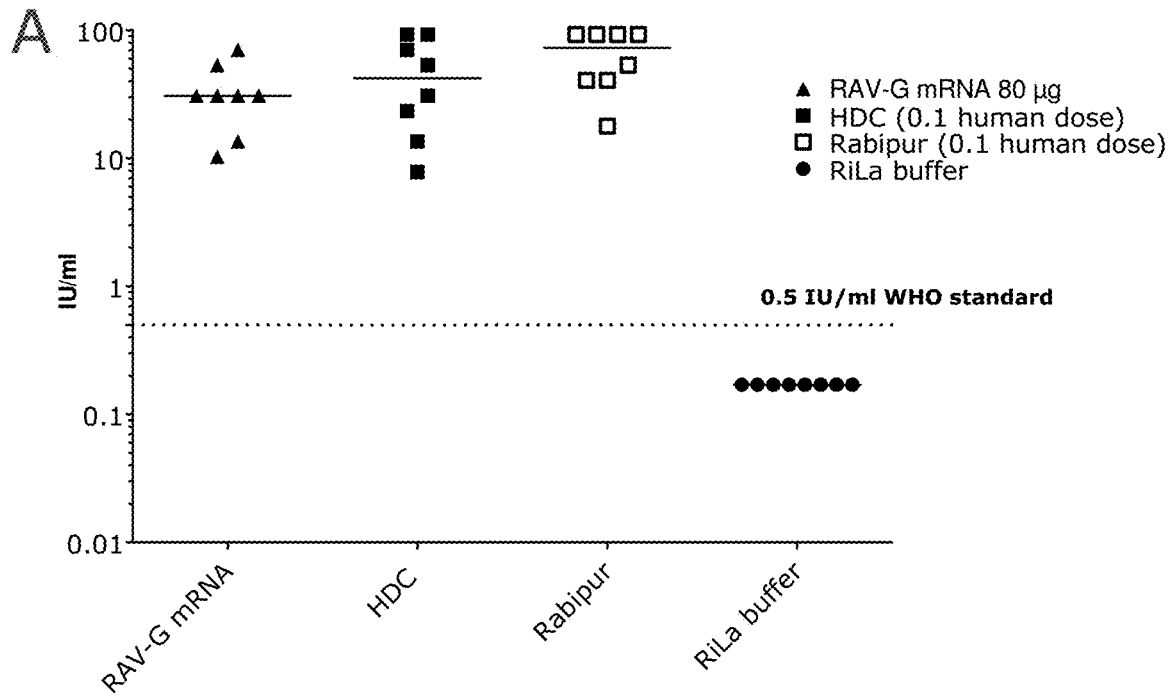
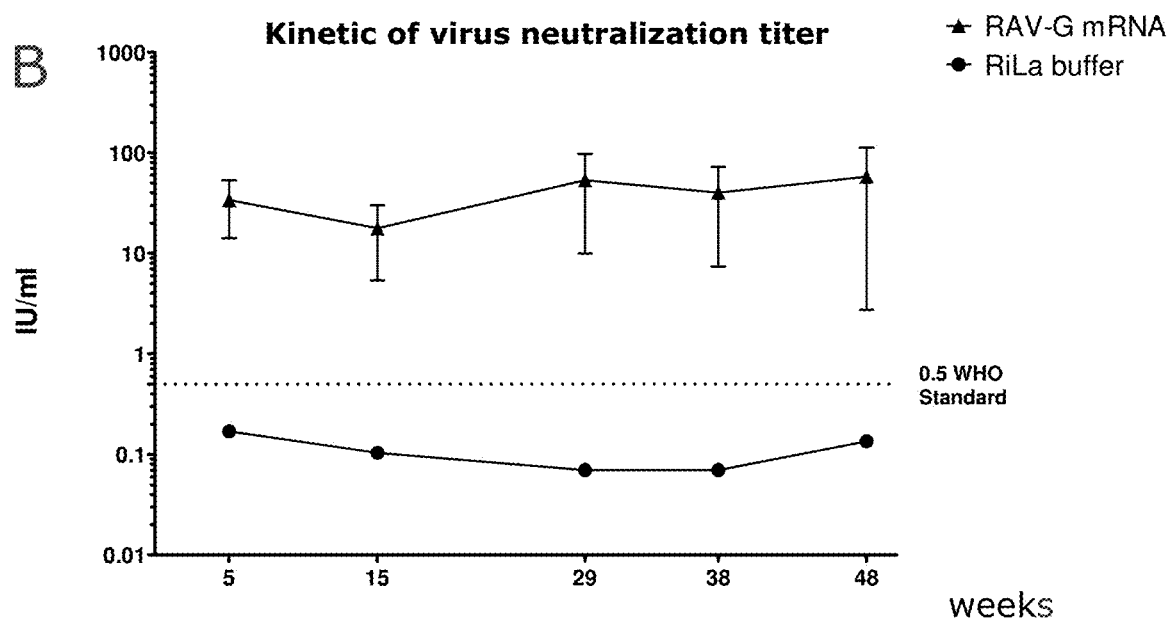
Figs. 4A-B

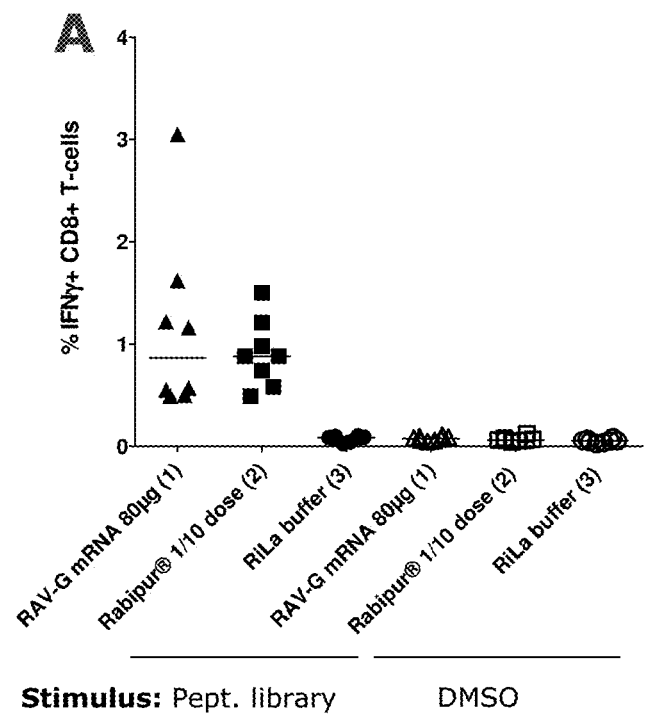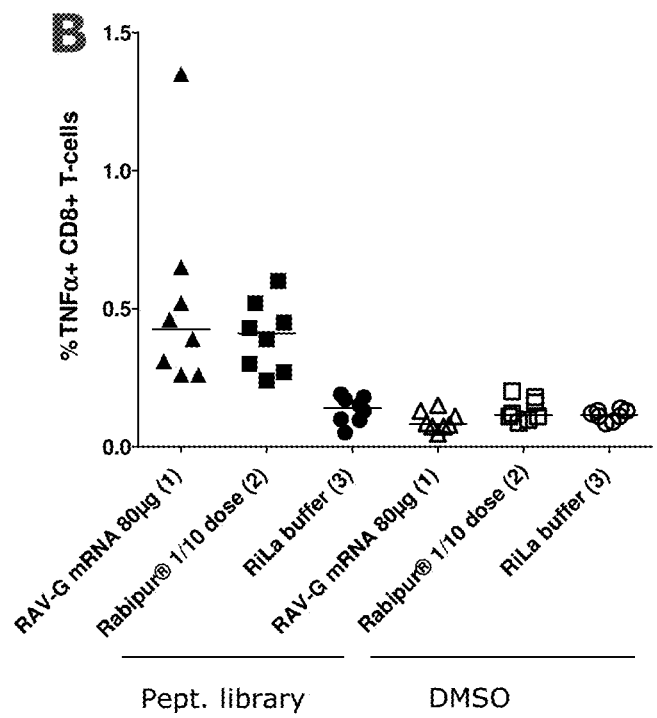
Figs. 5A-B

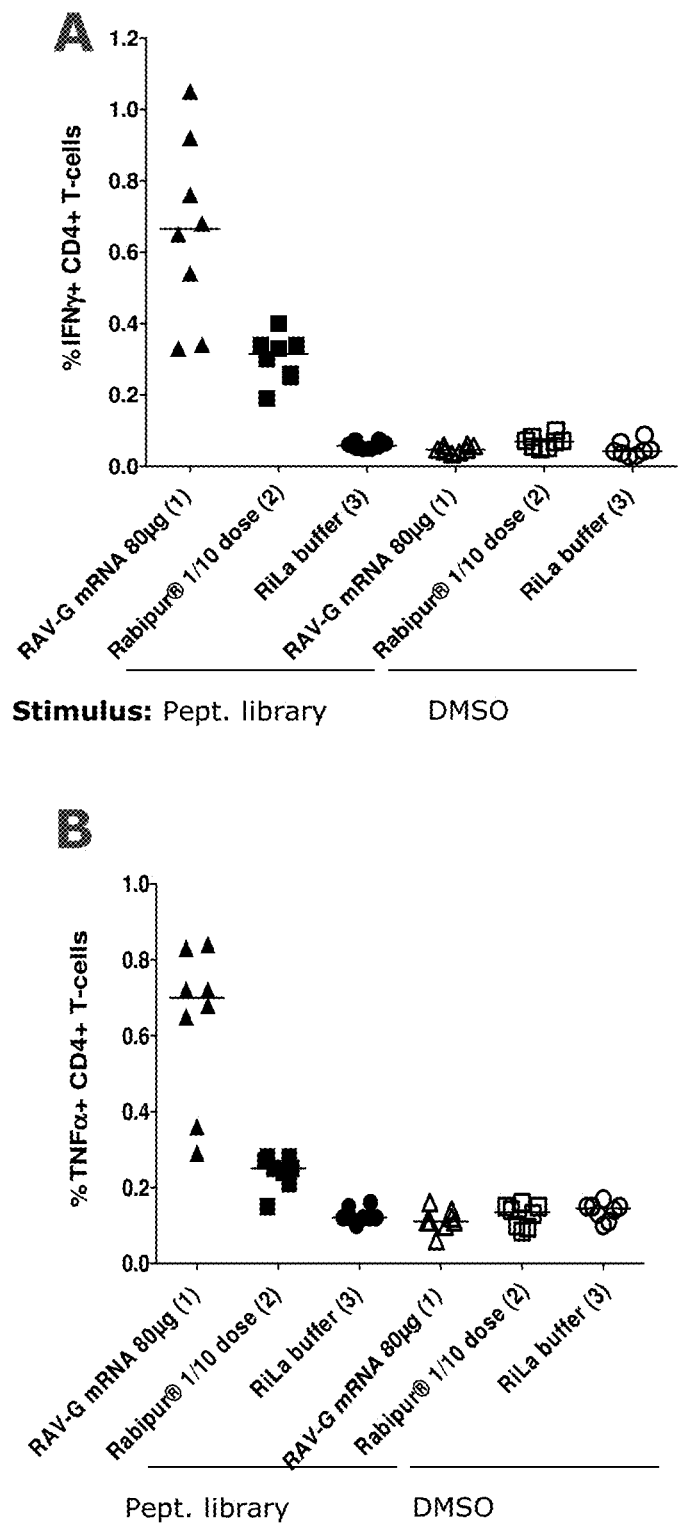
Figs. 6A-B

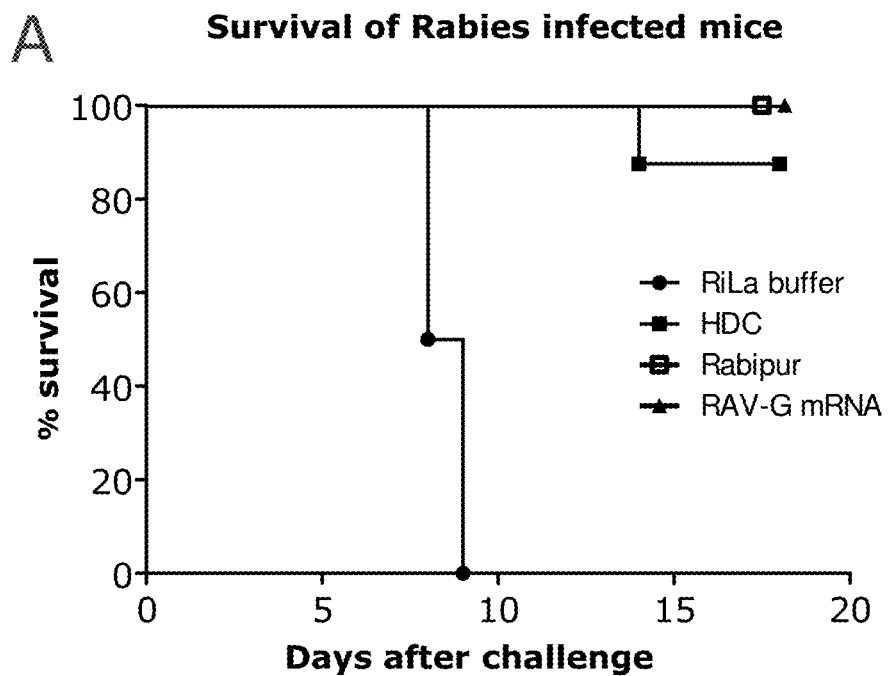
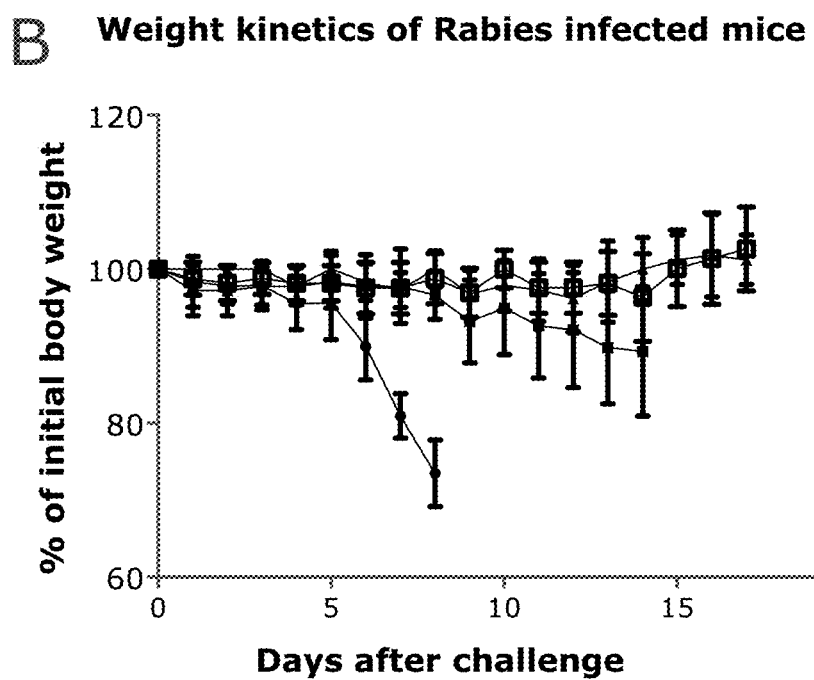
Figs. 8A-B

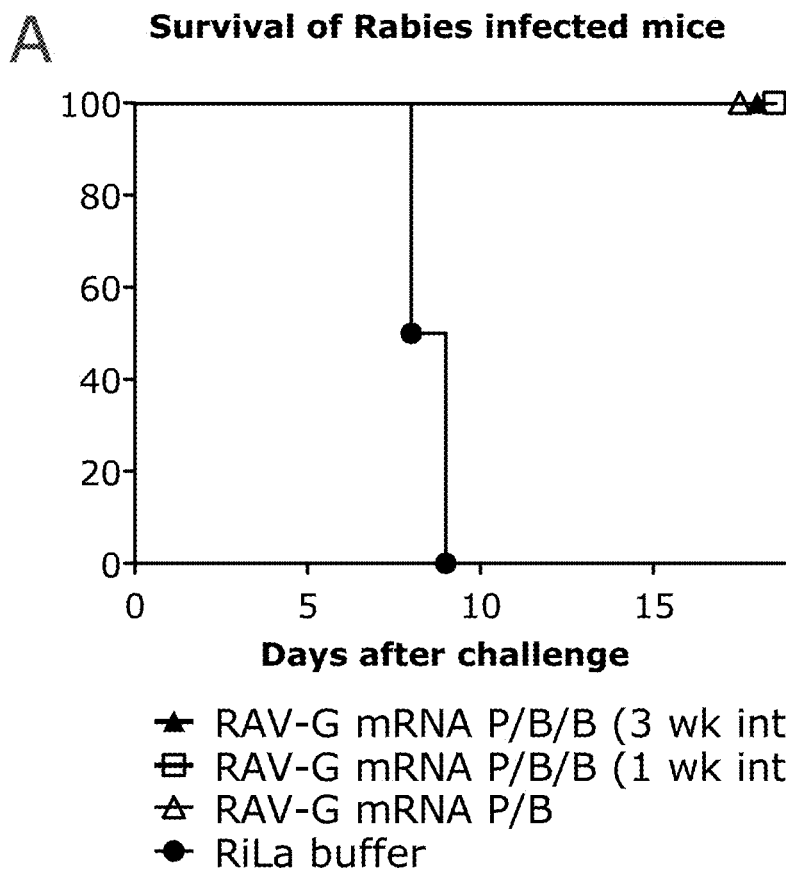
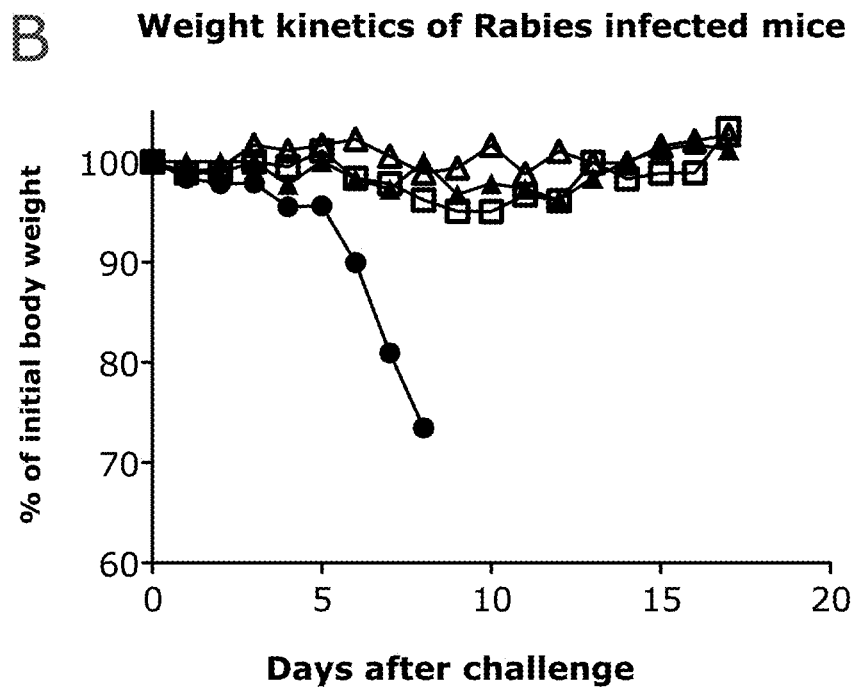
Figs. 9A-B

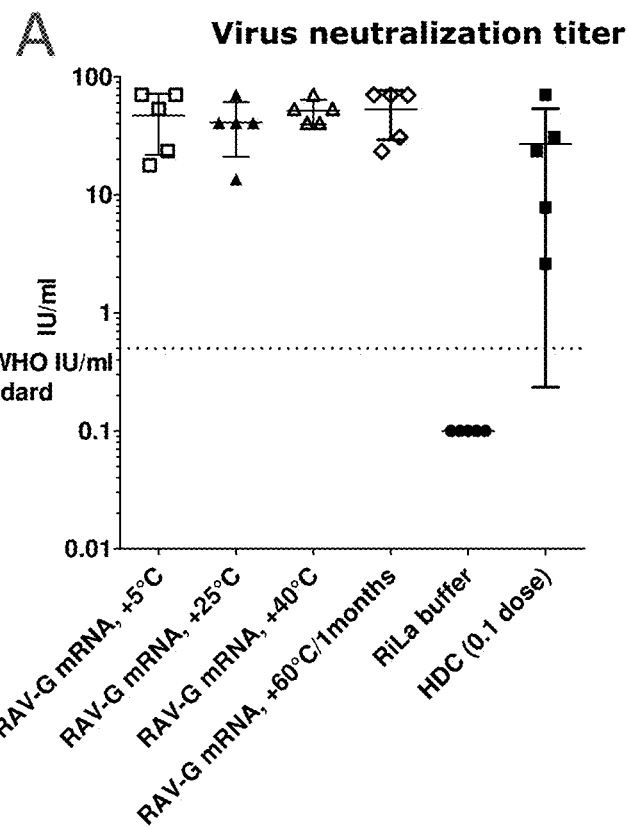
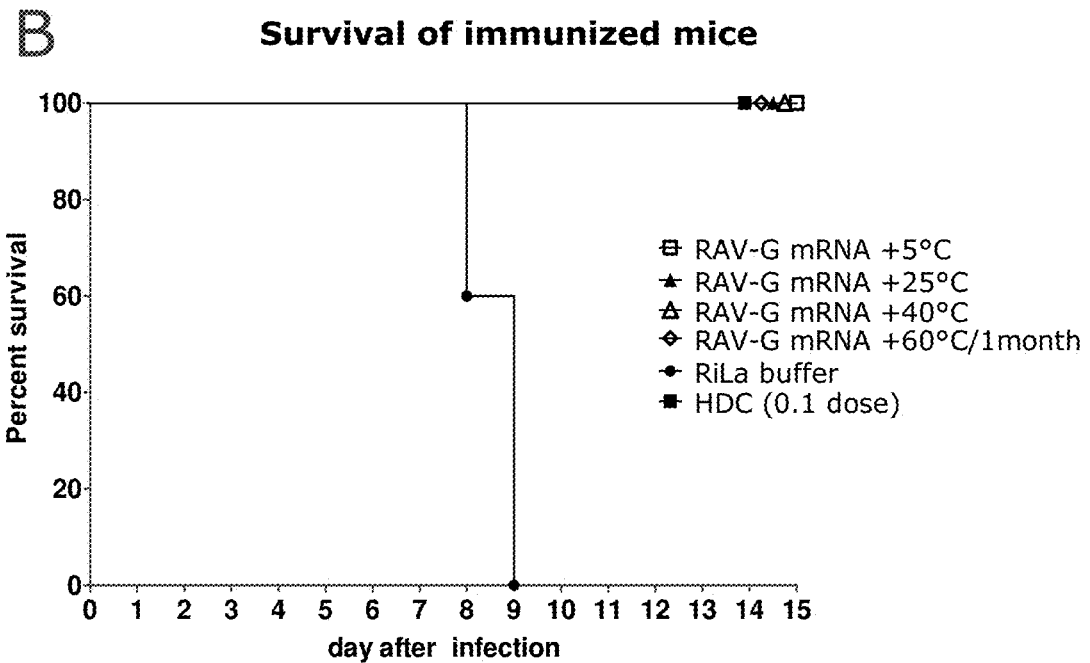
Figs. 10A-B

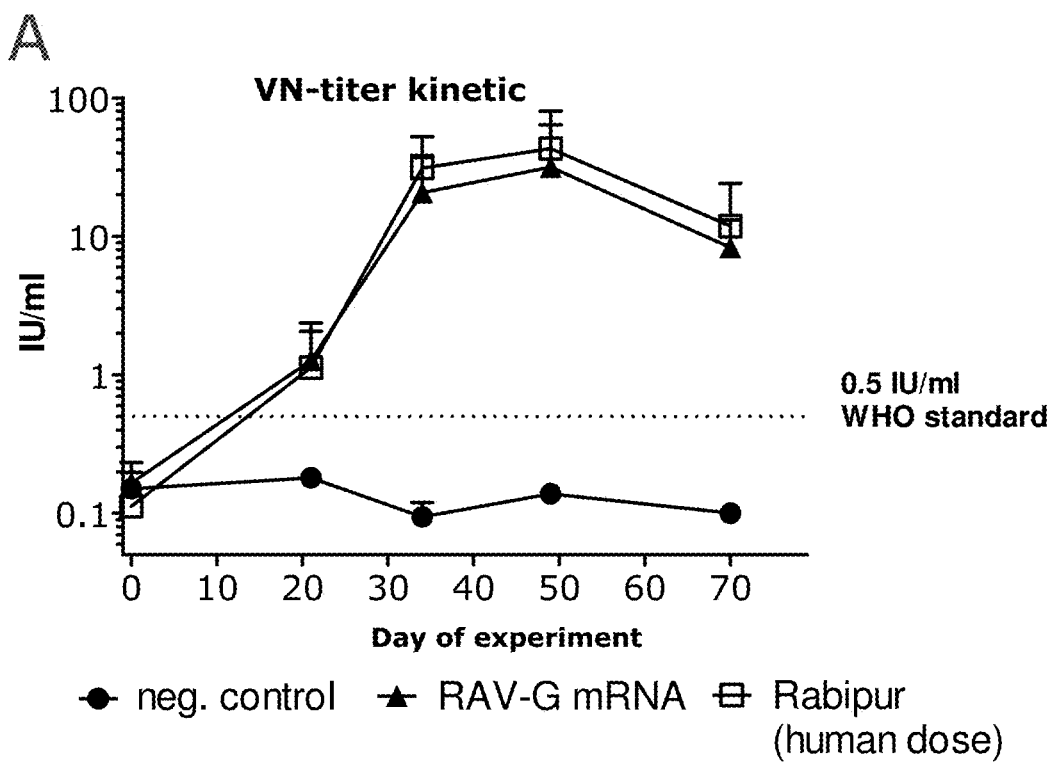
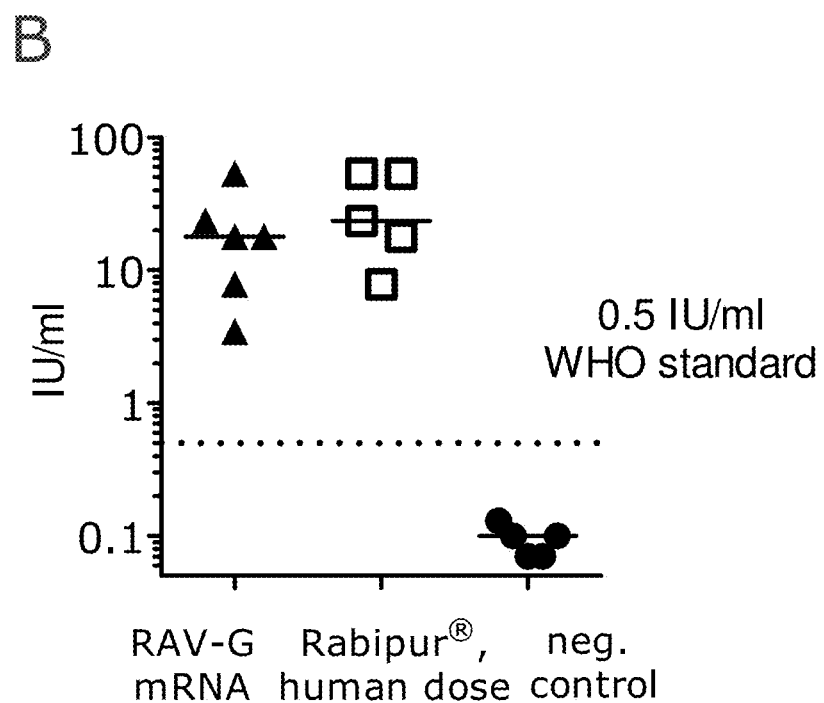
Figs. 12A-B

RABIES VACCINE

The present application is a divisional of U.S. application Ser. No. 16/865,107, filed May 1, 2020, which is a divisional of U.S. application Ser. No. 15/048,356, filed Feb. 19, 2016, now U.S. Pat. No. 10,682,426, which is a continuation of International Application No. PCT/EP2014/002298, filed Aug. 21, 2014, which claims priority benefit of International Application No. PCT/EP2013/002517, filed Aug. 21, 2013, the entire text of each of the above referenced disclosures being specifically incorporated herein by reference.

BACKGROUND OF THE INVENTION

The present invention relates to an mRNA sequence, comprising a coding region, encoding at least one antigenic peptide or protein of Rabies virus or a fragment, variant or derivative thereof. Additionally the present invention relates to a composition comprising a plurality of mRNA sequences comprising a coding region, encoding at least one antigenic peptide or protein of Rabies virus or a fragment, variant or derivative thereof.

Furthermore it also discloses the use of the mRNA sequence or the composition comprising a plurality of mRNA sequences for the preparation of a pharmaceutical composition, especially a vaccine, e.g. for use in the prophylaxis, postexposure prophylaxis or treatment of Rabies virus infections. The present invention further describes a method of treatment, postexposure prophylaxis or prophylaxis of rabies using the mRNA sequence.

Rabies is a viral zoonosis, endemic in more than 100 countries and territories (WHO epidemiological record 2007a. No. 49/50 (82):425-436. Rabies vaccines: WHO position paper), and poses a threat to more than 3 billion people (Knobel D L et al. Re-evaluating the burden of rabies in Africa and Asia. Bulletin of the World Health Organisation 2005; 83:360-368). The disease is invariably fatal following the onset of clinical symptoms occurring in the absence of postexposure prophylaxis (WHO epidemiological record 2010. No. 32 (85):309-320. Rabies vaccine: WHO position paper). The WHO assumes 55000 rabies related deaths and the postexposure treatment (PET) of more than 10 million people each year (WHO Weekly epidemiological record, No. 49/50, 2007b, 82:425-436).

Currently available rabies vaccines include the most widely used but highly risk-prone nerve tissue vaccines, or the safer but more costly cell culture and embryonated egg vaccines (CCEEVs). Risks associated with nerve tissue vaccines include induction of autoimmune central nervous system disease due to their inherent myelin content; the need for multiple injections; and unreliable efficacy (Plotkin S A. Rabies. Clin Infect Dis 2000; 30:4-12). The WHO does not recommend the use of nerve tissue vaccines and strongly encourages the increased supply of modern and high quality vaccines to poor populations (WHO epidemiological record 2007a. No. 49/50 (82):425-436. Rabies vaccines: WHO position paper). Avian embryo vaccines and cell culture vaccines contain inactivated purified virus, free from nerve protein. Although safer and more immunogenic than nerve tissue vaccines, cell culture production methods are time-consuming and resource-intensive and the associated cost burden largely restricts the use to the developed world (Warrell M J and Warrell D A. Intradermal postexposure rabies vaccine regimens. Clin Infect Dis 2000; 31:844-845) despite of WHO current recommendations.

Pre-exposure prophylaxis (PrEP) with cell culture vaccine is safe, and is recommended for individuals at increased risk (e.g., laboratory staff, veterinarians, animal handlers, wildlife workers and travellers to rabies-endemic areas), but it is largely restricted for reasons of cost to the developed world. Furthermore, the anti-rabies vaccine is recommended for people travelling to countries in Africa and Asia, where rabies is endemic (STIKO 2011).

In Germany e.g. only two anti-rabies vaccines are on the market, Rabipur® and "Tollwut-Impfstoff (human diploid cell [HDC]) inaktiviert". These vaccines contain inactivated rabies virus. Both vaccines are recommended for pre- and postexposure use. After contact with rabid or suspected rabid animals, PET (post-exposure treatment) is recommended with vaccinations on days 0, 3, 7, 14 and 28 after exposure. Combined with the vaccination, proper wound management and simultaneous administration of rabies immunoglobulin (Ig) should be performed to effectively prevent the disease.

A current problem is a shortage of these vaccines, which are, at certain times, only available for postexposure prophylaxis and not for prophylactic vaccination. Prophylactic vaccination is, however, important for travellers visiting developing countries where rabies virus Ig for postexposure prophylaxis may not be available.

Therefore there is a need for a save and effective rabies vaccine which can be delivered at any time. Furthermore there is an urgent need for a temperature stabile rabies vaccine which is not dependent on cooling (cold chain).

Furthermore, there is an unmet medical need to improve the effectiveness of rabies vaccine delivery and for the development of a safe and effective rabies vaccine that is more affordable and more rapidly manufactured than the currently available cell culture vaccines.

Therefore it is the object of the underlying invention to provide an mRNA sequence coding for antigenic peptides or proteins of Rabies virus for the use as vaccine for prophylaxis or treatment of rabies, particularly for preexposure prophylaxis or postexposure prophylaxis. Furthermore it is the object of the present invention to provide an effective rabies vaccine which can be stored without cold chain and which enables rapid and scalable vaccine production.

These objects are solved by the subject matter of the attached claims. Particularly, the objects underlying the present invention are solved according to a first aspect by an inventive mRNA sequence comprising a coding region, encoding at least one antigenic peptide or protein of Rabies virus or a fragment, variant or derivative thereof.

For the sake of clarity and readability the following scientific background information and definitions are provided. Any technical features disclosed thereby can be part of each and every embodiment of the invention. Additional definitions and explanations can be provided in the context of this disclosure.

Immune system: The immune system may protect organisms from infection. If a pathogen breaks through a physical barrier of an organism and enters this organism, the innate immune system provides an immediate, but non-specific response. If pathogens evade this innate response, vertebrates possess a second layer of protection, the adaptive immune system. Here, the immune system adapts its response during an infection to improve its recognition of the pathogen. This improved response is then retained after the pathogen has been eliminated, in the form of an immunological memory, and allows the adaptive immune system to mount faster and stronger attacks each time this pathogen is encountered. According to this, the immune system comprises the innate and the adaptive immune system. Each of these two parts contains so called humoral and cellular components.

Immune response: An immune response may typically either be a specific reaction of the adaptive immune system to a particular antigen (so called specific or adaptive immune response) or an unspecific reaction of the innate immune system (so called unspecific or innate immune response). The invention relates to the core to specific reactions (adaptive immune responses) of the adaptive immune system. Particularly, it relates to adaptive immune responses to infections by viruses like e.g. Rabies. However, this specific response can be supported by an additional unspecific reaction (innate immune response). Therefore, the invention also relates to a compound for simultaneous stimulation of the innate and the adaptive immune system to evoke an efficient adaptive immune response.

Adaptive immune system: The adaptive immune system is composed of highly specialized, systemic cells and processes that eliminate or prevent pathogenic growth. The adaptive immune response provides the vertebrate immune system with the ability to recognize and remember specific pathogens (to generate immunity), and to mount stronger attacks each time the pathogen is encountered. The system is highly adaptable because of somatic hypermutation (a process of increased frequency of somatic mutations), and V(D)J recombination (an irreversible genetic recombination of antigen receptor gene segments). This mechanism allows a small number of genes to generate a vast number of different antigen receptors, which are then uniquely expressed on each individual lymphocyte. Because the gene rearrangement leads to an irreversible change in the DNA of each cell, all of the progeny (offspring) of that cell will then inherit genes encoding the same receptor specificity, including the Memory B cells and Memory T cells that are the keys to long-lived specific immunity. Immune network theory is a theory of how the adaptive immune system works, that is based on interactions between the variable regions of the receptors of T cells, B cells and of molecules made by T cells and B cells that have variable regions.

Adaptive immune response: The adaptive immune response is typically understood to be antigen-specific. Antigen specificity allows for the generation of responses that are tailored to specific antigens, pathogens or pathogen-infected cells. The ability to mount these tailored responses is maintained in the body by "memory cells". Should a pathogen infect the body more than once, these specific memory cells are used to quickly eliminate it. In this context, the first step of an adaptive immune response is the activation of naïve antigen-specific T cells or different immune cells able to induce an antigen-specific immune response by antigen-presenting cells. This occurs in the lymphoid tissues and organs through which naïve T cells are constantly passing. Cell types that can serve as antigen-presenting cells are inter alia dendritic cells, macrophages, and B cells. Each of these cells has a distinct function in eliciting immune responses. Dendritic cells take up antigens by phagocytosis and macropinocytosis and are stimulated by contact with e.g. a foreign antigen to migrate to the local lymphoid tissue, where they differentiate into mature dendritic cells. Macrophages ingest particulate antigens such as bacteria and are induced by infectious agents or other appropriate stimuli to express MHC molecules. The unique ability of B cells to bind and internalize soluble protein antigens via their receptors may also be important to induce T cells. Presenting the antigen on MHC molecules leads to activation of T cells which induces their proliferation and differentiation into armed effector T cells. The most important function of effector T cells is the killing of infected cells by CD8+ cytotoxic T cells and the activation of macrophages by Th1 cells which together make up cell-mediated immunity, and the activation of B cells by both Th2 and Th1 cells to produce different classes of antibody, thus driving the humoral immune response. T cells recognize an antigen by their T cell receptors which do not recognize and bind antigen directly, but instead recognize short peptide fragments e.g. of pathogen-derived protein antigens, which are bound to MHC molecules on the surfaces of other cells.

Cellular immunity/cellular immune response: Cellular immunity relates typically to the activation of macrophages, natural killer cells (NK), antigen-specific cytotoxic T-lymphocytes, and the release of various cytokines in response to an antigen. In a more general way, cellular immunity is not related to antibodies but to the activation of cells of the immune system. A cellular immune response is characterized e.g. by activating antigen-specific cytotoxic T-lymphocytes that are able to induce apoptosis in body cells displaying epitopes of an antigen on their surface, such as virus-infected cells, cells with intracellular bacteria, and cancer cells displaying tumor antigens; activating macrophages and natural killer cells, enabling them to destroy pathogens; and stimulating cells to secrete a variety of cytokines that influence the function of other cells involved in adaptive immune responses and innate immune responses.

Humoral immunity/humoral immune response: Humoral immunity refers typically to antibody production and the accessory processes that may accompany it. A humoral immune response may be typically characterized, e.g., by Th2 activation and cytokine production, germinal center formation and isotype switching, affinity maturation and memory cell generation. Humoral immunity also typically may refer to the effector functions of antibodies, which include pathogen and toxin neutralization, classical complement activation, and opsonin promotion of phagocytosis and pathogen elimination.

Innate immune system: The innate immune system, also known as non-specific immune system, comprises the cells and mechanisms that defend the host from infection by other organisms in a non-specific manner. This means that the cells of the innate system recognize and respond to pathogens in a generic way, but unlike the adaptive immune system, it does not confer long-lasting or protective immunity to the host. The innate immune system may be e.g. activated by ligands of pathogen-associated molecular patterns (PAMP) receptors, e.g. Toll-like receptors (TLRs) or other auxiliary substances such as lipopolysaccharides, TNF-alpha, CD40 ligand, or cytokines, monokines, lymphokines, interleukins or chemokines, IL-1, IL-2, IL-3, IL-4, IL-5, IL-6, IL-7, IL-8, IL-9, IL-10, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IFN-alpha, IFN-beta, IFN-gamma, GM-CSF, G-CSF, M-CSF, LT-beta, TNF-alpha, growth factors, and hGH, a ligand of human Toll-like receptor TLR1, TLR2, TLR3, TLR4, TLR5, TLR6, TLR7, TLR8, TLR9, TLR10, a ligand of murine Toll-like receptor TLR1, TLR2, TLR3, TLR4, TLR5, TLR6, TLR7, TLR8, TLR9, TLR10, TLR11, TLR12 or TLR13, a ligand of a NOD-like receptor, a ligand of a RIG-I like receptor, an immunostimulatory nucleic acid, an immunostimulatory RNA (isRNA), a CpG-DNA, an antibacterial agent, or an anti-viral agent. Typically a response of the innate immune system includes recruiting immune cells to sites of infection, through the production of chemical factors, including specialized chemical mediators, called cytokines; activation of the complement cascade; identification and removal of foreign substances present in organs, tissues, the blood and lymph, by specialized white blood cells; activation of the adaptive immune system through a process known as antigen presentation; and/or acting as a physical and chemical barrier to infectious agents.

Adjuvant/adjuvant component: An adjuvant or an adjuvant component in the broadest sense is typically a (e.g. pharmacological or immunological) agent or composition that may modify, e.g. enhance, the efficacy of other agents, such as a drug or vaccine. Conventionally the term refers in the context of the invention to a compound or composition that serves as a carrier or auxiliary substance for immunogens and/or other pharmaceutically active compounds. It is to be interpreted in a broad sense and refers to a broad spectrum of substances that are able to increase the immunogenicity of antigens incorporated into or co-administered with an adjuvant in question. In the context of the present invention an adjuvant will preferably enhance the specific immunogenic effect of the active agents of the present invention. Typically, "adjuvant" or "adjuvant component" has the same meaning and can be used mutually. Adjuvants may be divided, e.g., into immuno potentiators, antigenic delivery systems or even combinations thereof.

The term "adjuvant" is typically understood not to comprise agents which confer immunity by themselves. An adjuvant assists the immune system unspecifically to enhance the antigen-specific immune response by e.g. promoting presentation of an antigen to the immune system or induction of an unspecific innate immune response. Furthermore, an adjuvant may preferably e.g. modulate the antigen-specific immune response by e.g. shifting the dominating Th2-based antigen specific response to a more Th1-based antigen specific response or vice versa. Accordingly, an adjuvant may favourably modulate cytokine expression/secretion, antigen presentation, type of immune response etc.

Immunostimulatory RNA: An immunostimulatory RNA (isRNA) in the context of the invention may typically be a RNA that is able to induce an innate immune response itself. It usually does not have an open reading frame and thus does not provide a peptide-antigen or immunogen but elicits an innate immune response e.g. by binding to a specific kind of Toll-like-receptor (TLR) or other suitable receptors. However, of course also mRNAs having an open reading frame and coding for a peptide/protein (e.g. an antigenic function) may induce an innate immune response.

Antigen: According to the present invention, the term "antigen" refers typically to a substance which may be recognized by the immune system and may be capable of triggering an antigen-specific immune response, e.g. by formation of antibodies or antigen-specific T-cells as part of an adaptive immune response. An antigen may be a protein or peptide. In this context, the first step of an adaptive immune response is the activation of naïve antigen-specific T cells by antigen-presenting cells. This occurs in the lymphoid tissues and organs through which naïve T cells are constantly passing. The three cell types that can serve as antigen-presenting cells are dendritic cells, macrophages, and B cells. Each of these cells has a distinct function in eliciting immune responses. Tissue dendritic cells take up antigens by phagocytosis and macropinocytosis and are stimulated by infection to migrate to the local lymphoid tissue, where they differentiate into mature dendritic cells. Macrophages ingest particulate antigens such as bacteria and are induced by infectious agents to express MHC class II molecules. The unique ability of B cells to bind and internalize soluble protein antigens via their receptors may be important to induce T cells. By presenting the antigen on MHC molecules leads to activation of T cells which induces their proliferation and differentiation into armed effector T cells. The most important function of effector T cells is the killing of infected cells by $CD8^+$ cytotoxic T cells and the activation of macrophages by TH1 cells which together make up cell-mediated immunity, and the activation of B cells by both TH2 and TH1 cells to produce different classes of antibody, thus driving the humoral immune response. T cells recognize an antigen by their T cell receptors which does not recognize and bind antigen directly, but instead recognize short peptide fragments e.g. of pathogens' protein antigens, which are bound to MHC molecules on the surfaces of other cells.

T cells fall into two major classes that have different effector functions. The two classes are distinguished by the expression of the cell-surface proteins CD4 and CD8. These two types of T cells differ in the class of MHC molecule that they recognize. There are two classes of MHC molecules—MHC class I and MHC class II molecules—which differ in their structure and expression pattern on tissues of the body. $CD4^+$ T cells bind to a MHC class II molecule and $CD8^+$ T cells to a MHC class I molecule. MHC class I and MHC class II molecules have distinct distributions among cells that reflect the different effector functions of the T cells that recognize them. MHC class I molecules present peptides of cytosolic and nuclear origin e.g. from pathogens, commonly viruses, to $CD8^+$ T cells, which differentiate into cytotoxic T cells that are specialized to kill any cell that they specifically recognize. Almost all cells express MHC class I molecules, although the level of constitutive expression varies from one cell type to the next. But not only pathogenic peptides from viruses are presented by MHC class I molecules, also self-antigens like tumour antigens are presented by them. MHC class I molecules bind peptides from proteins degraded in the cytosol and transported in the endoplasmic reticulum. The $CD8^+$ T cells that recognize MHC class I:peptide complexes at the surface of infected cells are specialized to kill any cells displaying foreign peptides and so rid the body of cells infected with viruses and other cytosolic pathogens. The main function of $CD4^+$ T cells ($CD4^+$ helper T cells) that recognize MHC class II molecules is to activate other effector cells of the immune system. Thus MHC class II molecules are normally found on B lymphocytes, dendritic cells, and macrophages, cells that participate in immune responses, but not on other tissue cells. Macrophages, for example, are activated to kill the intravesicular pathogens they harbour, and B cells to secrete immunoglobulins against foreign molecules. MHC class II molecules are prevented from binding to peptides in the endoplasmic reticulum and thus MHC class II molecules bind peptides from proteins which are degraded in endosomes. They can capture peptides from pathogens that have entered the vesicular system of macrophages, or from antigens internalized by immature dendritic cells or the immunoglobulin receptors of B cells. Pathogens that accumulate in large numbers inside macrophage and dendritic cell vesicles tend to stimulate the differentiation of TH1 cells, whereas extracellular antigens tend to stimulate the production of TH2 cells. TH1 cells activate the microbicidal properties of macrophages and induce B cells to make IgG antibodies that are very effective of opsonising extracellular pathogens for ingestion by phagocytic cells, whereas TH2 cells initiate the humoral response by activating naïve B cells to secrete IgM, and induce the production of weakly opsonising antibodies such as IgG1 and IgG3 (mouse) and IgG2 and IgG4 (human) as well as IgA and IgE (mouse and human).

Epitope (also called "antigen determinant"): T cell epitopes or parts of the proteins in the context of the present invention may comprise fragments preferably having a length of about 6 to about 20 or even more amino acids, e.g. fragments as processed and presented by MHC class I molecules, preferably having a length of about 8 to about 10 amino acids, e.g. 8, 9, or 10, (or even 11, or 12 amino acids), or fragments as processed and presented by MHC class II molecules, preferably having a length of about 13 or more amino acids, e.g. 13, 14, 15, 16, 17, 18, 19, 20 or even more amino acids, wherein these fragments may be selected from any part of the amino acid sequence. These fragments are typically recognized by T cells in form of a complex consisting of the peptide fragment and an MHC molecule.

B cell epitopes are typically fragments located on the outer surface of (native) protein or peptide antigens as defined herein, preferably having 5 to 15 amino acids, more preferably having 5 to 12 amino acids, even more preferably having 6 to 9 amino acids, which may be recognized by antibodies, i.e. in their native form.

Such epitopes of proteins or peptides may furthermore be selected from any of the herein mentioned variants of such proteins or peptides. In this context antigenic determinants can be conformational or discontinuous epitopes which are composed of segments of the proteins or peptides as defined herein that are discontinuous in the amino acid sequence of the proteins or peptides as defined herein but are brought together in the three-dimensional structure or continuous or linear epitopes which are composed of a single polypeptide chain.

Vaccine: A vaccine is typically understood to be a prophylactic or therapeutic material providing at least one antigen or antigenic function. The antigen or antigenic function may stimulate the body's adaptive immune system to provide an adaptive immune response.

Antigen-providing mRNA: An antigen-providing mRNA in the context of the invention may typically be an mRNA, having at least one open reading frame that can be translated by a cell or an organism provided with that mRNA. The product of this translation is a peptide or protein that may act as an antigen, preferably as an immunogen. The product may also be a fusion protein composed of more than one immunogen, e.g. a fusion protein that consist of two or more epitopes, peptides or proteins derived from the same or different virus-proteins, wherein the epitopes, peptides or proteins may be linked by linker sequences.

Bi-/multicistronic mRNA: mRNA, that typically may have two (bicistronic) or more (multicistronic) open reading frames (ORF). An open reading frame in this context is a sequence of several nucleotide triplets (codons) that can be translated into a peptide or protein. Translation of such a mRNA yields two (bicistronic) or more (multicistronic) distinct translation products (provided the ORFs are not identical). For expression in eukaryotes such mRNAs may for example comprise an internal ribosomal entry site (IRES) sequence.

5'-CAP-Structure: A 5'-CAP is typically a modified nucleotide, particularly a guanine nucleotide, added to the 5' end of an mRNA-molecule. Preferably, the 5'-CAP is added using a 5'-5'-triphosphate linkage (also named m7GpppN). Further examples of 5'-CAP structures include glyceryl, inverted deoxy abasic residue (moiety), 4',5' methylene nucleotide, 1-(beta-D-erythrofuranosyl) nucleotide, 4'-thio nucleotide, carbocyclic nucleotide, 1,5-anhydrohexitol nucleotide, L-nucleotides, alpha-nucleotide, modified base nucleotide, threo-pentofuranosyl nucleotide, acyclic 3',4'-seco nucleotide, acyclic 3,4-dihydroxybutyl nucleotide, acyclic 3,5 dihydroxypentyl nucleotide, 3'-3'-inverted nucleotide moiety, 3'-3'-inverted abasic moiety, 3'-2'-inverted nucleotide moiety, 3'-2'-inverted abasic moiety, 1,4-butanediol phosphate, 3'-phosphoramidate, hexylphosphate, aminohexyl phosphate, 3'-phosphate, 3'phosphorothioate, phosphorodithioate, or bridging or non-bridging methylphosphonate moiety. These modified 5'-CAP structures may be used in the context of the present invention to modify the inventive mRNA sequence. Further modified 5'-CAP structures which may be used in the context of the present invention are CAP1 (methylation of the ribose of the adjacent nucleotide of m7GpppN), CAP2 (methylation of the ribose of the $2^{nd}$ nucleotide downstream of the m7GpppN), CAP3 (methylation of the ribose of the $3^{rd}$ nucleotide downstream of the m7GpppN), CAP4 (methylation of the ribose of the $4^{th}$ nucleotide downstream of the m7GpppN), ARCA (anti-reverse CAP analogue, modified ARCA (e.g. phosphothioate modified ARCA), inosine, N1-methyl-guanosine, 2'-fluoro-guanosine, 7-deaza-guanosine, 8-oxo-guanosine, 2-amino-guanosine, LNA-guanosine, and 2-azido-guanosine.

Fragments of proteins: "Fragments" of proteins or peptides in the context of the present invention may, typically, comprise a sequence of a protein or peptide as defined herein, which is, with regard to its amino acid sequence (or its encoded nucleic acid molecule), N-terminally and/or C-terminally truncated compared to the amino acid sequence of the original (native) protein (or its encoded nucleic acid molecule). Such truncation may thus occur either on the amino acid level or correspondingly on the nucleic acid level. A sequence identity with respect to such a fragment as defined herein may therefore preferably refer to the entire protein or peptide as defined herein or to the entire (coding) nucleic acid molecule of such a protein or peptide.

Fragments of proteins or peptides in the context of the present invention may furthermore comprise a sequence of a protein or peptide as defined herein, which has a length of for example at least 5 amino acids, preferably a length of at least 6 amino acids, preferably at least 7 amino acids, more preferably at least 8 amino acids, even more preferably at least 9 amino acids; even more preferably at least 10 amino acids; even more preferably at least 11 amino acids; even more preferably at least 12 amino acids; even more preferably at least 13 amino acids; even more preferably at least 14 amino acids; even more preferably at least 15 amino acids; even more preferably at least 16 amino acids; even more preferably at least 17 amino acids; even more preferably at least 18 amino acids; even more preferably at least 19 amino acids; even more preferably at least 20 amino acids; even more preferably at least 25 amino acids; even more preferably at least 30 amino acids; even more preferably at least 35 amino acids; even more preferably at least 50 amino acids; or most preferably at least 100 amino acids. For example such fragment may have a length of about 6 to about 20 or even more amino acids, e.g. fragments as processed and presented by MHC class I molecules, preferably having a length of about 8 to about 10 amino acids, e.g. 8, 9, or 10, (or even 6, 7, 11, or 12 amino acids), or fragments as processed and presented by MHC class II molecules, preferably having a length of about 13 or more amino acids, e.g. 13, 14, 15, 16, 17, 18, 19, 20 or even more amino acids, wherein these fragments may be selected from any part of the amino acid sequence. These fragments are typically recognized by T-cells in form of a complex consisting of the peptide fragment and an MHC molecule, i.e. the fragments are typically not recognized in their native form. Fragments of proteins or peptides may comprise at least one epitope of those proteins or peptides. Furthermore also domains of a protein, like the extracellular domain, the intracellular domain or the transmembrane domain and shortened or truncated versions of a protein may be understood to comprise a fragment of a protein.

Variants of proteins: "Variants" of proteins or peptides as defined in the context of the present invention may be generated, having an amino acid sequence which differs from the original sequence in one or more mutation(s), such as one or more substituted, inserted and/or deleted amino acid(s). Preferably, these fragments and/or variants have the same biological function or specific activity compared to the full-length native protein, e.g. its specific antigenic property. "Variants" of proteins or peptides as defined in the context of the present invention may comprise conservative amino acid substitution(s) compared to their native, i.e. non-mutated physiological, sequence. Those amino acid sequences as well as their encoding nucleotide sequences in particular fall under the term variants as defined herein. Substitutions in which amino acids, which originate from the same class, are exchanged for one another are called conservative substitutions. In particular, these are amino acids having aliphatic side chains, positively or negatively charged side chains, aromatic groups in the side chains or amino acids, the side chains of which can enter into hydrogen bridges, e.g. side chains which have a hydroxyl function. This means that e.g. an amino acid having a polar side chain is replaced by another amino acid having a likewise polar side chain, or, for example, an amino acid characterized by a hydrophobic side chain is substituted by another amino acid having a likewise hydrophobic side chain (e.g. serine (threonine) by threonine (serine) or leucine (isoleucine) by isoleucine (leucine)). Insertions and substitutions are possible, in particular, at those sequence positions which cause no modification to the three-dimensional structure or do not affect the binding region. Modifications to a three-dimensional structure by insertion(s) or deletion(s) can easily be determined e.g. using CD spectra (circular dichroism spectra) (Urry, 1985, Absorption, Circular Dichroism and ORD of Polypeptides, in: Modern Physical Methods in Biochemistry, Neuberger et al. (ed.), Elsevier, Amsterdam).

A "variant" of a protein or peptide may have at least 70%, 75%, 80%, 85%, 90%, 95%, 98% or 99% amino acid identity over a stretch of 10, 20, 30, 50, 75 or 100 amino acids of such protein or peptide.

Furthermore, variants of proteins or peptides as defined herein, which may be encoded by a nucleic acid molecule, may also comprise those sequences, wherein nucleotides of the encoding nucleic acid sequence are exchanged according to the degeneration of the genetic code, without leading to an alteration of the respective amino acid sequence of the protein or peptide, i.e. the amino acid sequence or at least part thereof may not differ from the original sequence in one or more mutation(s) within the above meaning.

Identity of a sequence: In order to determine the percentage to which two sequences are identical, e.g. nucleic acid sequences or amino acid sequences as defined herein, preferably the amino acid sequences encoded by a nucleic acid sequence of the polymeric carrier as defined herein or the amino acid sequences themselves, the sequences can be aligned in order to be subsequently compared to one another. Therefore, e.g. a position of a first sequence may be compared with the corresponding position of the second sequence. If a position in the first sequence is occupied by the same component (residue) as is the case at a position in the second sequence, the two sequences are identical at this position. If this is not the case, the sequences differ at this position. If insertions occur in the second sequence in comparison to the first sequence, gaps can be inserted into the first sequence to allow a further alignment. If deletions occur in the second sequence in comparison to the first sequence, gaps can be inserted into the second sequence to allow a further alignment. The percentage to which two sequences are identical is then a function of the number of identical positions divided by the total number of positions including those positions which are only occupied in one sequence. The percentage to which two sequences are identical can be determined using a mathematical algorithm. A preferred, but not limiting, example of a mathematical algorithm which can be used is the algorithm of Karlin et al. (1993), PNAS USA, 90:5873-5877 or Altschul et al. (1997), Nucleic Acids Res., 25:3389-3402. Such an algorithm is integrated in the BLAST program. Sequences which are identical to the sequences of the present invention to a certain extent can be identified by this program.

Derivative of a protein or peptide: A derivative of a peptide or protein is typically understood to be a molecule that is derived from another molecule, such as said peptide or protein. A "derivative" of a peptide or protein also encompasses fusions comprising a peptide or protein used in the present invention. For example, the fusion comprises a label, such as, for example, an epitope, e.g., a FLAG epitope or a V5 epitope. For example, the epitope is a FLAG epitope. Such a tag is useful for, for example, purifying the fusion protein.

Monocistronic mRNA: A monocistronic mRNA may typically be an mRNA, that encodes only one open reading frame. An open reading frame in this context is a sequence of several nucleotide triplets (codons) that can be translated into a peptide or protein.

Nucleic acid: The term nucleic acid means any DNA- or RNA-molecule and is used synonymous with polynucleotide. Wherever herein reference is made to a nucleic acid or nucleic acid sequence encoding a particular protein and/or peptide, said nucleic acid or nucleic acid sequence, respectively, preferably also comprises regulatory sequences allowing in a suitable host, e.g. a human being, its expression, i.e. transcription and/or translation of the nucleic acid sequence encoding the particular protein or peptide.

Peptide: A peptide is a polymer of amino acid monomers. Usually the monomers are linked by peptide bonds. The term "peptide" does not limit the length of the polymer chain of amino acids. In some embodiments of the present invention a peptide may for example contain less than 50 monomer units. Longer peptides are also called polypeptides, typically having 50 to 600 monomeric units, more specifically 50 to 300 monomeric units.

Pharmaceutically effective amount: A pharmaceutically effective amount in the context of the invention is typically understood to be an amount that is sufficient to induce an immune response.

Protein: A protein typically consists of one or more peptides and/or polypeptides folded into 3-dimensional form, facilitating a biological function.

Poly (C) sequence: A poly-(C)-sequence is typically a long sequence of cytosine nucleotides, typically about 10 to about 200 cytosine nucleotides, preferably about 10 to about 100 cytosine nucleotides, more preferably about 10 to about 70 cytosine nucleotides or even more preferably about 20 to about 50 or even about 20 to about 30 cytosine nucleotides.

A poly(C) sequence may preferably be located 3' of the coding region comprised by a nucleic acid.

Poly-A-tail: A poly-A-tail also called "3'-poly(A) tail" is typically a long sequence of adenosine nucleotides of up to about 400 adenosine nucleotides, e.g. from about 25 to about 400, preferably from about 50 to about 400, more preferably from about 50 to about 300, even more preferably from about 50 to about 250, most preferably from about 60 to about 250 adenosine nucleotides, added to the 3' end of a RNA.

Stabilized nucleic acid: A stabilized nucleic acid, typically, exhibits a modification increasing resistance to in vivo degradation (e.g. degradation by an exo- or endo-nuclease) and/or ex vivo degradation (e.g. by the manufacturing process prior to vaccine administration, e.g. in the course of the preparation of the vaccine solution to be administered). Stabilization of RNA can, e.g., be achieved by providing a 5'-CAP-Structure, a Poly-A-Tail, or any other UTR-modification. It can also be achieved by backbone-modification or modification of the G/C-content of the nucleic acid. Various other methods are known in the art and conceivable in the context of the invention.

Carrier/polymeric carrier: A carrier in the context of the invention may typically be a compound that facilitates transport and/or complexation of another compound. Said carrier may form a complex with said other compound. A polymeric carrier is a carrier that is formed of a polymer.

Cationic component: The term "cationic component" typically refers to a charged molecule, which is positively charged (cation) at a pH value of typically about 1 to 9, preferably of a pH value of or below 9 (e.g. 5 to 9), of or below 8 (e.g. 5 to 8), of or below 7 (e.g. 5 to 7), most preferably at physiological pH values, e.g. about 7.3 to 7.4. Accordingly, a cationic peptide, protein or polymer according to the present invention is positively charged under physiological conditions, particularly under physiological salt conditions of the cell in vivo. A cationic peptide or protein preferably contains a larger number of cationic amino acids, e.g. a larger number of Arg, His, Lys or Om than other amino acid residues (in particular more cationic amino acids than anionic amino acid residues like Asp or Glu) or contains blocks predominantly formed by cationic amino acid residues. The definition "cationic" may also refer to "polycationic" components.

Vehicle: An agent, e.g. a carrier, that may typically be used within a pharmaceutical composition or vaccine for facilitating administering of the components of the pharmaceutical composition or vaccine to an individual.

3'-untranslated region (3'UTR): A 3'UTR is typically the part of an mRNA which is located between the protein coding region (i.e. the open reading frame) and the poly(A) sequence of the mRNA. A 3'UTR of the mRNA is not translated into an amino acid sequence. The 3'UTR sequence is generally encoded by the gene which is transcribed into the respective mRNA during the gene expression process. The genomic sequence is first transcribed into pre-mature mRNA, which comprises optional introns. The pre-mature mRNA is then further processed into mature mRNA in a maturation process. This maturation process comprises the steps of 5'-Capping, splicing the pre-mature mRNA to excise optional introns and modifications of the 3'-end, such as polyadenylation of the 3'-end of the pre-mature mRNA and optional endo- or exonuclease cleavages etc. In the context of the present invention, a 3'UTR corresponds to the sequence of a mature mRNA which is located 3' to the stop codon of the protein coding region, preferably immediately 3' to the stop codon of the protein coding region, and which extends to the 5'-side of the poly(A) sequence, preferably to the nucleotide immediately 5' to the poly(A) sequence. The term "corresponds to" means that the 3'UTR sequence may be an RNA sequence, such as in the mRNA sequence used for defining the 3'UTR sequence, or a DNA sequence which corresponds to such RNA sequence. In the context of the present invention, the term "a 3'UTR of a gene", such as "a 3'UTR of an albumin gene", is the sequence which corresponds to the 3'UTR of the mature mRNA derived from this gene, i.e. the mRNA obtained by transcription of the gene and maturation of the pre-mature mRNA. The term "3'UTR of a gene" encompasses the DNA sequence and the RNA sequence of the 3'UTR.

5'-untranslated region (5'UTR): A 5'-UTR is typically understood to be a particular section of messenger RNA (mRNA). It is located 5' of the open reading frame of the mRNA. Typically, the 5'UTR starts with the transcriptional start site and ends one nucleotide before the start codon of the open reading frame. The 5'-UTR may comprise elements for controlling gene expression, also called regulatory elements. Such regulatory elements may be, for example, ribosomal binding sites or a 5'-Terminal Oligopyrimidine Tract. The 5'UTR may be posttranscriptionally modified, for example by addition of a 5'-CAP. In the context of the present invention, a 5'UTR corresponds to the sequence of a mature mRNA which is located between the 5'-CAP and the start codon. Preferably, the 5'UTR corresponds to the sequence which extends from a nucleotide located 3' to the 5'-CAP, preferably from the nucleotide located immediately 3' to the 5'-CAP, to a nucleotide located 5' to the start codon of the protein coding region, preferably to the nucleotide located immediately 5' to the start codon of the protein coding region. The nucleotide located immediately 3' to the 5'-CAP of a mature mRNA typically corresponds to the transcriptional start site. The term "corresponds to" means that the 5'UTR sequence may be an RNA sequence, such as in the mRNA sequence used for defining the 5'UTR sequence, or a DNA sequence which corresponds to such RNA sequence. In the context of the present invention, the term "a 5'UTR of a gene", such as "a 5'UTR of a TOP gene", is the sequence which corresponds to the 5'UTR of the mature mRNA derived from this gene, i.e. the mRNA obtained by transcription of the gene and maturation of the pre-mature mRNA. The term "5'UTR of a gene" encompasses the DNA sequence and the RNA sequence of the 5'UTR.

5'Terminal Oligopyrimidine Tract (TOP): The 5'terminal oligopyrimidine tract (TOP) is typically a stretch of pyrimidine nucleotides located at the 5' terminal region of a nucleic acid molecule, such as the 5' terminal region of certain mRNA molecules or the 5' terminal region of a functional entity, e.g. the transcribed region, of certain genes. The sequence starts with a cytidine, which usually corresponds to the transcriptional start site, and is followed by a stretch of usually about 3 to 30 pyrimidine nucleotides. For example, the TOP may comprise 3, 4, 5, 6, 7, 8, 9, 10, 11, 12, 13, 14, 15, 16, 17, 18, 19, 20, 21, 22, 23, 24, 25, 26, 27, 28, 29, 30 or even more nucleotides. The pyrimidine stretch and thus the 5' TOP ends one nucleotide 5' to the first purine nucleotide located downstream of the TOP. Messenger RNA that contains a 5'terminal oligopyrimidine tract is often referred to as TOP mRNA. Accordingly, genes that provide such messenger RNAs are referred to as TOP genes. TOP sequences have, for example, been found in genes and mRNAs encoding peptide elongation factors and ribosomal proteins.

TOP motif: In the context of the present invention, a TOP motif is a nucleic acid sequence which corresponds to a 5'TOP as defined above. Thus, a TOP motif in the context of the present invention is preferably a stretch of pyrimidine nucleotides having a length of 3-30 nucleotides. Preferably, the TOP-motif consists of at least 3 pyrimidine nucleotides, preferably at least 4 pyrimidine nucleotides, preferably at least 5 pyrimidine nucleotides, more preferably at least 6 nucleotides, more preferably at least 7 nucleotides, most preferably at least 8 pyrimidine nucleotides, wherein the stretch of pyrimidine nucleotides preferably starts at its 5'end with a cytosine nucleotide. In TOP genes and TOP mRNAs, the TOP-motif preferably starts at its 5'end with the transcriptional start site and ends one nucleotide 5' to the first purin residue in said gene or mRNA. A TOP motif in the sense of the present invention is preferably located at the 5'end of a sequence which represents a 5'UTR or at the 5'end of a sequence which codes for a 5'UTR. Thus, preferably, a stretch of 3 or more pyrimidine nucleotides is called "TOP motif" in the sense of the present invention if this stretch is located at the 5'end of a respective sequence, such as the inventive mRNA, the 5'UTR element of the inventive mRNA, or the nucleic acid sequence which is derived from the 5'UTR of a TOP gene as described herein. In other words, a stretch of 3 or more pyrimidine nucleotides which is not located at the 5'-end of a 5'UTR or a 5'UTR element but anywhere within a 5'UTR or a 5'UTR element is preferably not referred to as "TOP motif".

TOP gene: TOP genes are typically characterised by the presence of a 5' terminal oligopyrimidine tract. Furthermore, most TOP genes are characterized by a growth-associated translational regulation. However, also TOP genes with a tissue specific translational regulation are known. As defined above, the 5'UTR of a TOP gene corresponds to the sequence of a 5'UTR of a mature mRNA derived from a TOP gene, which preferably extends from the nucleotide located 3' to the 5'-CAP to the nucleotide located 5' to the start codon. A 5'UTR of a TOP gene typically does not comprise any start codons, preferably no upstream AUGs (uAUGs) or upstream open reading frames (uORFs). Therein, upstream AUGs and upstream open reading frames are typically understood to be AUGs and open reading frames that occur 5' of the start codon (AUG) of the open reading frame that should be translated. The 5'UTRs of TOP genes are generally rather short. The lengths of 5'UTRs of TOP genes may vary between 20 nucleotides up to 500 nucleotides, and are typically less than about 200 nucleotides, preferably less than about 150 nucleotides, more preferably less than about 100 nucleotides. Exemplary 5'UTRs of TOP genes in the sense of the present invention are the nucleic acid sequences extending from the nucleotide at position 5 to the nucleotide located immediately 5' to the start codon (e.g. the ATG) in the sequences according to SEQ ID Nos. 1-1363, SEQ ID NO. 1395, SEQ ID NO. 1421 and SEQ ID NO. 1422 of the patent application WO2013/143700 or homologs or variants thereof, whose disclosure is incorporated herewith by reference. In this context a particularly preferred fragment of a 5'UTR of a TOP gene is a 5'UTR of a TOP gene lacking the 5'TOP motif. The term '5'UTR of a TOP gene' preferably refers to the 5'UTR of a naturally occurring TOP gene.

Fragment of a nucleic acid sequence, particularly an mRNA: A fragment of a nucleic acid sequence consists of a continuous stretch of nucleotides corresponding to a continuous stretch of nucleotides in the full-length nucleic acid sequence which is the basis for the nucleic acid sequence of the fragment, which represents at least 20%, preferably at least 30%, more preferably at least 40%, more preferably at least 50%, even more preferably at least 60%, even more preferably at least 70%, even more preferably at least 80%, and most preferably at least 90% of the full-length nucleic acid sequence. Such a fragment, in the sense of the present invention, is preferably a functional fragment of the full-length nucleic acid sequence.

Variant of a nucleic acid sequence, particularly an mRNA: A variant of a nucleic acid sequence refers to a variant of nucleic acid sequences which forms the basis of a nucleic acid sequence. For example, a variant nucleic acid sequence may exhibit one or more nucleotide deletions, insertions, additions and/or substitutions compared to the nucleic acid sequence from which the variant is derived. Preferably, a variant of a nucleic acid sequence is at least 40%, preferably at least 50%, more preferably at least 60%, more preferably at least 70%, even more preferably at least 80%, even more preferably at least 90%, most preferably at least 95% identical to the nucleic acid sequence the variant is derived from. Preferably, the variant is a functional variant. A "variant" of a nucleic acid sequence may have at least 70%, 75%, 80%, 85%, 90%, 95%, 98% or 99% nucleotide identity over a stretch of 10, 20, 30, 50, 75 or 100 nucleotide of such nucleic acid sequence.

Homolog of a nucleic acid sequence: The term "homolog" of a nucleic acid sequence refers to sequences of other species than the particular sequence. It is particular preferred that the nucleic acid sequence is of human origin and therefore it is preferred that the homolog is a homolog of a human nucleic acid sequence.

Jet injection: The term "jet injection", as used herein, refers to a needle-free injection method, wherein a fluid containing at least one inventive mRNA sequence and, optionally, further suitable excipients is forced through an orifice, thus generating an ultra-fine liquid stream of high pressure that is capable of penetrating mammalian skin and, depending on the injection settings, subcutaneous tissue or muscle tissue. In principle, the liquid stream forms a hole in the skin, through which the liquid stream is pushed into the target tissue. Preferably, jet injection is used for intradermal, subcutaneous or intramuscular injection of the mRNA sequence according to the invention. In a preferred embodiment, jet injection is used for intramuscular injection of the mRNA sequence according to the invention. In a further preferred embodiment, jet injection is used for intradermal injection of the mRNA sequence according to the invention.

The present invention is based on the surprising finding of the present inventors that an mRNA sequence comprising a coding region, encoding at least one antigenic peptide or protein of Rabies virus induces antigen-specific immune responses which neutralize Rabies virus particles and therefore prevent Rabies virus infections. It was very surprising for the inventors that the inventive mRNA sequence induces at least the same immune responses than a licensed rabies vaccine which consists of the whole inactive rabies virus. Even more surprisingly the inventive mRNA sequence coding for an antigenic protein of Rabies virus induced higher antigen-specific CD4+-T cells than a licensed rabies vaccine.

Furthermore, the inventors surprisingly found that the mRNA-based rabies vaccine according to the invention was biologically active after storage at 40° C. for 6 months and even after storage at 60° C. for 1 month. Therefore the mRNA-based rabies vaccine according to the invention would be an attractive option for postexposure prophylaxis in developing countries, since it can be stored at ambient temperature, compared to the licensed vaccines which have to be stored between +2 and +8° C.

In summary the inventive mRNA sequence comprising a coding region encoding at least one antigenic peptide or protein of Rabies virus could contribute to affordable, readily available, temperature-stable rabies vaccines, particularly for preexposure and postexposure rabies prophylaxis for the developed and developing world.

Additionally, the mRNA sequence according to the invention enables rapid and rational vaccine design with flexibility, speed and scalability of production probably exceeding those of current virus-based technologies.

In this context it is particularly preferred that the inventive mRNA sequence comprises a coding region, encoding at least one antigenic peptide or protein derived from the glycoprotein G (RAV-G), the nucleoprotein (RAV-N), the posphoprotein (RAV-P), the matrix protein (RAV-M), or the RNA polymerase (RAV-L) of Rabies virus or a fragment, variant or derivative thereof.

The coding region of the inventive mRNA sequence according to the first aspect of the present invention may occur as a mono-, di-, or even multicistronic mRNA, i.e. an mRNA sequence which carries the coding sequences of one, two or more proteins or peptides. Such coding sequences in di-, or even multicistronic mRNAs may be separated by at least one internal ribosome entry site (IRES) sequence, e.g. as described herein or by signal peptides which induce the cleavage of the resulting polypeptide which comprises several proteins or peptides.

According to the first aspect of the present invention, the inventive mRNA sequence comprises a coding region, encoding at least one antigenic peptide or protein derived from the glycoprotein G (RAV-G), the nucleoprotein (RAV-N), the posphoprotein (RAV-P), the matrix protein (RAV-M), or the RNA polymerase (RAV-L) of Rabies virus or a fragment, variant or derivative thereof.

In a particularly preferred embodiment of the first aspect of the invention the inventive mRNA sequence comprises a coding region, encoding at least one antigenic peptide or protein derived from the glycoprotein G (RAV-G) of Rabies virus or a fragment, variant or derivative thereof.

In this context the amino acid sequence of the at least one antigenic peptide or protein may be selected from any peptide or protein derived from the glycoprotein G (RAV-G), the nucleoprotein N (RAV-N), the posphoprotein P (RAV-P), the matrix protein M (RAV-M), and the RNA polymerase L (RAV-L) of any Rabies virus isolate or a fragment, variant or derivative thereof or from any synthetically engineered rabies peptide or protein.

In a particularly preferred embodiment the full-length protein of the glycoprotein G (RAV-G), the nucleoprotein N (RAV-N), the posphoprotein P (RAV-P), the matrix protein M (RAV-M), or the RNA polymerase L (RAV-L) is encoded by the coding region comprised in the inventive mRNA.

In a further particularly preferred embodiment a fragment comprising at least one epitope of the glycoprotein G (RAV-G), the nucleoprotein N (RAV-N), the posphoprotein P (RAV-P), the matrix protein M (RAV-M), or the RNA polymerase L (RAV-L) is encoded by the coding region comprised in the inventive mRNA.

Particularly preferred are the amino acid sequences of a Rabies vaccine strain, preferably of the Pasteur vaccine strain according to the NCBI accession No. M13215:

Glycoprotein G (RAV-G) of Pasteur Vaccine Strain:

Amino acid sequence according to SEQ ID No. 1:
MVPQALLFVPLLVFPLCFGKFPIYTIPDKLGPWSPIDIHHLSCPNNLVVE

DEGCTNLSGFSYMELKVGYISAIKMNGFTCTGVVTEAETYTNFVGYVTTT

FKRKHFRPTPDACRAAYNWKMAGDPRYEESLHNPYPDYHWLRTVKTTKES

LVIISPSVADLDPYDRSLHSRVFPGGNCSGVAVSSTYCSTNHDYTIWMPE

NPRLGMSCDIFTNSRGKRASKGSETCGFVDERGLYKSLKGACKLKLCGVL

GLRLMDGTWVAMQTSNETKWCPPGQLVNLHDFRSDEIEHLVVEELVKKRE

ECLDALESIMTTKSVSFRRLSHLRKLVPGFGKAYTIFNKTLMEADAHYKS

VRTWNEIIPSKGCLRVGGRCHPHVNGVFFNGIILGPDGNVLIPEMQSSLL

QQHMELLVSSVIPLMHPLADPSTVFKNGDEAEDFVEVHLPDVHERISGVD

LGLPNWGKYVLLSAGALTALMLIIFLMTCWRRVNRSEPTQHNLRGTGREV

SVTPQSGKIISSWESYKSGGETGL

Nucleoprotein N (RAV-N) of Pasteur Vaccine Strain:

Amino acid sequence according to SEQ ID No. 2:
MDADKIVFKVNNQVVSLKPEIIVDQYEYKYPAIKDLKKPCITLGKAPDLN

KAYKSVLSCMSAAKLDPDDVCSYLAAAMQFFEGTCPEDWTSYGIVIARKG

DKITPGSLVEIKRTDVEGNWALTGGMELTRDPTVPEHASLVGLLLSLYRL

SKISGQSTGNYKTNIADRIEQIFETAPFVKIVEHHTLMTTHKMCANWSTI

PNFRFLAGTYDMFFSRIEHLYSAIRVGTVVTAYEDCSGLVSFTGFIKQIN

LTAREAILYFFHKNFEEEIRRMFEPGQETAVPHSYFIHFRSLGLSGKSPY

SSNAVGHVFNLIHFVGCYMGQVRSLNATVIAACAPHEMSVLGGYLGEEFF

GKGTFERRFFRDEKELQEYEAAELTKTDVALADDGTVNSDDEDYFSGETR

SPEAVYTRIIMNGGRLKRSHIRRYVSVSSNHQARPNSFAEFLNKTYSSDS

Phosphoprotein P (Also Named M1) (RAV-P) of Pasteur Vaccine Strain:

Amino acid sequence according to SEQ ID No. 3:
MSKIFVNPSAIRAGLADLEMAEETVDLINRNIEDNQAHLQGEPIEVDNLP

EDMGRLHLDDGKSPNPGEMAKVGEGKYREDFQMDEGEDPSLLFQSYLDNV

GVQIVRQIRSGERFLKIWSQTVEEIISYVAVNFPNPPGKSSEDKSTQTTG

RELKKETTPTPSQRESQSSKARMAAQTASGPPALEWSATNEEDDLSVEAE

IAHQIAESFSKKYKFPSRSSGILLYNFEQLKMNLDDIVKEAKNVPGVTRL

ARDGSKLPLRCVLGWVALANSKKFQLLVESNKLSKIMQDDLNRYTSC

Matrix Protein M (Also Named M2) (RAV-M) of Pasteur Vaccine Strain:

Amino acid sequence according to SEQ ID No. 4:
MNFLRKIVKNCRDEDTQKPSPVSAPLDDDDLWLPPPEYVPLKELTSKKNR

RNFCINGGVKVCSPNGYSFGILRHILRSFDEIYSGNHRMVGLVKVVIGLA

LSGAPVPEGMNWVYKLRRTLIFQWADSRGPLEGEELEYSQEITWDDNTEF

VGLQIRVSAKQCHIRGRIWCINMNSRAGQLWSDMSLQTQRSEEDKDSSLL

LE

RNA Polymerase L (RAV-L) of Pasteur Vaccine Strain:

Amino acid sequence according to SEQ ID No. 5:
MLDPGEVYDDPIDPIELEAEPRGTPTPVPNILRNSDYNLNSPLIEDPARLM
LEWLKTGNRPYRMTLTDNCSRSFRVLKDYFKKVDLGSLKVGGMAAQSMIS
LWLYGAHSESNRSRRCITDLAHFYSKSSPIEKLLNLTLGNRGLRIPPEGV
LSCLERVDYDNAFGRYLANTYSSYLFFHVITLYMNALDWDEEKTILALWK
DLTSVDIGKDLVKFKDQIWGLLIVTKDFVYSQSSNCLFDRNYTLMLKDLF
LSRFNSLMVLLSPPEPRYSDDLISQLCQLYIAGDQVLSMCGNSGYEVIKI
LEPYVVNSLVQRAEKFRPLIHSLGDFPVFIKDKVSQLEETFGSCARRFFR
ALDQFDNIHDLVFVYGCYRHWGHPYIDYRKGLSKLYDQVHIKKVIDKSYQ
ECLASDLARRILRWGFDKYSKWYLDSRFLARDHPLTPYIKTQTWPPKHIV
DLVGDTWHKLPITQIFEIPESMDPSEILDDKSHSFTRTRLASWLSENRGG
PVPSEKVIITALSKPPVNPREFLKSIDLGGLPDEDLIIGLKPKERELKIE
GRFFALMSWNLRLYFVITEKLLANYILPLFDALTMTDNLNKVFKKLIDRV
TGQGLLDYSRVTYAPHLDYEKWNNHQRLESTEDVFSVLDQVFGLKRVFSR
THEFFQKSWIYYSDRSDLIGLREDQIYCLDASNGPTCWNGQDGGLEGLRQ
KGWSLVSLLMIDRESQIRNTRTKVLAQGDNQVLCPTYMLSPGLSQEGLLY
ELESISRNAFSIYRAVEEGASKLGLIIKKEETMCSYDFLIYGKTPLFRGN
ILVPESKRWARVSCVSNDQIVNLANIMSTVSTNALTVAQHSQSLIKPMRD
FLLMSVQAVFHYLLFSPILKGRVYKILSAEGESFLLAMSRIIYLDPSLGG
VSGMSLGRFHIRQFSDPVSEGLSFWREIWLSSHESWIHALCQEAGNPDLG
ERTLESFTRLLEDPTTLNIRGGASPTILLKDAIRKALYDEVDKVENSEFR
EAILLSKTHRDNFILFLTSVEPLFPRFLSELFSSSFLGIPESIIGLIQNS
RTIRRQFRKSLSKTLEESFYNSEIHGISRMTQTPQRVGGVWPCSSERADL
LREISWGRKVVGTTVPHPSEMLGLLPKSSISCTCGATGGGNPRVSVSVLP
SFDQSFFCTGPLKGYLGSSTSMSTQLFHAWEKVTNVHVVKRALSLKESIN
WFITRDSNLAQTLIRNIVSLTGPDFPLEEAPVFKRTGSALHRFKSARYSE
GGYSSVCPNLLSHISVSTDTMSDLTQDGKNYDFMFQPLMLYAQTWTSELV
QRDTRLRDSTFHWHLQCNRCVRPIDDVTLETSQIFEFPDVSKRISRMVSG
AVPHFQRLPDIRLRPGDFESLSGREKSHHIGSAQGLLYSILVAIHDSGYN
DGTIFPVNIYGKVSPRDYLRGLARGVLIGSSICFLTRMTNININRPLELI
SGVISYILLRLDNHPSLYIMLREPSFREEIFSIPQKIPAAYPTTMKEGNR
SILCYLQHVLRYEREVITASPENDWLWIFSDFRSAKMTYLTLITYQSHLL
LQRVERNLSKSMRDNLRQLSSLMRQVLGGHGEDTLESDDNIQRLLKDSLR
RTRWVDQEVRHAARTMTGDYSPNKKVSRKVGCSEWVCSAQQVAVSTSANP
APVSELDIRALSKRFQNPLISGLRVVQWATGAHYKLKPILDDLNVFPSLC
LVVGDGSGGISRAVLNMFPDAKLVFNSLLEVNDLMASGTHPLPPSAIMRG
GNDIVSRVIDFDSIWEKPSDLRNLATWKYFQSVQKQVNMSYDLIICDAEV
TDIASINRITLLMSDFALSIDGPLYLVFKTYGTMLVNPNYKAIQHLSRAF
PSVTGFITQVTSSFSSELYLRFSKRGKFFRDAEYLTSSTLREMSLVLFNC
SSPKSEMQRARSLNYQDLVRGFPEEIISNPYNEMIITLIDSDVESFLVHK MVDDLELQRGTLSKVAIIIAIMIVFSNRVFNVSKPLTDPLFYPPSDPKIL
RHFNICCSTMMYLSTALGDVPSFARLHDLYNRPITYYFRKQVILGNVYLS
WSWSNDTSVFKRVACNSSLSLSSHWIRLIYKIVKTTRLVGSIKDLSGEVE
RHLHRYNRWITLENIRSRSSLLDYSCLCIGYSWKPAHAKTLV Additionally particularly preferred are the amino acid sequences of the Flury-LEP vaccine strain (used for Rabipur®) according to the NCBI accession No. GU565703:

Glycoprotein G (RAV-G) of Flury-LEP Vaccine Strain:

Amino acid sequence according to SEQ ID No. 6:
MVPQVLLFVPLLGFSLCFGKFPIYTIPDKLGPWSPIDIHHLSCPNNLVVE
DEGCTNLSEFSYMELKVGYISAIKVNGFTCTGVVTEAETYTNFVGYVTTT
FKRKHFRPTPDACRAAYNWKMAGDPRYEESLHNPYPDYHWLRTVKTTKES
LVIISPSVTDLDPYDKSLHSRVFPGGNCSGITVSSTYCSTNHDYTIWMPE
NLRLGTSCDIFTNSRGKRASKGGKTCGFVDERGLYKSLKGACKLKLCGVL
GLRLMDGTWVAMQTSDETKWCPPGQLVNLHDFRSDEIEHLVVEELVKKRE
ECLDALESIMTTKSVSFRRLSHLRKLVPGFGKAYTIFNKTLMEADAHYKS
VRTWNEIIPSKGCLRVGGRCHPHVNGVFFNGIILGSDGHVLIPEMQSSLL
QQHMELLESSVIPLMHPLADPSTVFKDGDEVEDFVEVHLPDVHEQVSGVE
LGLPNWGKYVLMIAGALIALMLIIFLMTCCRRVNRPESTQSSLGETGRNV
SVTSQSGKVISSWESYKSGGETRL Nucleoprotein N (Rav N) of Flury-LEP Vaccine Strain:

Amino acid sequence according to SEQ ID No. 7:
MDADKIVFKVNNQVVSLKPEIIVDQYEYKYPAIKDLKKPCITLGKAPDLN
KAYKSVLSGMNAAKLDPDDVCSYLAAAMQFFEGTCPEDWTSYGILIARKG
DKITPDSLVEIKRTDVEGNWALTGGMELTRDPTVSEHASLVGLLLSLYRL
SKISGQNTGNYKTNIADRIEQIFETAPFVKIVEHHTLMTTHKMCANWSTI
PNFRFLAGTYDMFFSRIEHLYSAIRVGTVVTAYEDCSGLVSFTGFIKQIN
LTAREAILYFFHKNFEEEIRRMFEPGQETAVPHSYFIHFRSLGLSGKSPY
SSNAVGHVFNLIHFVGCYMGQVRSLNATVIAACAPHEMSVLGGYLGEEFF
GKGTFERRFFRDEKELQEYEAAELTKTDVALADDGTVNSDDEDYFSGETR
SPEAVYTRIMMNGGRLKRSHIRRYVSVSSNHQARPNSFAEFLNKTYSSDS Phosphoprotein P (Rav P) of Flury-LEP Vaccine Strain:

Amino acid sequence according to SEQ ID No. 8:
MSKIFVNPSAIRAGLADLEMAEETVDLINRNIEDNQAHLQGEPIEVDNLP
EDMRQFHLGDEKLSNLGEMVRVGEGKYREDFQMDEGEDPNLLFQSYLDNV
GVQIVRQMRSGERFLKIWSQTVEEIISYVTVNFPNPPGRSSEDKSTQTTG
RELKKETTSTLSQRESQPSKAGMVAQVASGPPSLEWSATNEEDDLSVEAE
IAHQIAESFSKKYKFPSRSSGIFLYNFEQLEMNLDDIVKEAKNVPGVTRL
AHDGSKIPLRCVLGWVALANSKKFQLIVEADKLSKIMQDDLDRYTSC Matrix Protein M (Rav M) of Flury-LEP Vaccine Strain:

Amino acid sequence according to SEQ ID No. 9:
MNFLCKIVKNCRDEDTQKPSPVSAPPDGDDLWLPPPEYVPLKELTSKKNM

RNFCINGEVKVCSPNGYSFRILRHILRSFDEIYSGNHRMIGLVKVVIGLA

LSGAPVPEGMNWVYKLRRTLIFQWADSRGPLEGEELEHSQEITWDDDTEF

VGLQMRVSARQCHIQGRIWCINMNSRACQLWSDMSLQTQRSEEDKDSSLL

LE

RNA Polymerase L (Rav L) of Flury-LEP Vaccine Strain:

Amino acid sequence according to SEQ ID No. 10:
MLDPGEVYDDPIDPIESEAEPRGTPTVPNILRNSDYNLNSPLIEDSAKLM

LEWLKTGNRPYRMTLTDNCSRSYKVLKDYFKKVDLGSLKVGGTAAQSMIS

LWLYGAHSESNRSRRCITDLAHFYSKSSPIEKLLNCTLGNRGLRIPPEGV

LSCLERVDYDKAFGRYLANTYSSYLFFHVITLYMNALDWEEEKTILALWK

DLTSVDTGKDLVKFKDQIWGLLVVTKDFVYSQSSNCLFDRNYTLMLKDLF

LSRFNSLMILLSPPEPRYSDDLISQLCQLYIAGDQVLSLCGNSGYEVIKI

LEPYVVNSLVQRAEKFRPLIHSLGDFPMFIKDKVNQLEGTFGPSAKRFFR

VLDQFDNIHDLVFVYGCYRHWGHPYIDYRKGLSKLYDQVHIKKVIDKSYQ

ECLASDLARRILRWGFDKYSKWYLDSRFLALDHPLAPYIKTQTWPPKHIV

DLVGDTWHKLPITQIFEIPESMDPSEILDDKSHSFTRTRLASWLSENRGG

PVPSEKVIITALSKPPVNPREFLKSIDLGGLPDDDLIIGLRPKERELKIE

GRFFALMSWNLRLYFVITEKLLANYILPLFDALTMTDNLNKVFKKLIDRV

TGQGLLDYSRVTYAFHLDYEKWNNHQRLESTEDVFSVLDQVFGLKRVFSR

THEFFQKSWIYYSDRSDLIGLREDQIYCLDMSNGPTCWNGQDGGLEGLRQ

KGWSLVSLLMIDRESQTRNTRTKILAQGDNQVLCPTYMLSPGLSQEGLLY

ELESISRNALSIYRAIEEGASKLGLIIKKEETMCSYDFLIYGKTPLFRGN

ILVPESKRWARVSCISNDQIVNLANIMSTVSTNALTVAQHSQSLIKPMRD

FLLMSVQAVFHYLLFSPILKGRVYKILSAEGESFLLAMSRIIYLDPSLGG

VSGMSLGRFHIRQFSDPVSEGLSFWREIWLSSHESWIHALCQEAGNPDLG

ERTLESFTRLLEDPTTLNIKGGASPTILLKDAIRKALYDEVDKVENSEFR

EAILLSKTHRDNFILFLKSVEPLFPRFLSELFSSSFLGIPESIIGLIQNS

RTIRRQFRKSLSRTLEESFYNSEIHGINRMTQTPQRVGRVWPCSSERADL

LREISWGRKVVGTTVPHPSEMLGLLPKSSISCTCGATGGGNPRVSVSVLP

SFDQSFFSRGPLKGYLGSSTSMSTQLFHAWEKVTNVHVVKRAISLKESIN

WFINRNSNLAQTLIRNIMSLTGPDFPLEEAPVFKRTGSALHRFKSARYSE

GGYSSVCPNLLSHISVSTDTMSDLTQDGKNYDFMFQPLMLYAQTWTSELV

QRDTRLRDSTFHWHLRCNRCVRPIEDITLETSQIFEFPDVSKRISRMVSG

AVPHFQKLPDIRLRPGDFESLSGREKSRHIGSAQGLLYSILVAIHDSGYN

DGTIFPVNIYGKVSPRDYLRGLARGILIGSSICFLTRMTNINIKRPLELI

SGVISYILLRLDNHPSLYIMLREPSLRGEIFSIPQKIPAAYPTTMKEGNR

SILCYLQHVLRYEREVITASPENDWLWIFSDFRSAKMTYLTLITYQSHLL

LQRVERNLSKSMRATLRQMGSLMRQVLGGHGEDTLESDDDIQRLLKDSLR

RTRWVDQEVRHAARTMSGDYSPNKRVSRKAGCSEWVCSAQQVAVSTSANP

APVSELDIRALSKRFQNPLISGLRVVQWATGAHYKLKPILDDLNVFPSLC

LVVGDGSGGISRAVLNMFPDSKLVFNSLLEVNDLMASGTHPLPPSAIMSG

GDDIISRVIDFDSIWEKPSDLRNLATWRYFQSVQKQVNMSYDLIVCDAEV

TDIASINRITLLMSDFALSIDGPLYLVFKTYGTMLVNPDYKAIQHLSRAF

PSVTGFITQVTSSFSSELYLRFSKRGKFFRDAEYLTSSTLREMSLVLFNC

SSPKSEMQRARSLNYQDLVRGFPEEIISNPYNEMIITLIDSDVESFLVHK

MVDDLELQRGTLSKVAIIISIMIVFSNRVFNISKPLTDPLFYPPSDPKIL

RHFNICCSTMMYLSTALGDVPSFARLHDLYNRPITYYFRKQVIRGNIYLS

WSWSDDTPVFKRVACNSSLSLSSHWIRLIYKIVKTTRLVGSIEDLSGEVE

RHLHGYNRWITLEDIRSRSSLLDYSCL

In the context of the invention additionally to the here disclosed amino acid sequences according to SEQ ID Nos. 1-10 also amino acid sequences of different Rabies virus isolates can be used according to the invention and are incorporated herewith. These different Rabies virus isolates show preferably an identity of at least 70%, more preferably of at least 80% and most preferably of at least 90% with the amino acid sequences according to SEQ ID Nos. 1-10.

Examples for such different Rabies virus isolates are:

Rabies virus strains according to the NCBI Accession Nos. JQ730682, AF499686, AB569299, AB839170, AB781935, FJ959397, AB362483, EF206720, EF206718, EF206717, EF206715, EF206714, EF206713, EF206712, EF206711, EF206710, EF206709, EF206708, EF206707, EU182346, HM535790, GQ918139, EU877071, EU877070, EU877069, EU182347, M31046, EU877068, EU877067, EF542830, AB839169, JQ647510, KC169986, JX088694, JQ730682, JN609295, JN234411, HQ317918, EF206719, EF564174, EU643590, JQ946087, FJ913470 HQ891318, AB645847, AB569299, AY705373, GU565704, GU565703, FJ577895, JX276550, FJ866836, FJ866835, DQ875051, DQ875050, AB128149, AB009663, AB044824, JQ944709, EU345004, EU345003, EU345002, AB608731, EF564173, JQ423952, AB618037, AB618036, AB618035, AB618034, AB618033, AB618032, AB085828, M13215, M21634, AB247437, AB247436, AB247435, AB247434, AB247433, AB247432, D42112, AB247430, and AB247431.

Furthermore in this context the coding region encoding at least one antigenic peptide or protein derived from the glycoprotein G (RAV-G), the nucleoprotein N (RAV-N), the posphoprotein P (RAV-P), the matrix protein M (RAV-M), or the RNA polymerase L (RAV-L) of Rabies virus or a fragment, variant or derivative thereof, may be selected from any nucleic acid sequence comprising a coding region derived from any Rabies virus isolate or a fragment or variant thereof.

Particularly preferred are the wild type mRNA sequences of the coding regions of a Rabies virus vaccine strain, preferably of the Pasteur vaccine strain according to the NCBI accession No. M13215.

Glycoprotein G (Rav G) of Pasteur Vaccine Strain:

```
Wild type mRNA sequence of the coding region
according to SEQ ID No. 11:
aug guu ccu cag gcu cuc cug uuu gua ccc cuu cug guu uuu cca uug ugu uuu ggg aaa uuc ccu auu uac acg aua cca gac aag cuu ggu ccc ugg agc ccg auu gac aua cau cac cuc agc ugc cca aac aau uug gua gug gag gac gaa gga ugc acc aac cug uca ggg uuc ucc uac aug gaa cuu aaa guu gga uac auc uca gcc aua aaa aug aac ggg uuc acu ugc aca ggc guu gug acg gag gcu gaa acc uac acu aac uuc guu ggu uau guc aca acc acg uuc aaa aga aag cau uuc cgc cca aca cca gau gca ugu aga gcc gcg uac aac ugg aag aug gcc ggu gac ccc aga uau gaa gag ucu cua cac aau ccg uac ccu gac uac cac ugg cuu cga acu gua aaa acc acc aag gag ucu cuc guu auc aua ucu cca agu gug gca gau uug gac cca uau gac aga ucc cuu cac ucg agg guc uuc ccu ggc ggg aau ugc uca gga gua gcg gug ucu ucu acc uac ugc ucc acu aac cac gau uac acc auu ugg aug ccc gag aau ccg aga cua ggg aug ucu ugu gac auu uuu acc aau agu aga ggg aag aga gca ucc aaa ggg agu gag acu ugc ggc uuu gua gau gaa aga ggc cua uau aag ucu uua aaa gga gca ugc aaa cuc aag uua ugu gga guu cua gga cuu aga cuu aug gau gga aca ugg guc gcg aug caa aca uca aau gaa acc aaa ugg ugc ccu ccc ggu cag uug gug aau uug cac gac uuu cgc uca gac gaa auu gag cac cuu guu gua gag gag uug guc aag aag aga gag gag ugu cug gau gca cua gag ucc auc aug acc acc aag uca gug agu uuc aga cgu cuc agu cau uua aga aaa cuu guc ccu ggg uuu gga aaa gca uau acc aua uuc aac aag acc uug aug gaa gcc gau gcu cac uac aag uca guc aga acu ugg aau gag auc auc ccu uca aaa ggg ugu uua aga guu ggg ggg agg ugu cau ccu cau gua aac ggg gua uuu uuc aau ggu aua aua uua gga ccu gac ggc aau guc uua auc cca gag aug caa uca ucc cuc cuc cag caa cau aug gag uug uug gua ucc ucg guu auc ccc cuu aug cac ccc cug gca gac ccg ucu acc guu uuc aag aac ggu gac gag gcu gag gau uuu guu gaa guu cac cuu ccc gau gug cac gaa cgg auc uca gga guu gac uug ggu cuc ccg aac ugg
```

```
ggg aag uau gua uua cug agu gca ggg gcc cug acu gcc uug aug uug aua auu uuc cug aug aca ugc ugg aga aga guc aau cga ucg gaa ccu aca caa cac aau cuc aga ggg aca ggg agg gag gug uca guc acu ccc caa agc ggg aag auc aua ucu uca ugg gaa uca uac aag agc ggg ggu gag acc gga cug uga
```

Nucleoprotein N (RAV-N) of Pasteur Vaccine Strain:

```
Wild type mRNA sequence of the coding region
according to SEQ ID No. 12:
aug gau gcc gac aag auu gua uuc aaa guc aau aau cag gug guc ucu uug aag ccu gag auu auc gug gau caa uau gag uac aag uac ccu gcc auc aaa gau uug aaa aag ccc ugu aua acu cua gga aag gcu ccc gau uua aau aaa gca uac aag uca guu uua uca ugc aug agc gcc gcc aaa cuu gau ccu gac gau gua ugu ucc uau uug gcg gcg gca aug cag uuu uuu gag ggg aca ugu ccg aau gac ugg acc agc uau gga auc gug auu gca cga aaa gga gau aag auc acc cca ggu ucu cug gug gag aua aaa cgu acu gau gua gaa ggg aau ugg gcu cug aca gga ggc aug gaa cug aca aga gac ccc acu guc ccu gag cau gcg ucc uua guc ggu cuu cuc uug agu cug uau agg uug agc aaa aua ucc ggg caa agc acu ggu aac uau aag aca aac auu gca gac agg aua gag cag auu uuu gag aca gcc ccu uuu guu aaa auc gug gaa cac cau acu cua aug aca acu cac aaa aug ugu gcu aau ugg agu acu aua cca aac uuc aga uuu uug gcc gga acc uau gac aug uuu uuc ucc cgg auu gag cau cua uau uca gca auc aga gug ggc aca guu guc acu gcu uau gaa gac ugu uca gga cug gug uca uuu acu ggg uuc aua aaa caa auc aau cuc acc gcu aga gag gca aua cua uau uuc uuc cac aag aac uuu gag gaa gag aua aga aga aug uuu gag cca ggg cag gag aca gcu guu ccu cac ucu uau uuc auc cac uuc cgu uca cua ggc uug agu ggg aaa ucu ccu uau uca uca aau gcu guu ggu cac gug uuc aau cuc auu cac uuu gua gga ugc uau aug ggu caa guc aga ucc cua aau gca acg guu auu gcu gca gcu ccu cau gaa aug ucu guu cua ggg ggc uau cug gga gag gaa uuc uuc ggg aaa ggg aca uuu gaa aga aga uuc uuc aga gau gag aaa gaa cuu caa gaa uac gag gcg gcu gaa cug aca aag acu gac gua gca cug gca gau gau
```

-continued

```
gga acu guc aac ucu gac gac gag gac uac uuc uca ggu gaa acc aga agu ccg gaa gcu guu uau acu cga auc aua aug aau gga ggu cga cug aag aga ucg cac aua cgg aga uau guc uca guc agu ucc aau cau caa gcu cgu cca aac uca uuc gcc gag uuu cua aac aag aca uau ucg agu gac uca uaa
```

Phosphoprotein P (Also Named M1) (RAV-P) of Pasteur Vaccine Strain:

```
Wild type mRNA sequence of the coding region
according to SEQ ID No. 13:
aug agc aag auc uuu guc aau ccu agu gcu auu aga gcc ggu cug gcc gau cuu gag aug gcu gaa gaa acu guu gau cug auc aau aga aau auc gaa gac aau cag gcu cau cuc caa ggg gaa ccc aua gaa gug gac aau cuc ccu gag gau aug ggg cga cuu cac cug gau gau gga aaa ucg ccc aac ccu ggu gag aug gcc aag gug gga gaa ggc aag uau cga gag gac uuu cag aug gau gaa gga gag gau ccu agc cuc cug uuc cag uca uac cug gac aau guu gga guc caa aua guc aga caa aua agg uca gga gag aga uuu cuc aag aua ugg uca cag acc gua gaa gag auu aua ucc uau guc gcg guc aac uuu ccc aac ccu cca gga aag ucu uca gag gau aaa uca acc cag acu acc ggc cga gag cuc aag aag gag aca aca ccc acu ccu ucu cag aga gaa agc caa ucc ucg aaa gcc agg aug gcg gcu caa acu gcu ucu ggc ccu cca gcc cuu gaa ugg ucg gcc acc aau gaa gag gau gau cua uca gug gag gcu gag auc gcu cac cag auu gca gaa agu uuc ucc aaa aaa uau aag uuu ccc
```

-continued

```
ucu cga ucc uca ggg aua cuc uug uau aau uuu gag caa uug aaa aug aac cuu gau gau aua guu aaa gag gca aaa aau gua cca ggu gug acc cgu uua gcc cgu gac ggg ucc aaa cuc ccc cua aga ugu gua cug gga ugg guc gcc uug gcc aac ucu aag aaa uuc cag uug uua guc gaa ucc aac aag cug agu aaa auc aug caa gau gac uug aau cgc uau aca ucu ugc uaa
```

Matrix Protein M (Also Named M2) (RAV-M) of Pasteur Vaccine Strain:

```
Wild type mRNA sequence of the coding region
according to SEQ ID No. 14:
aug aac uuu cua cgu aag aua gug aaa aau ugc agg gac gag gac acu caa aaa ccc ucu ccc gug uca gcc ccu cug gau gac gau gac uug ugg cuu cca ccc ccu gaa uac guc ccg cua aaa gaa cuu aca agc aag aag aac agg agg aac uuu ugu auc aac gga ggg guu aaa gug ugu agc ccg aau ggu uac ucg uuc ggg auc cug cgg cac auu cug aga uca uuc gac gag aua uau ucu ggg aau cau agg aug guc ggg uua guc aaa gua guu auu gga cug gcu uug uca gga gcu cca guc ccu gag ggc aug aac ugg gua uac aag uug agg aga acc cuu auc uuc cag ugg gcu gau ucc agg ggc ccu cuu gaa ggg gag gag uug gaa uac ucu cag gag auc acu ugg gau gau aau acu gag uuc guc gga uug caa aua aga gug agu gca aaa cag ugu cau auc cgg ggc aga auc ugg ugu auc aac aug aac ucg aga gca ggu caa cua ugg ucu gac aug ucu cuu cag aca caa agg ucc gaa gag gac aaa gau ucc ucu cug cuu cua gaa uaa
```

RNA Polymerase L (RAV-L) of Pasteur Vaccine Strain:

```
Wild type mRNA sequence of the coding region according to SEQ ID No. 15:
aug cuc gau ccu gga gag guc uau gau gac ccu auu gac cca auc gag uua gag gcu gaa ccc aga gga acc ccc acu guc ccc aac auc uug agg aac ucu gac uac aau cuc aac ucu ccu uug aua gaa gau ccu gcu aga cua aug uua gaa ugg uua aaa aca ggg aau aga ccu uau cgg aug acu cua aca gac aau ugc ucc agg ucu uuc aga guu uug aaa gau uau uuc aag aag gua gau uug ggu ucc ucu aag gug ggc gga aug gcu gca cag uca aug auu cuc ucu ugg uua uau ggc cac ucu gaa ucc aac agg agc cgg aga ugu aua aca gac uug gcc cau uuc uau ucc aag ucg ucc ccc aua gag aag cug uua aau ucc acg cua gga aau aga ggg cug aga auc ccc cca gag gga gug uua agu ugc cuu gag agg guu gau uau gau aau gca uuu gga agg uau cuu gcc aac acg uau ucc ucu uac uug uuc uuc cau gua auc acc uua uac aug aac gcc cua gac ugg gau gaa gaa aag acc auc cua gca uua ugg aaa gau uua acc uca gug gac auc ggg aag gac uug gua aag uuc aaa gac caa aua ugg gga cug cug auc gug aca aag gac uuu guu uac ucc caa agu ucc aau ugu cuu uuu gac aga aac uac aca cuu aug cua aaa gau cuu uuc uug ucu cgc
```

-continued uuc aac ucc uua aug guc uua cuu ucu ccc cca gag ccc cga uac uca gau gac uug aua ucu cag cua
ugc cag cug uac auu gcu ggg gau caa guc uug ucu aug ugu gga aac ucc ggc uau gaa guc auc aaa
aua uug gag cca uau guc gug aau agu uua guc cag aga gca gaa aag uuu agg ccu cuc auu cau ucc
uug gga gac uuu ccu gua uuu aua aaa gac aag gua agu caa cuc gaa gag acg uuc ggu ucc ugu gca
aga agg uuc uuu agg gcu cug gau caa uuc gac aac aua cau gac uug guu uuu gug uau ggc ugu uac
agg cau ugg ggg cac cca uau aua gau uau cga aag ggu cug uca aaa cua uau gau cag guu cac auu
aaa aaa gug aua gau aag ucc uac cag gag ugc uua gca agc gac cua gcc agg agg auc cuu aga ugg
ggu uuu gau aag uac ucc aag ugg uau cug gau uca cga uuc cua gcc cga gac cac ccc uug acu ccu
uau auc aaa acc caa aca ugg cca ccc aaa cau auu gua gau uug gug ggg gau aca ugg cac aag cuc
ccg auc acg caa auc uuu gag auu ccu gaa uca aug gau cca uca gaa aua uug gau gac aaa uca cau
ucu uuc acc aga acg aga cua gcu ucu ugg cug uca gaa aac cga ggg ggg ccu guu ccu agc gaa aaa
guu auu auc acg gcc cug ucu aag ccg ccu guc aau ccc cga gag uuu cug aag ucu aua gac cuc gga
gga uug cca gau gaa gac uug aua auu ggc cuc aag cca aag gaa cgg gaa uug aag auu gaa ggu cga
uuc uuu gcu cua aug uca ugg aau cua aga uug uau uuu guc auc acu gaa aaa cuc uug gcc aac uac
auc uug cca cuu uuu gac gcg cug acu aug aca gac aac cug aac aag gug uuu aaa aag cug auc gac
agg guc acc ggg caa ggg cuu cug gac uau uca agg guc aca uau gca uuu cac cug gac uau gaa aag
ugg aac aac cau caa aga uua gag uca aca gag gau gua uuu ucu guc uua gau caa gug uuu gga uug
aag aga gug uuu ucu aga aca cac gag uuu uuu cag aag ucc ugg auc uau uca gac aga uca gac
cuc auc ggg uua cgg gag gau caa aua uac ugc uua gau gcg ucc aac ggc cca acc ugu ugg aau ggc
cag gau ggc ggg cua gaa ggc uua cgg cag aag ggc ugg agu cua guc agc uua aug aua gau aga
gaa ucu caa auc agg aac aca aga acc aaa gua cua gcu caa gga gac aac cag guu uua ugu ccg aca
uau aug uug ucg cca ggg cua ucu caa gag ggg cuc ucu uau gaa uug gag agc aua uca agg aau gca
uuu ucg aua uac aga gcc guc gag gaa ggg gca ucu aaa cua ggg cug auc auc aag aaa gaa gag acc
aug ugu agu uau gac uuc cuc auc uau gga aaa acc ccu uug uuu aga ggu aac aua uug gug ccu gag
ucc aaa aga ugg gcc aga guc ucu ugc guc ucu aau gac caa aua guc aac cuc gcc aau aua aug ucg
aca gug ucc acc aac gcg cua aca gug gca caa cac ucu caa ucu uug auc aaa ccg aug agg gau uuu
cug cuc aug uca gua cag gca guc uuu cac uac cug cua uuu agc cca auc uua aag gga aga guu uac
aag auu cug agc gcu gaa ggg gag agc uuu cuc cua gcc aug uca agg aua auc uau cua gau ccu ucu
uug gga ggg gua ucu gga aug ucc cuc gga aga uuc cau aua cga cag uuc uca gac ccu guc ucu gaa
ggg uua ccu uuc ugg aga gag auc ugg uua agc cca cac gag ucc ugg auu cac gcg uug ugu caa gag
gcu gga aac cca gau cuu gga gag aga aca cuc gag agc uuc acu cgc cuu cua gaa gau ccu acc acc
uua aau auc aga gga ggg gcc agu ccu acc auu cua cuc aag gau gca auc aga aag gcu uua uau gac
gag gug gac aag gug gag aac uca gag uuu cga gag gca auc cug uuc ucc aag acc aua gau aau
uuu aua cuc uuc uua aca ucu guu gag ccu cug uuu ccu cga uuu ucu gug agc uau ucu gag cua uuc agu ucg ucu
uuu uug gga auc ccc gag uca auc auu gga cug aua caa aac ucc cga acg aua aga agg cag uuu aga
aag agu cuc uca aaa acu uua gaa gaa ucc uuc uac aac uca gag auc cac ggg auu agu cgg aug acc
cag aca ccu cag agg guu ggg ggg gug ugg ccu ugc ucu uca gag agg gca gau cua cuu agg gag auc
ucu ugg gga aga aaa gug gua ggc acg aca guu ccu cac ccu ucu gag aug uug ggg uua cuu ccc aag
ucc ucu auu ucu ugc acu ugu gga gca aca gga gga ggc aau ccu aga guu ucu gua uca gua cuc ccg
ucu uuu gau cag uca uuu uuu ugc acg ggg ccc cua aag ggg uac uug ggc ucg ucc acc ucu aug ucg -continued

```
acc cag cua uuc cau gca ugg gaa aaa guc acu aau guu cau gug gug aag aga gcu cua ucg uua aaa
gaa ucu aua aac ugg uuc auu acu aga gau ucc aac uug gcu caa acu cua auu agg aac auu gug ucu
cug aca ggc ccu gau uuc ccu cua gag gag gcc ccu guu uuc aaa agg acg ggg uca gcc uug cau agg
uuc aag ucu gcc aga uac agc gaa gga ggg uau ucu ucu gua ugc ccg aac cuc cuc ucu cau auu ucu
guu agu aca gac acc aug ucu gau uug acc caa gac ggg aag aac uac gau uuc aug uuc cag cca uug
aug cuu uau gca cag aca ugg aca uca gag cug gua cag aga gac aca agg cua aga gac ucu acg uuu
cau ugg cac cuc caa ugc aac agg ugu gug aga ccc auu gac gac gug acc cug gag acc ucu cag auc
uuc gag uuu ccg gau gug ucg aaa aga aua ucc aga aug guu ucu ggg gcu gug cca cac uuc cag agg
cuu ccc gau auc cgu cug aga cca gga gau uuu gaa ucu cua agc ggu aga gaa aag ucu cac cau auc
gga uca gcu cag ggg cuc uua uac uca auc uua gug gca auu cac gac uca gga uac aau gau gga acc
auc uuc ccu guc aac aua uac ggc aag guu ucc ccu aga gac uau uug aga ggg cuc gca agg gga gua
uug aua gga ucc ucg auu ugc uuc uug acg aga aug aca aau auc aau auu aau aga ccu cuu gaa uug
auc uca ggg gua auc uca uau auu cuc cug agg cua gau aac cau ccc ucc uug uac aua aug cuc aga
gaa ccg ucu uuu aga gaa gag aua uuu ucu auc ccu cag aaa auc ccc gcu uau cca acc acu aug
aaa gaa ggc aac aga uca auc uug ugu uau cuc caa cau gug cua cgc uau gag cga gag gua auc acg
gcg ucu cca gag aau gac ugg cua ugg auc uuu uca gac uuu aga agu gcc aaa aug acg uac cua acc
cuc auu acu uac cag ucu cau cuu cua cuc cag agg guu gag aga aac cua ucu aag agu aug aga gau
aac cug cga caa uug agu ucc uug aug agg cag gug cug ggc ggg cac gga gaa gau acc uua gag uca
gac gac aac auu caa cga cua cua aaa gac ucu uua cga agg aca aga ugg gug gau caa gag gug cgc
cau gca gcu aga acc aug acu gga gau uac agc ccc aac aag aag gug ucc cgu aag gua gga ugu uca
gaa ugg guc ugc ucu gcu caa cag guu gca guc ucu acc uca gca aac ccg gcc ccu guc ucg gag cuu
gac aua agg gcc cuc ucu aag agg uuc cag aac ccu uug auc ucg ggc uug aga gug guu cag ugg gca
acc ggu gcu cau uau aag cuu aag ccu auu cua gau gau ucc aau guu uuc cca ucu cuc ugc cuu gua
guu ggg gac ggg uca ggg ggg aua uca agg gca guc cuc aac aug uuu cca gau gcc aag cuu gug uuc
aac agu cuu uua gag gug aau gac cug aug gcu ucc gga aca cau cca cug ccu ccu uca gca auc aug
agg gga gga aau gau auc guc ucc aga gug aua gau uuu gac uca auc ugg gaa aaa ccg ucc gac uug
aga aac uug gcu acc ugg aaa uac uuc cag uca guc caa aag cag guc aac aug ucc uau gac cuc auu
auu ugc gau gca gaa guu acu gac auu gca cuu auc aac cgg aua acc ugu uua aug ucc gau uuu gca
uug ucu aua gau gga cca cuc uau uug guc uuc aaa acu uau ggg acu aug cua gua aau cca aac uac
aag gcu auu caa cac cug uca aga gcg uuc ccc ucg guc aca ggg uuu auc acc caa gua acu ucg ucu
uuu uca ucu gag cuc uac cuu cga uuc ucc aaa cga ggg aag uuu uca aga gau gcu gag uac uug acc
ucu ucc acc cuu cga gaa aug agc cuu gug uua uuc aau ugu agc agc ccc aag agu gag aug cag aga
gcu cgu ucc uug aac uau cag gau cuu gug aga gga uuu ccu gaa gaa auc aua uca aau ccu uac aau
gag aug auc aua acu cug auu gac agu gau gua gaa ucu uuu cua guc cac aag aug gug gau gau cuu
gag uua cag agg gga acu cug ucu aaa gug gcu auc aua gcc auc aua guu uuc ucc aac aga
guc uuc aac guu ucc aaa ccc cua acu gac ccc uug uuc uau cca ccg ucu gau ccc aaa auc cug agg
cac uuc aac aua ugu ugc agu acu aug aug uau cua ucu acu gcu uua ggu gac guc ccu agc uuc gca
aga cuu cac gac cug uau aac aga ccu aua acu uau ucu aga aag caa guc auu cua ggg aac guu
uau cua ucu ugg agu ugg ucc aac gac acc uca gug uuc aaa agg uag gcc ugu aau ucu agc cug agu
cug uca ucu cac ugg auc agg uug auu uac aag aua gug aag acu acc aga cuc guu ggc agc auc aag
```

-continued

```
gau cua ucc gga gaa gug gaa aga cac cuu cau agg uac aac agg ugg auc acc cua gag aau auc aga ucu aga uca ucc cua cua gac uac agu ugc cug ugc auc gga uac ucc ugg aag ccu gcc cau gcu aag acu cuu gug uga
```

In the context of the invention additionally to the here disclosed nucleic acid sequences also nucleic acid sequences of different Rabies virus isolates are incorporated herewith. These different Rabies virus isolates show preferably an identity of at least 50%, 60%, 70%, more preferably of at least 80% and most preferably of at least 90% with the nucleic acid sequences according to SEQ ID Nos. 11-15 or of fragments thereof.

Examples for such different Rabies virus isolates are:

Rabies virus strains according to the NCBI Accession Nos. JQ730682, AF499686, AB569299, AB839170, AB781935, FJ959397, AB362483, EF206720, EF206718, EF206717, EF206715, EF206714, EF206713, EF206712, EF206711, EF206710, EF206709, EF206708, EF206707, EU182346, HM535790, GQ918139, EU877071, EU877070, EU877069, EU182347, M31046, EU877068, EU877067, EF542830, AB839169, JQ647510, KC169986, JX088694, JQ730682, JN609295, JN234411, HQ317918, EF206719, EF564174, EU643590, JQ946087, FJ913470 HQ891318, AB645847, AB569299, AY705373, GU565704, GU565703, FJ577895, JX276550, FJ866836, FJ866835, DQ875051, DQ875050, AB128149, AB009663, AB044824, JQ944709, EU345004, EU345003, EU345002, AB608731, EF564173, JQ423952, AB618037, AB618036, AB618035, AB618034, AB618033, AB618032, AB085828, M13215, M21634, AB247437, AB247436, AB247435, AB247434, AB247433, AB247432, D42112, AB247430, and AB247431.

In a preferred embodiment, the mRNA according to the invention does not comprise a reporter gene or a marker gene. Preferably, the mRNA according to the invention does not encode, for instance, luciferase; green fluorescent protein (GFP) and its variants (such as eGFP, RFP or BFP); α-globin; hypoxanthine-guanine phosphoribosyltransferase (HGPRT); β-galactosidase; galactokinase; alkaline phosphatase; secreted embryonic alkaline phosphatase (SEAP)) or a resistance gene (such as a resistance gene against neomycin, puromycin, hygromycin and zeocin). In a preferred embodiment, the mRNA according to the invention does not encode luciferase. In another embodiment, the mRNA according to the invention does not encode GFP or a variant thereof.

In a further preferred embodiment, the mRNA according to the invention does not encode a protein (or a fragment of a protein) derived from a virus belonging to the family of Orthomyxoviridae. Preferably the mRNA does not encode a protein that is derived from an influenza virus, more preferably an influenza A virus. Preferably, the mRNA according to the invention does not encode an influenza A protein selected from the group consisting of hemagglutinin (HA), neuraminidase (NA), nucleoprotein (NP), M1, M2, NS1, NS2 (NEP: nuclear export protein), PA, PB1 (polymerase basic 1), PB1-F2 and PB2. In another preferred embodiment, the mRNA according to the invention does not encode ovalbumin (OVA) or a fragment thereof. Preferably, the mRNA according to the invention does not encode an influenza A protein or ovalbumin.

By a further embodiment, the inventive mRNA preferably comprises at least one of the following structural elements: a 5'- and/or 3'-untranslated region element (UTR element), particularly a 5'-UTR element which comprises or consists of a nucleic acid sequence which is derived from the 5'-UTR of a TOP gene or from a fragment, homolog or a variant thereof, or a 5'- and/or 3'-UTR element which may be derivable from a gene that provides a stable mRNA or from a homolog, fragment or variant thereof; a histone-stem-loop structure, preferably a histone-stem-loop in its 3' untranslated region; a 5'-CAP structure; a poly-A tail; or a poly(C) sequence.

In a preferred embodiment of the first aspect of the present invention the inventive mRNA comprises at least one 5'- or 3'-UTR element. In this context an UTR element comprises or consists of a nucleic acid sequence which is derived from the 5'- or 3'-UTR of any naturally occurring gene or which is derived from a fragment, a homolog or a variant of the 5'- or 3'-UTR of a gene. Preferably the 5'- or 3'-UTR element used according to the present invention is heterologous to the coding region of the inventive mRNA sequence. Even if 5'- or 3'-UTR elements derived from naturally occurring genes are preferred, also synthetically engineered UTR elements may be used in the context of the present invention.

In a particularly preferred embodiment of the first aspect of the present invention the inventive mRNA sequence comprises at least one 5'-untranslated region element (5'UTR element) which comprises or consists of a nucleic acid sequence which is derived from the 5'UTR of a TOP gene or which is derived from a fragment, homolog or variant of the 5'UTR of a TOP gene.

It is particularly preferred that the 5'UTR element does not comprise a TOP-motif or a 5'TOP, as defined above.

In some embodiments, the nucleic acid sequence of the 5'UTR element which is derived from a 5'UTR of a TOP gene terminates at its 3'-end with a nucleotide located at position 1, 2, 3, 4, 5, 6, 7, 8, 9 or 10 upstream of the start codon (e.g. A(U/T)G) of the gene or mRNA it is derived from. Thus, the 5'UTR element does not comprise any part of the protein coding region. Thus, preferably, the only protein coding part of the inventive mRNA is provided by the coding region.

The nucleic acid sequence which is derived from the 5'UTR of a TOP gene is derived from a eukaryotic TOP gene, preferably a plant or animal TOP gene, more preferably a chordate TOP gene, even more preferably a vertebrate TOP gene, most preferably a mammalian TOP gene, such as a human TOP gene.

For example, the 5'UTR element is preferably selected from 5'-UTR elements comprising or consisting of a nucleic acid sequence which is derived from a nucleic acid sequence selected from the group consisting of SEQ ID Nos. 1-1363, SEQ ID NO. 1395, SEQ ID NO. 1421 and SEQ ID NO. 1422 of the patent application WO2013/143700, whose disclosure is incorporated herein by reference, from the homologs of SEQ ID Nos. 1-1363, SEQ ID NO. 1395, SEQ ID NO. 1421 and SEQ ID NO. 1422 of the patent application WO2013/143700, from a variant thereof, or preferably from a corresponding RNA sequence. The term "homologs of SEQ ID Nos. 1-1363, SEQ ID NO. 1395, SEQ ID NO. 1421 and SEQ ID NO. 1422 of the patent application WO2013/143700"

refers to sequences of other species than *Homo sapiens*, which are homologous to the sequences according to SEQ ID Nos. 1-1363, SEQ ID NO. 1395, SEQ ID NO. 1421 and SEQ ID NO. 1422 of the patent application WO2013/143700.

In a preferred embodiment, the 5'UTR element comprises or consists of a nucleic acid sequence which is derived from a nucleic acid sequence extending from nucleotide position 5 (i.e. the nucleotide that is located at position 5 in the sequence) to the nucleotide position immediately 5' to the start codon (located at the 3' end of the sequences), e.g. the nucleotide position immediately 5' to the ATG sequence, of a nucleic acid sequence selected from SEQ ID Nos. 1-1363, SEQ ID NO. 1395, SEQ ID NO. 1421 and SEQ ID NO. 1422 of the patent application WO2013/143700, from the homologs of SEQ ID Nos. 1-1363, SEQ ID NO. 1395, SEQ ID NO. 1421 and SEQ ID NO. 1422 of the patent application WO2013/143700 from a variant thereof, or a corresponding RNA sequence. It is particularly preferred that the 5' UTR element is derived from a nucleic acid sequence extending from the nucleotide position immediately 3' to the 5'TOP to the nucleotide position immediately 5' to the start codon (located at the 3' end of the sequences), e.g. the nucleotide position immediately 5' to the ATG sequence, of a nucleic acid sequence selected from SEQ ID Nos. 1-1363, SEQ ID NO. 1395, SEQ ID NO. 1421 and SEQ ID NO. 1422 of the patent application WO2013/143700, from the homologs of SEQ ID Nos. 1-1363, SEQ ID NO. 1395, SEQ ID NO. 1421 and SEQ ID NO. 1422 of the patent application WO2013/143700, from a variant thereof, or a corresponding RNA sequence.

In a particularly preferred embodiment, the 5'UTR element comprises or consists of a nucleic acid sequence which is derived from a 5'UTR of a TOP gene encoding a ribosomal protein or from a variant of a 5'UTR of a TOP gene encoding a ribosomal protein. For example, the 5'UTR element comprises or consists of a nucleic acid sequence which is derived from a 5'UTR of a nucleic acid sequence according to any of SEQ ID NOs: 67, 170, 193, 244, 259, 554, 650, 675, 700, 721, 913, 1016, 1063, 1120, 1138, and 1284-1360 of the patent application WO2013/143700, a corresponding RNA sequence, a homolog thereof, or a variant thereof as described herein, preferably lacking the 5'TOP motif. As described above, the sequence extending from position 5 to the nucleotide immediately 5' to the ATG (which is located at the 3'end of the sequences) corresponds to the 5'UTR of said sequences.

Preferably, the 5'UTR element comprises or consists of a nucleic acid sequence which is derived from a 5'UTR of a TOP gene encoding a ribosomal Large protein (RPL) or from a homolog or variant of a 5'UTR of a TOP gene encoding a ribosomal Large protein (RPL). For example, the 5'UTR element comprises or consists of a nucleic acid sequence which is derived from a 5'UTR of a nucleic acid sequence according to any of SEQ ID NOs: 67, 259, 1284-1318, 1344, 1346, 1348-1354, 1357, 1358, 1421 and 1422 of the patent application WO2013/143700, a corresponding RNA sequence, a homolog thereof, or a variant thereof as described herein, preferably lacking the 5'TOP motif.

In a particularly preferred embodiment, the 5'UTR element comprises or consists of a nucleic acid sequence which is derived from the 5'UTR of a ribosomal protein Large 32 gene, preferably from a vertebrate ribosomal protein Large 32 (L32) gene, more preferably from a mammalian ribosomal protein Large 32 (L32) gene, most preferably from a human ribosomal protein Large 32 (L32) gene, or from a variant of the 5'UTR of a ribosomal protein Large 32 gene, preferably from a vertebrate ribosomal protein Large 32 (L32) gene, more preferably from a mammalian ribosomal protein Large 32 (L32) gene, most preferably from a human ribosomal protein Large 32 (L32) gene, wherein preferably the 5'TOP element does not comprise the 5'TOP of said gene.

Accordingly, in a particularly preferred embodiment, the 5'UTR element comprises or consists of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID No. 16 (5'-UTR of human ribosomal protein Large 32 lacking the 5' terminal oligopyrimidine tract: GGCGCTGCCTACGGAGGTGGCAGC-CATCTCCTTCTCGGCATC; corresponding to SEQ ID No. 1368 of the patent application WO2013/143700) or preferably to a corresponding RNA sequence, or wherein the at least one 5'UTR element comprises or consists of a fragment of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID No. 16 or more preferably to a corresponding RNA sequence, wherein, preferably, the fragment is as described above, i.e. being a continuous stretch of nucleotides representing at least 20% etc. of the full-length 5'UTR. Preferably, the fragment exhibits a length of at least about 20 nucleotides or more, preferably of at least about 30 nucleotides or more, more preferably of at least about 40 nucleotides or more. Preferably, the fragment is a functional fragment as described herein.

In some embodiments, the inventive mRNA comprises a 5'UTR element which comprises or consists of a nucleic acid sequence which is derived from the 5'UTR of a vertebrate TOP gene, such as a mammalian, e.g. a human TOP gene, selected from RPSA, RPS2, RPS3, RPS3A, RPS4, RPS5, RPS6, RPS7, RPS8, RPS9, RPS10, RPS11, RPS12, RPS13, RPS14, RPS15, RPS15A, RPS16, RPS17, RPS18, RPS19, RPS20, RPS21, RPS23, RPS24, RPS25, RPS26, RPS27, RPS27A, RPS28, RPS29, RPS30, RPL3, RPL4, RPL5, RPL6, RPL7, RPL7A, RPL8, RPL9, RPL10, RPL10A, RPL11, RPL12, RPL13, RPL13A, RPL14, RPL15, RPL17, RPL18, RPL18A, RPL19, RPL21, RPL22, RPL23, RPL23A, RPL24, RPL26, RPL27, RPL27A, RPL28, RPL29, RPL30, RPL31, RPL32, RPL34, RPL35, RPL35A, RPL36, RPL36A, RPL37, RPL37A, RPL38, RPL39, RPL40, RPL41, RPLP0, RPLP1, RPLP2, RPLP3, RPLP0, RPLP1, RPLP2, EEF1A1, EEF1B2, EEF1D, EEF1G, EEF2, EIF3E, EIF3F, EIF3H, EIF2S3, EIF3C, EIF3K, EIF3EIP, EIF4A2, PABPC1, HNRNPA1, TPT1, TUBB1, UBA52, NPM1, ATP5G2, GNB2L1, NME2, UQCRB, or from a homolog or variant thereof, wherein preferably the 5'UTR element does not comprise a TOP-motif or the 5'TOP of said genes, and wherein optionally the 5'UTR element starts at its 5'-end with a nucleotide located at position 1, 2, 3, 4, 5, 6, 7, 8, 9 or 10 downstream of the 5'terminal oligopyrimidine tract (TOP) and wherein further optionally the 5'UTR element which is derived from a 5'UTR of a TOP gene terminates at its 3'-end with a nucleotide located at position 1, 2, 3, 4, 5, 6, 7, 8, 9 or 10 upstream of the start codon (A(U/T)G) of the gene it is derived from.

In further particularly preferred embodiments, the 5'UTR element comprises or consists of a nucleic acid sequence which is derived from the 5'UTR of a ribosomal protein Large 32 gene (RPL32), a ribosomal protein Large 35 gene (RPL35), a ribosomal protein Large 21 gene (RPL21), an ATP synthase, H+ transporting, mitochondrial F1 complex, alpha subunit 1, cardiac muscle (ATP5A1) gene, an hydroxysteroid (17-beta) dehydrogenase 4 gene (HSD17B4), an androgen-induced 1 gene (AIG1), cytochrome c oxidase subunit VIc gene (COX6C), or a N-acylsphingosine amidohydrolase (acid ceramidase) 1 gene (ASAH1) or from a variant thereof, preferably from a vertebrate ribosomal protein Large 32 gene (RPL32), a vertebrate ribosomal protein Large 35 gene (RPL35), a vertebrate ribosomal protein Large 21 gene (RPL21), a vertebrate ATP synthase, H+ transporting, mitochondrial F1 complex, alpha subunit 1, cardiac muscle (ATP5A1) gene, a vertebrate hydroxysteroid (17-beta) dehydrogenase 4 gene (HSD17B4), a vertebrate androgen-induced 1 gene (AIG1), a vertebrate cytochrome c oxidase subunit VIc gene (COX6C), or a vertebrate N-acylsphingosine amidohydrolase (acid ceramidase) 1 gene (ASAH1) or from a variant thereof, more preferably from a mammalian ribosomal protein Large 32 gene (RPL32), a ribosomal protein Large 35 gene (RPL35), a ribosomal protein Large 21 gene (RPL21), a mammalian ATP synthase, H+ transporting, mitochondrial F1 complex, alpha subunit 1, cardiac muscle (ATP5A1) gene, a mammalian hydroxysteroid (17-beta) dehydrogenase 4 gene (HSD17B4), a mammalian androgen-induced 1 gene (AIG1), a mammalian cyto-chrome c oxidase subunit VIc gene (COX6C), or a mammalian N-acylsphingosine ami-dohydrolase (acid ceramidase) 1 gene (ASAH1) or from a variant thereof, most preferably from a human ribosomal protein Large 32 gene (RPL32), a human ribosomal protein Large 35 gene (RPL35), a human ribosomal protein Large 21 gene (RPL21), a human ATP syn-thase, H+ transporting, mitochondrial F1 complex, alpha subunit 1, cardiac muscle (ATP5A1) gene, a human hydroxysteroid (17-beta) dehydrogenase 4 gene (HSD17B4), a human androgen-induced 1 gene (AIG1), a human cytochrome c oxidase subunit VIc gene (COX6C), or a human N-acylsphingosine amidohydrolase (acid ceramidase) 1 gene (ASAH1) or from a variant thereof, wherein preferably the 5'UTR element does not comprise the 5'TOP of said gene.

Accordingly, in a particularly preferred embodiment, the 5'UTR element comprises or consists of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID No. 1368, or SEQ ID NOs 1412-1420 of the patent application WO2013/143700, or a corresponding RNA sequence, or wherein the at least one 5'UTR element comprises or consists of a fragment of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID No. 1368, or SEQ ID NOs 1412-1420 of the patent application WO2013/143700, wherein, preferably, the fragment is as described above, i.e. being a continuous stretch of nucleotides representing at least 20% etc. of the full-length 5'UTR. Preferably, the fragment exhibits a length of at least about 20 nucleotides or more, preferably of at least about 30 nucleotides or more, more preferably of at least about 40 nucleotides or more. Preferably, the fragment is a functional fragment as described herein.

Accordingly, in a particularly preferred embodiment, the 5'UTR element comprises or consists of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID No. 26 (5'-UTR of ATP5A1 lacking the 5' terminal oligopyrimidine tract: GCGGCTCGGCCAT-TTTGTCCCAGTCAGTCCG-GAGGCTGCGGCTGCAGAAGTACCGCC TGCG-GAGTAACTGCAAAG; corresponding to SEQ ID No. 1414 of the patent application WO2013/143700) or preferably to a corresponding RNA sequence, or wherein the at least one 5'UTR element comprises or consists of a fragment of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID No. 26 or more preferably to a corresponding RNA sequence, wherein, preferably, the fragment is as described above, i.e. being a continuous stretch of nucleotides representing at least 20% etc. of the full-length 5'UTR. Preferably, the fragment exhibits a length of at least about 20 nucleotides or more, preferably of at least about 30 nucleotides or more, more preferably of at least about 40 nucleotides or more. Preferably, the fragment is a functional fragment as described herein.

In a further preferred embodiment, the inventive mRNA further comprises at least one 3'UTR element which comprises or consists of a nucleic acid sequence derived from the 3'UTR of a chordate gene, preferably a vertebrate gene, more preferably a mammalian gene, most preferably a human gene, or from a variant of the 3'UTR of a chordate gene, preferably a vertebrate gene, more preferably a mammalian gene, most preferably a human gene.

The term '3'UTR element' refers to a nucleic acid sequence which comprises or consists of a nucleic acid sequence that is derived from a 3'UTR or from a variant of a 3'UTR. A 3'UTR element in the sense of the present invention may represent the 3'UTR of an mRNA. Thus, in the sense of the present invention, preferably, a 3'UTR element may be the 3'UTR of an mRNA, preferably of an artificial mRNA, or it may be the transcription template for a 3'UTR of an mRNA. Thus, a 3'UTR element preferably is a nucleic acid sequence which corresponds to the 3'UTR of an mRNA, preferably to the 3'UTR of an artificial mRNA, such as an mRNA obtained by transcription of a genetically engineered vector construct. Preferably, the 3'UTR element fulfils the function of a 3'UTR or encodes a sequence which fulfils the function of a 3'UTR.

Preferably, the inventive mRNA comprises a 3'UTR element which may be derivable from a gene that relates to an mRNA with an enhanced half-life (that provides a stable mRNA), for example a 3'UTR element as defined and described below.

In a particularly preferred embodiment, the 3'UTR element comprises or consists of a nucleic acid sequence which is derived from a 3'UTR of a gene selected from the group consisting of an albumin gene, an α-globin gene, a β-globin gene, a tyrosine hydroxylase gene, a lipoxygenase gene, and a collagen alpha gene, such as a collagen alpha 1(I) gene, or from a variant of a 3'UTR of a gene selected from the group consisting of an albumin gene, an α-globin gene, a β-globin gene, a tyrosine hydroxylase gene, a lipoxygenase gene, and a collagen alpha gene, such as a collagen alpha 1(I) gene according to SEQ ID No. 1369-1390 of the patent application WO2013/143700 whose disclosure is incorporated herein by reference. In a particularly preferred embodiment, the 3'UTR element comprises or consists of a nucleic acid sequence which is derived from a 3'UTR of an albumin gene, preferably a vertebrate albumin gene, more preferably a mammalian albumin gene, most preferably a human albumin gene according to SEQ ID No. 17

```
Human albumin 3'UTR SEQ ID No. 17:
CATCACATTT AAAAGCATCT CAGCCTACCA TGAGAATAAG

AGAAAGAAAA TGAAGATCAA AAGCTTATTC ATCTGTTTTT

CTTTTTCGTT GGTGTAAAGC CAACACCCTG TCTAAAAAAC

ATAAATTTCT TTAATCATTT TGCCTCTTTT CTCTGTGCTT

CAATTAATAA AAAATGGAAA GAATCT (corresponding to SEQ

ID No: 1369 of the patent application WO2013/

143700).
```

In this context it is particularly preferred that the inventive mRNA comprises a 3'-UTR element comprising a corresponding RNA sequence derived from the nucleic acids according to SEQ ID No. 1369-1390 of the patent application WO2013/143700 or a fragment, homolog or variant thereof.

Most preferably the 3'-UTR element comprises the nucleic acid sequence derived from a fragment of the human albumin gene according to SEQ ID No. 18:

```
albumin7 3'UTR
CATCACATTTAAAAGCATCTCAGCCTACCATGAGAATAAGAGAAAGAAAA

TGAAGATCAATAGCTTATTCATCTCTTTTTCTTTTTCGTTGGTGTAAAGC

CAACACCCTGTCTAAAAAACATAAATTTCTTTAATCATTTTGCCTCTTTT

CTCTGTGCTTCAATTAATAAAAAATGGAAAGAACCT (SEQ ID No.

18 corresponding to SEQ ID No: 1376 of the patent application WO2013/143700)
```

In is context is particularly preferred a the 3-UTR element of the inventive mRNA comprises or consists of a corresponding RNA sequence of the nucleic acid sequence according to SEQ ID No. 18.

In another particularly preferred embodiment, the 3'UTR element comprises or consists of a nucleic acid sequence which is derived from a 3'UTR of an α-globin gene, preferably a vertebrate α- or β-globin gene, more preferably a mammalian α- or β-globin gene, most preferably a human α- or β-globin gene according to SEQ ID No. 19-21:

```
3'-UTR of Homo sapiens hemoglobin, alpha 1 (HBA1)
GCTGGAGCCTCGGTGGCCATGCTTCTTGCCCCTTGGGCCTCCCCCCAGCC

CCTCCTCCCCTTCCTGCACCCGTACCCCCGTGGTCTTTGAATAAAGTCTG

AGTGGGCGGC (SEQ ID No: 19 corresponding to SEQ ID

No. 1370 of the patent application WO2013/143700)

3''-UTR of Homo sapiens hemoglobin, alpha 2 (HBA2)
GCTGGAGCCTCGGTAGCCGTTCCTCCTGCCCGCTGGGCCTCCCAACGGGC

CCTCCTCCCCTCCTTGCACCGGCCCTTCCTGGTCTTTGAATAAAGTCTGA

GTGGGCAG (SEQ ID No: 20 corresponding to SEQ ID

No. 1371 of the patent application WO2013/143700)

3'-UTR of Homo sapiens hemoglobin, beta (HBB)
GCTCGCTTTCTTGCTGTCCAATTTCTATTAAAGGTTCCTTTGTTCCCTAA

GTCCAACTACTAAACTGGGGGATATTATGAAGGGCCTTGAGCATCTGGAT

TCTGCCTAATAAAAAACATTTATTTTCATTGC (SEQ ID No: 21 corresponding to SEQ ID No. 1372 of the patent application WO2013/143700)
```

For example, the 3'UTR element may comprise or consist of the center, α-complex-binding portion of the 3'UTR of an α-globin gene, such as of a human α-globin gene, preferably according to SEQ ID No. 22:

```
Center, α-complex-binding portion of the 3'UTR of
an α-globin gene (also named herein as "muag")
GCCCGATGGGCCTCCCAACGGGCCCTCCTCCCCTCCTTGCACCG (SEQ ID NO. 22 corresponding to SEQ ID No. 1393 of the patent application WO2013/143700).
```

In this context it is particularly preferred that the 3'-UTR element of the inventive mRNA comprises or consists of a corresponding RNA sequence of the nucleic acid sequence according to SEQ ID No. 22 or a homolog, a fragment or variant thereof.

The term 'a nucleic acid sequence which is derived from the 3'UTR of a [ . . . ] gene' preferably refers to a nucleic acid sequence which is based on the 3'UTR sequence of a [ . . . ] gene or on a part thereof, such as on the 3'UTR of an albumin gene, an α-globin gene, a β-globin gene, a tyrosine hydroxylase gene, a lipoxygenase gene, or a collagen alpha gene, such as a collagen alpha 1(I) gene, preferably of an albumin gene or on a part thereof. This term includes sequences corresponding to the entire 3'UTR sequence, i.e. the full length 3'UTR sequence of a gene, and sequences corresponding to a fragment of the 3'UTR sequence of a gene, such as an albumin gene, α-globin gene, β-globin gene, tyrosine hydroxylase gene, lipoxygenase gene, or collagen alpha gene, such as a collagen alpha 1(I) gene, preferably of an albumin gene.

The term 'a nucleic acid sequence which is derived from a variant of the 3'UTR of a [ . . . ] gene' preferably refers to a nucleic acid sequence which is based on a variant of the 3'UTR sequence of a gene, such as on a variant of the 3'UTR of an albumin gene, an (α-globin gene, a β-globin gene, a tyrosine hydroxylase gene, a lipoxygenase gene, or a collagen alpha gene, such as a collagen alpha 1(I) gene, or on a part thereof as described above. This term includes sequences corresponding to the entire sequence of the variant of the 3'UTR of a gene, i.e. the full length variant 3'UTR sequence of a gene, and sequences corresponding to a fragment of the variant 3'UTR sequence of a gene. A fragment in this context preferably consists of a continuous stretch of nucleotides corresponding to a continuous stretch of nucleotides in the full-length variant 3'UTR, which represents at least 20%, preferably at least 30%, more preferably at least 40%, more preferably at least 50%, even more preferably at least 60%, even more preferably at least 70%, even more preferably at least 80%, and most preferably at least 90% of the full-length variant 3'UTR. Such a fragment of a variant, in the sense of the present invention, is preferably a functional fragment of a variant as described herein.

Preferably, the at least one 5'UTR element and the at least one 3'UTR element act synergistically to increase protein production from the inventive mRNA as described above.

In a particularly preferred embodiment, the inventive mRNA comprising a coding region, encoding at least one antigenic peptide or protein of Rabies virus or a fragment, variant or derivative thereof, comprises a histone stem-loop sequence/structure. Such histone stem-loop sequences are preferably selected from histone stem-loop sequences as disclosed in WO 2012/019780, whose disclosure is incorporated herewith by reference.

A histone stem-loop sequence, suitable to be used within the present invention, is preferably selected from at least one of the following formulae (I) or (II):

(stem-loop sequence without stem bordering elements):

$$\underbrace{[N_{0-2}GN_{3-5}]}_{\text{stem1}}\underbrace{[N_{0-4}(U/T)N_{0-4}]}_{\text{loop}}\underbrace{[N_{3-5}CN_{0-2}]}_{\text{stem2}} \quad \text{formula (I)}$$

(stem-loop sequence with stem bordering elements):

$$\underbrace{N_{1-6}}_{\substack{\text{stem1}\\\text{bordering element}}}\underbrace{[N_{0-2}GN_{3-5}]}_{\text{stem1}}\underbrace{[N_{0-4}(U/T)N_{0-4}]}_{\text{loop}}\underbrace{[N_{3-5}CN_{0-2}]}_{\text{stem2}}\underbrace{N_{1-6}}_{\substack{\text{stem2}\\\text{bordering element}}} \quad \text{formula (II)}$$

wherein:
stem1 or stem2 bordering elements $N_{1-6}$ is a consecutive sequence of 1 to 6, preferably of 2 to 6, more preferably of 2 to 5, even more preferably of 3 to 5, most preferably of 4 to 5 or 5 N, wherein each N is independently from another selected from a nucleotide selected from A, U, T, G and C, or a nucleotide analogue thereof;

stem1 $[N_{0-2}GN_{3-5}]$ is reverse complementary or partially reverse complementary with element stem2, and is a consecutive sequence between of 5 to 7 nucleotides;
wherein $N_{0-2}$ is a consecutive sequence of 0 to 2, preferably of 0 to 1, more preferably of 1 N, wherein each N is independently from another selected from a nucleotide selected from A, U, T, G and C or a nucleotide analogue thereof;
wherein $N_{3-5}$ is a consecutive sequence of 3 to 5, preferably of 4 to 5, more preferably of 4 N, wherein each N is independently from another selected from a nucleotide selected from A, U, T, G and C or a nucleotide analogue thereof, and
wherein G is guanosine or an analogue thereof, and may be optionally replaced by a cytidine or an analogue thereof, provided that its complementary nucleotide cytidine in stem2 is replaced by guanosine;

loop sequence $[N_{0-4}(U/T)N_{0-4}]$ is located between elements stem1 and stem2, and is a consecutive sequence of 3 to 5 nucleotides, more preferably of 4 nucleotides;
wherein each $N_{0-4}$ is independent from another a consecutive sequence of 0 to 4, preferably of 1 to 3, more preferably of 1 to 2 N, wherein each N is independently from another selected from a nucleotide selected from A, U, T, G and C or a nucleotide analogue thereof; and
wherein U/T represents uridine, or optionally thymidine;

stem2 $[N_{3-5}CN_{0-2}]$ is reverse complementary or partially reverse complementary with element stem1, and is a consecutive sequence between of 5 to 7 nucleotides;
wherein $N_{3-5}$ is a consecutive sequence of 3 to 5, preferably of 4 to 5, more preferably of 4 N, wherein each N is independently from another selected from a nucleotide selected from A, U, T, G and C or a nucleotide analogue thereof;
wherein $N_{0-2}$ is a consecutive sequence of 0 to 2, preferably of 0 to 1, more preferably of 1 N, wherein each N is independently from another selected from a nucleotide selected from A, U, T, G or C or a nucleotide analogue thereof; and
wherein C is cytidine or an analogue thereof, and may be optionally replaced by a guanosine or an analogue thereof provided that its complementary nucleoside guanosine in stem1 is replaced by cytidine;

wherein
stem1 and stem2 are capable of base pairing with each other forming a reverse complementary sequence, wherein base pairing may occur between stem1 and stem2, e.g. by Watson-Crick base pairing of nucleotides A and U/T or G and C or by non-Watson-Crick base pairing e.g. wobble base pairing, reverse Watson-Crick base pairing, Hoogsteen base pairing, reverse Hoogsteen base pairing or are capable of base pairing with each other forming a partially reverse complementary sequence, wherein an incomplete base pairing may occur between stem1 and stem2, on the basis that one ore more bases in one stem do not have a complementary base in the reverse complementary sequence of the other stem.

According to a further preferred embodiment of the first inventive aspect, the inventive mRNA sequence may comprise at least one histone stem-loop sequence according to at least one of the following specific formulae (Ia) or (IIa):

(stem-loop sequence without stem bordering elements):

$$\underbrace{[N_{0-2}GN_{3-5}]}_{\text{stem1}}\underbrace{[N_{1-3}(U/T)N_{0-2}]}_{\text{loop}}\underbrace{[N_{3-5}CN_{0-1}]}_{\text{stem2}} \quad \text{formula (Ia)}$$

(stem-loop sequence with stem bordering elements):

$$\underbrace{N_{2-5}}_{\substack{\text{stem1}\\\text{bordering element}}}\underbrace{[N_{0-1}GN_{3-5}]}_{\text{stem1}}\underbrace{[N_{1-3}(U/T)N_{0-2}]}_{\text{loop}}\underbrace{[N_{3-5}CN_{0-1}]}_{\text{stem2}}\underbrace{N_{2-5}}_{\substack{\text{stem2}\\\text{bordering element}}} \quad \text{formula (IIa)}$$

wherein:

N, C, G, T and U are as defined above.

According to a further more particularly preferred embodiment of the first aspect, the inventive mRNA sequence may comprise at least one histone stem-loop sequence according to at least one of the following specific formulae (Ib) or (IIb):

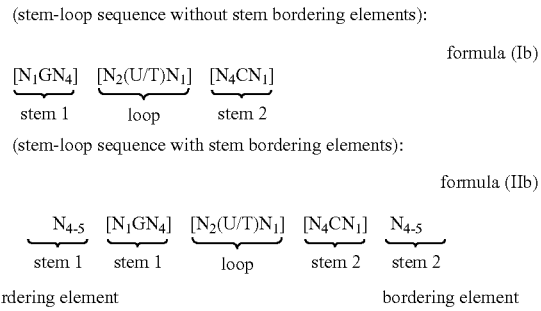

wherein:

N, C, G, T and U are as defined above.

A particular preferred histone stem-loop sequence is the sequence according to SEQ ID NO: 23 CAAAGGCTCTTTTCAGAGCCACCA or more preferably the corresponding RNA sequence of the nucleic acid sequence according to SEQ ID NO: 27 (CAAAGGCUC-UUUUCAGAGCCACCA SEQ ID NO: 27).

In a particular preferred embodiment of the first aspect of the present invention the inventive mRNA comprises additionally to the coding region encoding at least one antigenic peptide or protein of Rabies virus or a fragment, variant or derivative thereof, a poly(A) sequence, also called poly-A-tail, preferably at the 3'-terminus of the inventive mRNA. When present, such a poly(A) sequence comprises a sequence of about 25 to about 400 adenosine nucleotides, preferably a sequence of about 50 to about 400 adenosine nucleotides, more preferably a sequence of about 50 to about 300 adenosine nucleotides, even more preferably a sequence of about 50 to about 250 adenosine nucleotides, most preferably a sequence of about 60 to about 250 adenosine nucleotides. In this context the term "about" refers to a deviation of ±10% of the value(s) it is attached to. This poly(A) sequence is preferably located 3' of the coding region comprised in the inventive mRNA according to the first aspect of the present invention.

According to a further preferred embodiment the inventive mRNA can be modified by a sequence of at least 10 cytosines, preferably at least 20 cytosines, more preferably at least 30 cytosines (so-called "poly(C) sequence"). Particularly, the mRNA may contain a poly(C) sequence of typically about 10 to 200 cytosine nucleotides, preferably about 10 to 100 cytosine nucleotides, more preferably about 10 to 70 cytosine nucleotides or even more preferably about 20 to 50 or even 20 to 30 cytosine nucleotides. This poly(C) sequence is preferably located 3' of the coding region, more preferably 3' of an optional poly(A) sequence comprised in the inventive mRNA according to the first aspect of the present invention.

In this context the inventive mRNA sequence may comprise in a specific embodiment:

a.) a 5'-CAP structure, preferably m7GpppN;
b.) a coding region encoding at least one antigenic peptide or protein of Rabies virus, preferably derived from the glycoprotein G (RAV-G) of Rabies virus;
c.) a poly(A) sequence preferably comprising 64 adenosines; and
d.) optionally, a poly(C) sequence, preferably comprising 30 cytosines.

In a particularly preferred embodiment of the first aspect of the present invention the inventive mRNA comprising a coding region encoding at least one antigenic peptide or protein of Rabies virus or a fragment, variant or derivative thereof, comprises preferably in 5'- to 3'-direction:

a.) a 5'-CAP structure, preferably m7GpppN;
b.) a coding region encoding at least one antigenic peptide or protein of Rabies virus, preferably derived from the glycoprotein G (RAV-G) of Rabies virus;
c.) a poly(A) sequence preferably comprising 64 adenosines;
d.) optionally, a poly(C) sequence, preferably comprising 30 cytosines; and
e.) a histone-stem-loop, preferably comprising the corresponding RNA sequence of the nucleic acid sequence according to SEQ ID NO: 23.

In a further particularly preferred embodiment of the first aspect of the present invention the inventive mRNA comprising a coding region encoding at least one antigenic peptide or protein of Rabies virus or a fragment, variant or derivative thereof, comprises preferably in 5'- to 3'-direction:

a.) a 5'-CAP structure, preferably m7GpppN;
b.) a coding region encoding at least one antigenic peptide or protein of Rabies virus, preferably derived from the glycoprotein G (RAV-G) of Rabies virus;
c.) optionally, a 3'-UTR element derived from an alpha globin gene, preferably comprising the corresponding RNA sequence of the nucleic acid sequence according to SEQ ID NO. 22, a homolog, a fragment, or a variant thereof;
d.) a poly(A) sequence preferably comprising 64 adenosines;
e.) optionally, a poly(C) sequence, preferably comprising 30 cytosines; and
f.) a histone-stem-loop, preferably comprising the corresponding RNA sequence of the nucleic acid sequence according to SEQ ID NO: 23.

In another particular preferred embodiment the inventive mRNA encoding at least one antigenic peptide or protein of Rabies virus or a fragment, variant or derivative thereof, comprises preferably in 5'- to 3'-direction:

a.) a 5'-CAP structure, preferably m7GpppN;
b.) optionally, a 5'-UTR element derived from a TOP gene, preferably derived from the corresponding RNA sequence of the nucleic acid sequence according to SEQ ID NO. 16, a homolog, a fragment, or a variant thereof;
c.) a coding region encoding at least one antigenic peptide or protein of Rabies virus, preferably derived from the glycoprotein G (RAV-G) of Rabies virus;
d.) optionally, a 3'UTR element derived of a gene providing a stable mRNA, preferably derived from the corresponding RNA sequence of a nucleic acid sequence according to SEQ ID NO. 18, a homolog, a fragment, or a variant thereof;
e.) a poly(A) sequence preferably comprising 64 adenosines;
f.) optionally, a poly(C) sequence, preferably comprising 30 cytosines; and
g.) a histone-stem-loop, preferably comprising the corresponding RNA sequence of the nucleic acid sequence according to SEQ ID NO: 23.

The coding region might encode at least partially one of the amino acid sequences according to SEQ ID Nos. 1-10 or fragments, variants or derivatives thereof. Furthermore the coding region of the inventive mRNA may encode a combination of at least two of these amino acid sequences or a combination of fragments, variants or derivatives thereof.

Additionally the coding region might be or might comprise at least partially one of the sequences according to SEQ ID No. 11 to SEQ ID No. 15, or fragments, homologs or variants thereof. Furthermore, the mRNA might comprise a combination of at least two of these sequences or a combination of fragments, homologs or variants thereof.

For further improvement of the resistance to e.g. in vivo degradation (e.g. by an exo- or endo-nuclease), the inventive mRNA may be provided as a stabilized nucleic acid, e.g. in the form of a modified nucleic acid. According to a further embodiment of the invention it is therefore preferred that the inventive mRNA is stabilized, preferably by backbone modifications, sugar modifications and/or base modifications, more preferred stabilized by modification of the G/C-content. All of these modifications may be introduced into the inventive mRNA without impairing the mRNA's function to be translated into the antigenic function derived from the Rabies virus peptide or protein.

A backbone modification in the context of the present invention is preferably a modification in which phosphates of the backbone of the nucleotides contained in the inventive mRNA are chemically modified, e.g. anionic internucleoside linkage, N3'→P5' modifications, replacement of non-bridging oxygen atoms by boranes, neutral internucleoside linkage, amide linkage of the nucleosides, methylene(methylimino) linkages, formacetal and thioformacetal linkages, introduction of sulfonyl groups, or the like.

A sugar modification in the context of the present invention is preferably a chemical modification of the sugar of the nucleotides of the inventive mRNA, e.g. methylation of the ribose residue or the like.

According to another embodiment, the inventive mRNA may be modified and thus stabilized by modifying the G (guanosine)/C (cytosine) content of the mRNA, preferably of the coding region thereof.

Therein, the G/C content of the inventive mRNA, preferably of the coding region, is particularly increased compared to the G/C content of the coding region of its particular wild type coding sequence, i.e. the unmodified mRNA. However, the encoded amino acid sequence of the inventive mRNA is preferably not modified compared to the coded amino acid sequence of the particular wild type/unmodified mRNA.

The modification of the G/C-content of the inventive mRNA is based on the fact that RNA sequences having an increased G (guanosine)/C (cytosine) content are more stable than RNA sequences having an increased A (adenosine)/U (uracil) content. The codons of a coding sequence or a whole RNA might therefore be varied compared to the wild type coding sequence or mRNA, such that they include an increased amount of G/C nucleotides while the translated amino acid sequence is retained. In respect to the fact that several codons code for one and the same amino acid (so-called degeneration of the genetic code), the most favourable codons for the stability can be determined (so-called alternative codon usage). Preferably, the G/C content of the coding region of the inventive mRNA according to the invention is increased by at least 7%, more preferably by at least 15%, particularly preferably by at least 20%, compared to the G/C content of the coded region of the wild type RNA. According to a specific embodiment at least 5%, 10%, 20%, 30%, 40%, 50%, 60%, more preferably at least 70%, even more preferably at least 80% and most preferably at least 90%, 95% or even 100% of the substitutable codons in the region coding for a protein or peptide as defined herein or its fragment or variant thereof or the whole sequence of the wild type mRNA sequence or coding sequence are substituted, thereby increasing the G/C content of said sequence. In this context, it is particularly preferable to increase the G/C content of the inventive mRNA to the maximum (i.e. 100% of the substitutable codons), in particular in the coding region, compared to the wild type sequence.

According to a further preferred embodiment of the invention, the inventive mRNA is optimized for translation, preferably optimized for translation by replacing codons for less frequent tRNAs of a given amino acid by codons for more frequently occurring tRNAs of the respective amino acid. This is based on the finding that the translation efficiency is also determined by a different frequency in the occurrence of tRNAs in cells. Thus, if so-called "less frequent codons" are present in the inventive mRNA to an increased extent, the corresponding modified RNA is translated to a significantly poorer degree than in the case where codons coding for more frequent tRNAs are present. Preferably, the coding region of the inventive mRNA is modified compared to the corresponding region of the wild type RNA or coding sequence such that at least one codon of the wild type sequence which codes for a tRNA which is relatively rare or less frequent in the cell is exchanged for a codon which codes for a tRNA which is more or most frequent in the cell and carries the same amino acid as the relatively rare or less frequent tRNA. By this modification, the sequences of the inventive mRNA can be modified such that codons for which more frequently occurring tRNAs are available are inserted. In other words, according to the invention, by this modification all codons of the wild type sequence which code for a tRNA which is relatively rare in the cell can in each case be exchanged for a codon which codes for a respective tRNA which is relatively frequent in the cell and which, in each case, carries the same amino acid as the relatively rare tRNA. Furthermore, it is particularly preferable to link the sequential G/C content which is increased, in particular maximized, in the inventive mRNA with the "frequent" codons without modifying the amino acid sequence of the protein encoded by the coding region of the inventive mRNA or of the coding region. This preferred embodiment allows provision of a particularly efficiently translated and stabilized (modified) inventive mRNA.

Substitutions, additions or eliminations of bases are preferably carried out using a DNA matrix for preparation of the nucleic acid molecule by techniques of the well known site directed mutagenesis or with an oligonucleotide ligation. In such a process, for preparation of the at least one RNA of the inventive combination vaccine as defined herein a corresponding DNA molecule may be transcribed in vitro. This DNA matrix preferably comprises a suitable promoter, e.g. a T7 or SP6 promoter, for in vitro transcription, which is followed by the desired nucleotide sequence for the at least one RNA to be prepared and a termination signal for in vitro transcription. The DNA molecule, which forms the matrix of the at least one RNA of interest, may be prepared by fermentative proliferation and subsequent isolation as part of a plasmid which can be replicated in bacteria. Plasmids which may be mentioned as suitable for the present invention are e.g. the plasmids pT7Ts (GenBank accession number U26404; Lai et al., Development 1995, 121: 2349 to 2360), pGEM® series, e.g. pGEM®-1 (GenBank accession number X65300; from Promega) and pSP64 (GenBank accession number X65327); cf. also Mezei and Storts, Purification of PCR Products, in: Griffin and Griffin (ed.), PCR Technology: Current Innovation, CRC Press, Boca Raton, FL, 2001.

In a particularly preferred embodiment, the inventive mRNA sequence according to the first aspect of the present invention comprises, preferably in 5'- to 3'-direction:
 a) a 5'-CAP structure, as defined herein, preferably m7GpppN;
 b) a coding region, preferably with an increased or even maximized G/C content compared with the G/C content of the coding region of the wild type mRNA, encoding at least one antigenic peptide or protein derived from the glycoprotein G (RAV-G), the nucleoprotein (RAV-N), the posphoprotein (RAV-P), the matrix protein (RAV-M), or the RNA polymerase (RAV-L) of Rabies virus or a fragment, variant or derivative thereof;
 c) a 3'-UTR element as defined herein, preferably derived of a gene providing a stable mRNA, most preferably the corresponding RNA sequence of the nucleic acid sequence according to SEQ ID NO. 22, or a homolog, a fragment or variant thereof;
 d) a poly(A) sequence, preferably consisting of 64 adenosines
 e) optionally a poly(C) sequence, preferably consisting of 30 cytosines.
 f) at least one histone stem-loop sequence, preferably the corresponding RNA sequence of the nucleic acid sequence according to SEQ ID NO. 23.

Most preferably, the inventive mRNA sequence of that specific embodiment comprises the sequence modifications as shown in FIG. 1 (SEQ ID NO. 24).

In a further particularly preferred embodiment, the inventive mRNA sequence according to the first aspect of the present invention comprises preferably in 5' to 3' direction:
 a) a 5'-CAP structure, as defined herein, preferably m7GpppN;
 b) a 5'-UTR element as defined herein, preferably a 5'-UTR element which comprises or consists of a nucleic acid sequence which is derived from the 5'-UTR of a TOP gene, preferably the 5'-UTR of human ribosomal protein Large 32 lacking the 5' terminal oligopyrimidine tract according to SEQ ID NO. 16 or the corresponding RNA sequence; or a fragment, homolog or variant thereof;
 c) a coding region, preferably with an increased or even maximized G/C content compared with the G/C content of the coding region of the wild type mRNA, encoding at least one antigenic peptide or protein derived from the glycoprotein G (RAV-G), the nucleoprotein (RAV-N), the posphoprotein (RAV-P), the matrix protein (RAV-M), and the RNA polymerase (RAV-L) of Rabies virus or a fragment, variant or derivative thereof;
 d) a 3'-UTR element, preferably the 3'-UTR element of human albumin according to SEQ ID No. 18 or the corresponding RNA, or a homolog, a fragment or a variant thereof;
 e) a poly(A) sequence, preferably consisting of 64 adenosines
 f) optionally a poly(C) sequence, preferably consisting of 30 cytosines.
 g) at least one histone stem-loop sequence, preferably the corresponding RNA sequence of the nucleic acid sequence according to SEQ ID NO. 23.

Most preferably, the inventive mRNA of that specific embodiment comprises the sequence modifications as shown in FIG. 2 (SEQ ID NO. 25).

In an even more particularly preferred embodiment the inventive mRNA comprises or consists of the sequences shown in FIG. 1 or 2 according to SEQ ID Nos. 24 and 25.

In further specific embodiments, the mRNA according to the invention may further comprise an internal ribosome entry site (IRES) sequence or IRES-motif, which may separate several open reading frames, for example if the inventive mRNA encodes for two or more antigenic peptides or proteins. An IRES-sequence may be particularly helpful if the mRNA is a bi- or multicistronic mRNA.

Additionally, the inventive mRNA may be prepared using any method known in the art, including synthetic methods such as e.g. solid phase synthesis, as well as in vitro methods, such as in vitro transcription reactions.

According to one embodiment of the present invention the mRNA comprising a coding region, encoding at least one antigenic peptide or protein of Rabies virus or a fragment, variant or derivative thereof may be administered naked without being associated with any further vehicle, transfection or complexation agent for increasing the transfection efficiency and/or the immunostimulatory properties of the inventive mRNA or of further comprised nucleic acid.

In a preferred embodiment, the inventive mRNA may be formulated together with a cationic or polycationic compound and/or with a polymeric carrier. Accordingly, in a further embodiment of the invention it is preferred that the inventive mRNA or any other nucleic acid comprised in the inventive pharmaceutical composition or vaccine is associated with or complexed with a cationic or polycationic compound or a polymeric carrier, optionally in a weight ratio selected from a range of about 6:1 (w/w) to about 0.25:1 (w/w), more preferably from about 5:1 (w/w) to about 0.5:1 (w/w), even more preferably of about 4:1 (w/w) to about 1:1 (w/w) or of about 3:1 (w/w) to about 1:1 (w/w), and most preferably a ratio of about 3:1 (w/w) to about 2:1 (w/w) of mRNA or nucleic acid to cationic or polycationic compound and/or with a polymeric carrier; or optionally in a nitrogen/phosphate ratio of mRNA or nucleic acid to cationic or polycationic compound and/or polymeric carrier in the range of about 0.1-10, preferably in a range of about 0.3-4 or 0.3-1, and most preferably in a range of about 0.5-1 or 0.7-1, and even most preferably in a range of about 0.3-0.9 or 0.5-0.9.

Thereby, the inventive mRNA or any other nucleic acid comprised in the inventive pharmaceutical composition or vaccine can also be associated with a vehicle, transfection or complexation agent for increasing the transfection efficiency and/or the immunostimulatory properties of the inventive mRNA or of optionally comprised further included nucleic acids.

Cationic or polycationic compounds, being particularly preferred agents in this context include protamine, nucleoline, spermine or spermidine, or other cationic peptides or proteins, such as poly-L-lysine (PLL), poly-arginine, basic polypeptides, cell penetrating peptides (CPPs), including HIV-binding peptides, HIV-1 Tat (HIV), Tat-derived peptides, Penetratin, VP22 derived or analog peptides, HSV VP22 (Herpes simplex), MAP, KALA or protein transduction domains (PTDs), PpT620, prolin-rich peptides, arginine-rich peptides, lysine-rich peptides, MPG-peptide(s), Pep-1, L-oligomers, Calcitonin peptide(s), Antennapedia-derived peptides (particularly from *Drosophila* antennapedia), pAntp, plsl, FGF, Lactoferrin, Transportan, Buforin-2, Bac715-24, SynB, SynB(1), pVEC, hCT-derived peptides, SAP, or histones.

In this context protamine is particularly preferred.

Additionally, preferred cationic or polycationic proteins or peptides may be selected from the following proteins or peptides having the following total formula (III):

$$(Arg)_l;(Lys)_m;(His)_n;(Orn)_o;(Xaa)_x,\quad\text{(formula (III))}$$

wherein l+m+n+o+x=8-15, and l, m, n or o independently of each other may be any number selected from 0, 1, 2, 3, 4, 5, 6, 7, 8, 9, 10, 11, 12, 13, 14 or 15, provided that the overall content of Arg, Lys, His and Orn represents at least 50% of all amino acids of the oligopeptide; and Xaa may be any amino acid selected from native (=naturally occurring) or non-native amino acids except of Arg, Lys, His or Orn; and x may be any number selected from 0, 1, 2, 3 or 4, provided, that the overall content of Xaa does not exceed 50% of all amino acids of the oligopeptide. Particularly preferred cationic peptides in this context are e.g. $Arg_7$, $Arg_8$, $Arg_9$, $H_3R_9$, $R_9H_3$, $H_3R_9H_3$, $YSSR_9SSY$, $(RKH)_4$, $Y(RKH)_2R$, etc. In this context the disclosure of WO 2009/030481 is incorporated herewith by reference.

Further preferred cationic or polycationic compounds, which can be used as transfection or complexation agent may include cationic polysaccharides, for example chitosan, polybrene, cationic polymers, e.g. polyethyleneimine (PEI), cationic lipids, e.g. DOTMA: [1-(2,3-sioleyloxy)propyl)]-N,N,N-trimethylammonium chloride, DMRIE, di-C14-amidine, DOTIM, SAINT, DC-Chol, BGTC, CTAP, DOPC, DODAP, DOPE: Dioleyl phosphatidylethanol-amine, DOSPA, DODAB, DOIC, DMEPC, DOGS: Dioctadecylamidoglicylspermin, DIMRI: Dimyristo-oxypropyl dimethyl hydroxyethyl ammonium bromide, DOTAP: dioleoyloxy-3-(trimethylammonio)propane, DC-6-14: O,O-ditetradecanoyl-N-(α-trimethylammonioacetyl) diethanolamine chloride, CLIP1: rac-[(2,3-dioctadecyloxypropyl)(2-hydroxyethyl)]-dimethylammonium chloride, CLIP6: rac-[2(2,3-dihexadecyloxypropyl-oxymethyloxy)ethyl] trimethylammonium, CLIP9: rac-[2(2,3-dihexadecyloxypropyl-oxysuccinyloxy)ethyl]-trimethylammonium, oligofectamine, or cationic or polycationic polymers, e.g. modified polyaminoacids, such as β-aminoacid-polymers or reversed polyamides, etc., modified polyethylenes, such as PVP (poly(N-ethyl-4-vinylpyridinium bromide)), etc., modified acrylates, such as pDMAEMA (poly(dimethylaminoethyl methylacrylate)), etc., modified amidoamines such as pAMAM (poly(amidoamine)), etc., modified polybetaaminoester (PBAE), such as diamine end modified 1,4 butanediol diacrylate-co-5-amino-1-pentanol polymers, etc., dendrimers, such as polypropylamine dendrimers or pAMAM based dendrimers, etc., polyimine(s), such as PEI: poly(ethyleneimine), poly(propyleneimine), etc., polyallylamine, sugar backbone based polymers, such as cyclodextrin based polymers, dextran based polymers, chitosan, etc., silan backbone based polymers, such as PMOXA-PDMS copolymers, etc., blockpolymers consisting of a combination of one or more cationic blocks (e.g. selected from a cationic polymer as mentioned above) and of one or more hydrophilic or hydrophobic blocks (e.g. polyethyleneglycole); etc.

A polymeric carrier used according to the invention might be a polymeric carrier formed by disulfide-crosslinked cationic components. The disulfide-crosslinked cationic components may be the same or different from each other. The polymeric carrier can also contain further components. It is also particularly preferred that the polymeric carrier used according to the present invention comprises mixtures of cationic peptides, proteins or polymers and optionally further components as defined herein, which are crosslinked by disulfide bonds as described herein. In this context the disclosure of WO 2012/013326 is incorporated herewith by reference.

In this context the cationic components, which form basis for the polymeric carrier by disulfide-crosslinkage, are typically selected from any suitable cationic or polycationic peptide, protein or polymer suitable for this purpose, particular any cationic or polycationic peptide, protein or polymer capable to complex an mRNA or a nucleic acid as defined according to the present invention, and thereby preferably condensing the mRNA or the nucleic acid. The cationic or polycationic peptide, protein or polymer, is preferably a linear molecule, however, branched cationic or polycationic peptides, proteins or polymers may also be used.

Every disulfide-crosslinking cationic or polycationic protein, peptide or polymer of the polymeric carrier, which may be used to complex the inventive mRNA or any further nucleic acid comprised in the inventive pharmaceutical composition or vaccine contains at least one —SH moiety, most preferably at least one cysteine residue or any further chemical group exhibiting an —SH moiety, capable to form a disulfide linkage upon condensation with at least one further cationic or polycationic protein, peptide or polymer as cationic component of the polymeric carrier as mentioned herein.

As defined above, the polymeric carrier, which may be used to complex the inventive mRNA or any further nucleic acid comprised in the inventive pharmaceutical composition or vaccine may be formed by disulfide-crosslinked cationic (or polycationic) components.

Preferably, such cationic or polycationic peptides or proteins or polymers of the polymeric carrier, which comprise or are additionally modified to comprise at least one —SH moiety, are selected from, proteins, peptides and polymers as defined above for complexation agent.

In a further particular embodiment, the polymeric carrier which may be used to complex the inventive mRNA or any further nucleic acid comprised in the inventive pharmaceutical composition or vaccine may be selected from a polymeric carrier molecule according to generic formula (IV):

$$L-P^1-S-[S-P^2-S]_n-S-P^3-L\quad\text{formula (IV)}$$

wherein, $P^1$ and $P^3$ are different or identical to each other and represent a linear or branched hydrophilic polymer chain, each $P^1$ and $P^3$ exhibiting at least one —SH-moiety, capable to form a disulfide linkage upon condensation with component $P^2$, or alternatively with (AA), $(AA)_x$, or $[(AA)_x]z$ if such components are used as a linker between $P^1$ and $P^2$ or $P^3$ and $P^2$) and/or with further components (e.g. (AA), $(AA)_x$, $[(AA)_x]z$ or L), the linear or branched hydrophilic polymer chain selected independent from each other from polyethylene glycol (PEG), poly-N-(2-hydroxypropyl)methacrylamide, poly-2-(methacryloyloxy)ethyl phosphorylcholines, poly(hydroxyalkyl L-asparagine), poly(2-(methacryloyloxy)ethyl phosphorylcholine), hydroxyethylstarch or poly(hydroxyalkyl L-glutamine), wherein the hydrophilic polymer chain exhibits a molecular weight of about 1 kDa to about 100 kDa, preferably of about 2 kDa to about 25 kDa; or more preferably of about 2 kDa to about 10 kDa, e.g. about 5 kDa to about 25 kDa or 5 kDa to about 10 kDa;

$P^2$ is a cationic or polycationic peptide or protein, e.g. as defined above for the polymeric carrier formed by disulfide-crosslinked cationic components, and preferably having a length of about 3 to about 100 amino acids, more preferably having a length of about 3 to about 50 amino acids, even more preferably having a length of about 3 to about 25 amino acids, e.g. a length of about 3 to 10, 5 to 15, 10 to 20 or 15 to 25 amino acids, more preferably a length of about 5 to about 20 and even more preferably a length of about 10 to about 20; or is a cationic or polycationic polymer, e.g. as defined above for the polymeric carrier formed by disulfide-crosslinked cationic components, typically having a molecular weight of about 0.5 kDa to about 30 kDa, including a molecular weight of about 1 kDa to about 20 kDa, even more preferably of about 1.5 kDa to about 10 kDa, or having a molecular weight of about 0.5 kDa to about 100 kDa, including a molecular weight of about 10 kDa to about 50 kDa, even more preferably of about 10 kDa to about 30 kDa;

each $P^2$ exhibiting at least two —SH-moieties, capable to form a disulfide linkage upon condensation with further components $P^2$ or component(s) $P^1$ and/or $P^3$ or alternatively with further components (e.g. (AA), $(AA)_x$, or $[(AA)_x]z$);

—S—S— is a (reversible) disulfide bond (the brackets are omitted for better readability), wherein S preferably represents sulphur or a —SH carrying moiety, which has formed a (reversible) disulfide bond. The (reversible) disulfide bond is preferably formed by condensation of —SH-moieties of either components $P^1$ and $P^2$, $P^2$ and $P^2$, or $P^2$ and $P^3$, or optionally of further components as defined herein (e.g. L, (AA), $(AA)_x$, $[(AA)_x]z$, etc); The —SH-moiety may be part of the structure of these components or added by a modification as defined below;

L is an optional ligand, which may be present or not, and may be selected independent from the other from RGD, Transferrin, Folate, a signal peptide or signal sequence, a localization signal or sequence, a nuclear localization signal or sequence (NLS), an antibody, a cell penetrating peptide, (e.g. TAT or KALA), a ligand of a receptor (e.g. cytokines, hormones, growth factors etc), small molecules (e.g. carbohydrates like mannose or galactose or synthetic ligands), small molecule agonists, inhibitors or antagonists of receptors (e.g. RGD peptidomimetic analogues), or any further protein as defined herein, etc.;

n is an integer, typically selected from a range of about 1 to 50, preferably from a range of about 1, 2 or 3 to 30, more preferably from a range of about 1, 2, 3, 4, or 5 to 25, or a range of about 1, 2, 3, 4, or 5 to 20, or a range of about 1, 2, 3, 4, or 5 to 15, or a range of about 1, 2, 3, 4, or 5 to 10, including e.g. a range of about 4 to 9, 4 to 10, 3 to 20, 4 to 20, 5 to 20, or 10 to 20, or a range of about 3 to 15, 4 to 15, 5 to 15, or 10 to 15, or a range of about 6 to 11 or 7 to 10. Most preferably, n is in a range of about 1, 2, 3, 4, or 5 to 10, more preferably in a range of about 1, 2, 3, or 4 to 9, in a range of about 1, 2, 3, or 4 to 8, or in a range of about 1, 2, or 3 to 7.

In this context the disclosure of WO 2011/026641 is incorporated herewith by reference. Each of hydrophilic polymers $P^1$ and $P^3$ typically exhibits at least one —SH-moiety, wherein the at least one —SH-moiety is capable to form a disulfide linkage upon reaction with component $P^2$ or with component (AA) or $(AA)_x$, if used as linker between $P^1$ and $P^2$ or $P^3$ and $P^2$ as defined below and optionally with a further component, e.g. L and/or (AA) or $(AA)_x$, e.g. if two or more —SH-moieties are contained. The following subformulae "$P^1$—S—S—$P^2$" and "$P^2$—S—S—$P^3$" within generic formula (V) above (the brackets are omitted for better readability), wherein any of S, $P^1$ and $P^3$ are as defined herein, typically represent a situation, wherein one-SH-moiety of hydrophilic polymers $P^1$ and $P^3$ was condensed with one —SH-moiety of component $P^2$ of generic formula (V) above, wherein both sulphurs of these —SH-moieties form a disulfide bond —S—S— as defined herein in formula (V). These —SH-moieties are typically provided by each of the hydrophilic polymers $P^1$ and $P^3$, e.g. via an internal cysteine or any further (modified) amino acid or compound which carries a —SH moiety. Accordingly, the subformulae "$P^1$—S—S—$P^2$" and "$P^2$—S—S—$P^3$" may also be written as "$P^1$-Cys-Cys-$P^2$" and "$P^2$-Cys-Cys-$P^3$", if the —SH— moiety is provided by a cysteine, wherein the term Cys-Cys represents two cysteines coupled via a disulfide bond, not via a peptide bond. In this case, the term "—S—S—" in these formulae may also be written as "—S-Cys", as "-Cys-S" or as "-Cys-Cys-". In this context, the term "-Cys-Cys-" does not represent a peptide bond but a linkage of two cysteines via their —SH-moieties to form a disulfide bond. Accordingly, the term "-Cys-Cys-" also may be understood generally as "-(Cys-S)—(S-Cys)-", wherein in this specific case S indicates the sulphur of the —SH-moiety of cysteine. Likewise, the terms "—S-Cys" and "—Cys-S" indicate a disulfide bond between a —SH containing moiety and a cysteine, which may also be written as "—S—(S-Cys)" and "-(Cys-S)—S". Alternatively, the hydrophilic polymers $P^1$ and $P^3$ may be modified with a —SH moiety, preferably via a chemical reaction with a compound carrying a —SH moiety, such that each of the hydrophilic polymers $P^1$ and $P^3$ carries at least one such —SH moiety. Such a compound carrying a —SH moiety may be e.g. an (additional) cysteine or any further (modified) amino acid, which carries a —SH moiety. Such a compound may also be any non-amino compound or moiety, which contains or allows to introduce a —SH moiety into hydrophilic polymers $P^1$ and $P^3$ as defined herein. Such non-amino compounds may be attached to the hydrophilic polymers $P^1$ and $P^3$ of formula (VI) of the polymeric carrier according to the present invention via chemical reactions or binding of compounds, e.g. by binding of a 3-thio propionic acid or thioimolane, by amide formation (e.g. carboxylic acids, sulphonic acids, amines, etc), by Michael addition (e.g maleinimide moieties, □,□ unsaturated carbonyls, etc), by click chemistry (e.g. azides or alkines), by alkene/alkine methatesis (e.g. alkenes or alkines), imine or hydrozone formation (aldehydes or ketons, hydrazins, hydroxylamins, amines), complexation reactions (avidin, biotin, protein G) or components which allow Sn-type substitution reactions (e.g halogenalkans, thiols, alcohols, amines, hydrazines, hydrazides, sulphonic acid esters, oxyphosphonium salts) or other chemical moieties which can be utilized in the attachment of further components. A particularly preferred PEG derivate in this context is alpha-Methoxy-omega-mercapto poly(ethylene glycol). In each case, the SH-moiety, e.g. of a cysteine or of any further (modified) amino acid or compound, may be present at the terminal ends or internally at any position of hydrophilic polymers $P^1$ and $P^3$. As defined herein, each of hydrophilic polymers $P^1$ and $P^3$ typically exhibits at least one —SH— moiety preferably at one terminal end, but may also contain two or even more —SH-moieties, which may be used to additionally attach further components as defined herein, preferably further functional peptides or proteins e.g. a ligand, an amino acid component (AA) or $(AA)_x$, antibodies, cell penetrating peptides or enhancer peptides (e.g. TAT, KALA), etc.

In this context it is particularly preferred that the inventive mRNA is complexed at least partially with a cationic or polycationic compound and/or a polymeric carrier, preferably cationic proteins or peptides. In this context the disclosure of WO 2010/037539 and WO 2012/113513 is incorporated herewith by reference. Partially means that only a part of the inventive mRNA is complexed with a cationic compound and that the rest of the inventive mRNA is (comprised in the inventive pharmaceutical composition or vaccine) in uncomplexed form ("free"). Preferably the ratio of complexed mRNA to:free mRNA (in the inventive pharmaceutical composition or vaccine) is selected from a range of about 5:1 (w/w) to about 1:10 (w/w), more preferably from a range of about 4:1 (w/w) to about 1:8 (w/w), even more preferably from a range of about 3:1 (w/w) to about 1:5 (w/w) or 1:3 (w/w), and most preferably the ratio of complexed mRNA to free mRNA in the inventive pharmaceutical composition or vaccine is selected from a ratio of about 1:1 (w/w).

The complexed mRNA in the inventive pharmaceutical composition or vaccine, is preferably prepared according to a first step by complexing the inventive mRNA with a cationic or polycationic compound and/or with a polymeric carrier, preferably as defined herein, in a specific ratio to form a stable complex. In this context, it is highly preferable, that no free cationic or polycationic compound or polymeric carrier or only a negligibly small amount thereof remains in the component of the complexed mRNA after complexing the mRNA. Accordingly, the ratio of the mRNA and the cationic or polycationic compound and/or the polymeric carrier in the component of the complexed mRNA is typically selected in a range that the mRNA is entirely complexed and no free cationic or polycationic compound or polymeric carrier or only a negligibly small amount thereof remains in the composition.

Preferably the ratio of the mRNA to the cationic or polycationic compound and/or the polymeric carrier, preferably as defined herein, is selected from a range of about 6:1 (w/w) to about 0.25:1 (w/w), more preferably from about 5:1 (w/w) to about 0.5:1 (w/w), even more preferably of about 4:1 (w/w) to about 1:1 (w/w) or of about 3:1 (w/w) to about 1:1 (w/w), and most preferably a ratio of about 3:1 (w/w) to about 2:1 (w/w). Alternatively, the ratio of the mRNA to the cationic or polycationic compound and/or the polymeric carrier, preferably as defined herein, in the component of the complexed mRNA, may also be calculated on the basis of the nitrogen/phosphate ratio (N/P-ratio) of the entire complex. In the context of the present invention, an N/P-ratio is preferably in the range of about 0.1-10, preferably in a range of about 0.3-4 and most preferably in a range of about 0.5-2 or 0.7-2 regarding the ratio of mRNA:cationic or polycationic compound and/or polymeric carrier, preferably as defined herein, in the complex, and most preferably in a range of about 0.7-1.5, 0.5-1 or 0.7-1, and even most preferably in a range of about 0.3-0.9 or 0.5-0.9, preferably provided that the cationic or polycationic compound in the complex is a cationic or polycationic cationic or polycationic protein or peptide and/or the polymeric carrier as defined above. In this specific embodiment the complexed mRNA is also encompassed in the term "adjuvant component".

In a further aspect the invention provides for a composition comprising a plurality or more than one, preferably 2 to 10, more preferably 2 to 5, most preferably 2 to 4 of the inventive mRNA sequences as defined herein. These inventive compositions comprise more than one inventive mRNA sequences, preferably encoding different peptides or proteins which comprise preferably different pathogenic antigens or fragments, variants or derivatives thereof. Particularly preferred in this context is that at least one mRNA sequence encodes at least one antigenic peptide or protein derived from glycoprotein G (RAV-G) of Rabies virus and that at least one mRNA sequence encodes at least one antigenic peptide or protein derived from another antigen of Rabies virus, particularly of nucleoprotein N (RAV-N).

Accordingly, in a further particular preferred aspect, the present invention also provides a pharmaceutical composition, comprising at least one inventive mRNA sequence as defined herein or an inventive composition comprising a plurality of inventive mRNA sequences as defined herein and optionally a pharmaceutically acceptable carrier and/or vehicle.

As a first ingredient, the inventive pharmaceutical composition comprises at least one inventive mRNA sequence as defined herein.

As a second ingredient the inventive pharmaceutical composition may optional comprise at least one additional pharmaceutically active component. A pharmaceutically active component in this connection is a compound that has a therapeutic effect to heal, ameliorate or prevent a particular indication or disease as mentioned herein, preferably rabies. Such compounds include, without implying any limitation, peptides or proteins, preferably as defined herein, nucleic acids, preferably as defined herein, (therapeutically active) low molecular weight organic or inorganic compounds (molecular weight less than 5000, preferably less than 1000), sugars, antigens or antibodies, preferably as defined herein, therapeutic agents already known in the prior art, antigenic cells, antigenic cellular fragments, cellular fractions; cell wall components (e.g. polysaccharides), modified, attenuated or de-activated (e.g. chemically or by irradiation) pathogens (virus, bacteria etc.), adjuvants, preferably as defined herein, etc. Particularly preferred in this context are rabies vaccines, e.g. "Tollwutimpfstoff (HDC) inaktiviert" or Rabipur, or rabies immune globulines, e.g. Merieux P or Berirab.

The inventive pharmaceutical composition may be administered orally, parenterally, by inhalation spray, topically, rectally, nasally, buccally, vaginally or via an implanted reservoir. The term parenteral as used herein includes subcutaneous, intravenous, intramuscular, intraarticular, intra-synovial, intrasternal, intrathecal, intrahepatic, intralesional, intracranial, transdermal, intradermal, intrapulmonal, intraperitoneal, intracardial, intraarterial, and sublingual injection or infusion techniques.

Particularly preferred is intradermal and intramuscular injection. Sterile injectable forms of the inventive pharmaceutical compositions may be aqueous or oleaginous suspension. These suspensions may be formulated according to techniques known in the art using suitable dispersing or wetting agents and suspending agents.

Preferably, the inventive vaccine may be administered by conventional needle injection or needle-free jet injection. In a preferred embodiment the inventive pharmaceutical composition may be administered by jet injection as defined herein, preferably intramuscularly or intradermally, more preferably intradermally.

According to a specific embodiment, the inventive pharmaceutical composition may comprise an adjuvant. In this context, an adjuvant may be understood as any compound, which is suitable to initiate or increase an immune response of the innate immune system, i.e. a non-specific immune response. With other words, when administered, the inventive pharmaceutical composition preferably elicits an innate immune response due to the adjuvant, optionally contained therein. Preferably, such an adjuvant may be selected from an adjuvant known to a skilled person and suitable for the present case, i.e. supporting the induction of an innate immune response in a mammal, e.g. an adjuvant protein as defined above or an adjuvant as defined in the following.

Particularly preferred as adjuvants suitable for depot and delivery are cationic or polycationic compounds as defined above for the inventive mRNA sequence as vehicle, transfection or complexation agent.

Furthermore, the inventive pharmaceutical composition may comprise one or more additional adjuvants which are suitable to initiate or increase an immune response of the innate immune system, i.e. a non-specific immune response, particularly by binding to pathogen-associated molecular patterns (PAMPs). With other words, when administered, the pharmaceutical composition or vaccine preferably elicits an innate immune response due to the adjuvant, optionally contained therein. Preferably, such an adjuvant may be selected from an adjuvant known to a skilled person and suitable for the present case, i.e. supporting the induction of an innate immune response in a mammal, e.g. an adjuvant protein as defined above or an adjuvant as defined in the following. According to one embodiment such an adjuvant may be selected from an adjuvant as defined above.

Also such an adjuvant may be selected from any adjuvant known to a skilled person and suitable for the present case, i.e. supporting the induction of an innate immune response in a mammal and/or suitable for depot and delivery of the components of the inventive pharmaceutical composition or vaccine. Preferred as adjuvants suitable for depot and delivery are cationic or polycationic compounds as defined above. Likewise, the adjuvant may be selected from the group consisting of, e.g., cationic or polycationic compounds as defined above, from chitosan, TDM, MDP, muramyl dipeptide, pluronics, alum solution, aluminium hydroxide, ADJUMER™ (polyphosphazene); aluminium phosphate gel; glucans from algae; algammulin; aluminium hydroxide gel (alum); highly protein-adsorbing aluminium hydroxide gel; low viscosity aluminium hydroxide gel; AF or SPT (emulsion of squalane (5%), Tween 80 (0.2%), Pluronic L121 (1.25%), phosphate-buffered saline, pH 7.4); AVRIDINE™ (propanediamine); BAY R1005™ ((N-(2-deoxy-2-L-leucylaminob-D-glucopyranosyl)-N-octadecyl-dodecanoyl-amide hydroacetate); CALCITRIOL™ (1-alpha, 25-dihydroxy-vitamin D3); calcium phosphate gel; CAP™ (calcium phosphate nanoparticles); cholera holotoxin, cholera-toxin-A1-protein-A-D-fragment fusion protein, sub-unit B of the cholera toxin; CRL 1005 (block copolymer P1205); cytokine-containing liposomes; DDA (dimethyldioctadecylammonium bromide); DHEA (dehydroepiandrosterone); DMPC (dimyristoylphosphatidylcholine); DMPG (dimyristoylphosphatidylglycerol); DOC/alum complex (deoxycholic acid sodium salt); Freund's complete adjuvant; Freund's incomplete adjuvant; gamma inulin; Gerbu adjuvant (mixture of: i) N-acetylglucosaminyl-(P1-4)-N-acetylmuramyl-L-alanyl-D35 glutamine (GMDP), ii) dimethyldioctadecylammonium chloride (DDA), iii) zinc-L-proline salt complex (ZnPro-8); GM-CSF); GMDP (N-acetylglucosaminyl-(b1-4)-N-acetylmuramyl-L47 alanyl-D-isoglutamine); imiquimod (1-(2-methypropyl)-1H-imidazo[4,5-c]quinoline-4-amine); ImmTher™ (N-acetylglucosaminyl-N-acetylmuramyl-L-Ala-D-isoGlu-L-Ala-glycerol dipalmitate); DRVs (immunoliposomes prepared from dehydration-rehydration vesicles); interferongamma; interleukin-1beta; interleukin-2; interleukin-7; interleukin-12; ISCOMS™; ISCOPREP 7.0.3.™; liposomes; LOXORIBINE™ (7-allyl-8-oxoguanosine); LT 5 oral adjuvant (*E. coli* labile enterotoxin-protoxin); microspheres and microparticles of any composition; MF59™; (squalenewater emulsion); MONTANIDE ISA 51™ (purified incomplete Freund's adjuvant); MONTANIDE ISA 720™ (metabolisable oil adjuvant); MPL™ (3-Q-desacyl-4'-monophosphoryl lipid A); MTP-PE and MTP-PE liposomes ((N-acetyl-L-alanyl-D-isoglutaminyl-L-alanine-2-(1,2-dipalmitoyl-sn-glycero-3-(hydroxyphosphoryloxy))-ethylamide, monosodium salt); MURAMETIDE™ (Nac-Mur-L-Ala-D-Gln-OCH3); MURAPALMITINE™ and DMURAPALMITINE™ (Nac-Mur-L-Thr-D-isoGIn-sn-glyceroldipalmitoyl); NAGO (neuraminidase-galactose oxidase); nanospheres or nanoparticles of any composition; NISVs (non-ionic surfactant vesicles); PLEURAN™ (□β-glucan); PLGA, PGA and PLA (homo- and co-polymers of lactic acid and glycolic acid; microspheres/nanospheres); PLURONIC L121™; PMMA (polymethylmethacrylate); PODDS™ (proteinoid microspheres); polyethylene carbamate derivatives; poly-rA: poly-rU (polyadenylic acid-polyuridylic acid complex); polysorbate 80 (Tween 80); protein cochleates (Avanti Polar Lipids, Inc., Alabaster, AL); STIMULON™ (QS-21); Quil-A (Quil-A saponin); S-28463 (4-amino-otec-dimethyl-2-ethoxymethyl-1H-imidazo[4,5-c]quinoline-1-ethanol); SAF-1™ ("Syntex adjuvant formulation"); Sendai proteoliposomes and Sendai containing lipid matrices; Span-85 (sorbitan trioleate); Specol (emulsion of Marcol 52, Span 85 and Tween 85); squalene or Robane® (2,6,10,15,19,23-hexamethyltetracosan and 2,6,10,15,19,23-hexamethyl-2,6,10,14,18,22-tetracosahexane); stearyltyrosine (octadecyltyrosine hydrochloride); Theramid® (N-acetylglucosaminyl-N-acetylmuramyl-L-Ala-D-isoGlu-L-Aladipalmitoxypropylamide); Theronyl-MDP (Termurtide™ or [thr 1]-MDP; N-acetylmuramyl-Lthreonyl-D-isoglutamine); Ty particles (Ty-VLPs or virus-like particles); Walter-Reed liposomes (liposomes containing lipid A adsorbed on aluminium hydroxide), and lipopeptides, including Pam3Cys, in particular aluminium salts, such as Adju-phos, Alhydrogel, Rehydragel; emulsions, including CFA, SAF, IFA, MF59, Provax, TiterMax, Montanide, Vaxfectin; copolymers, including Optivax (CRL1005), L121, Poloaxmer4010), etc.; liposomes, including Stealth, cochleates, including BIORAL; plant derived adjuvants, including QS21, Quil A, Iscomatrix, ISCOM; adjuvants suitable for costimulation including Tomatine, biopolymers, including PLG, PMM, Inulin, microbe derived adjuvants, including Romurtide, DETOX, MPL, CWS, Mannose, CpG nucleic acid sequences, CpG7909, ligands of human TLR 1-10, ligands of murine TLR 1-13, ISS-1018, IC31, Imidazoquinolines, Ampligen, Ribi529, IMOxine, IRIVs, VLPs, cholera toxin, heat-labile toxin, Pam3Cys, Flagellin, GPI anchor, LNFPIII/Lewis X, antimicrobial peptides, UC-1V150, RSV fusion protein, cdiGMP; and adjuvants suitable as antagonists including CGRP neuropeptide.

Particularly preferred, an adjuvant may be selected from adjuvants, which support induction of a Th1-immune response or maturation of naïve T-cells, such as GM-CSF, IL-12, IFNg, any immunostimulatory nucleic acid as defined above, preferably an immunostimulatory RNA, CpG DNA, etc.

In a further preferred embodiment it is also possible that the inventive pharmaceutical composition contains besides the antigen-providing mRNA further components which are selected from the group comprising: further antigens or further antigen-providing nucleic acids; a further immunotherapeutic agent; one or more auxiliary substances; or any further compound, which is known to be immunostimulating due to its binding affinity (as ligands) to human Toll-like receptors; and/or an adjuvant nucleic acid, preferably an immunostimulatory RNA (isRNA).

The inventive pharmaceutical composition can additionally contain one or more auxiliary substances in order to increase its immunogenicity or immunostimulatory capacity, if desired. A synergistic action of the inventive mRNA sequence as defined herein and of an auxiliary substance, which may be optionally contained in the inventive pharmaceutical composition, is preferably achieved thereby. Depending on the various types of auxiliary substances, various mechanisms can come into consideration in this respect. For example, compounds that permit the maturation of dendritic cells (DCs), for example lipopolysaccharides, TNF-alpha or CD40 ligand, form a first class of suitable auxiliary substances. In general, it is possible to use as auxiliary substance any agent that influences the immune system in the manner of a "danger signal" (LPS, GP96, etc.) or cytokines, such as GM-CFS, which allow an immune response to be enhanced and/or influenced in a targeted manner. Particularly preferred auxiliary substances are cytokines, such as monokines, lymphokines, interleukins or chemokines, that further promote the innate immune response, such as IL-1, IL-2, IL-3, IL-4, IL-5, IL-6, IL-7, IL-8, IL-9, IL-10, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IFN-alpha, IFN-beta, IFN-gamma, GM-CSF, G-CSF, M-CSF, LT-beta or TNF-alpha, growth factors, such as hGH.

Further additives which may be included in the inventive pharmaceutical composition are emulsifiers, such as, for example, Tween®; wetting agents, such as, for example, sodium lauryl sulfate; colouring agents; taste-imparting agents, pharmaceutical carriers; tablet-forming agents; stabilizers; antioxidants; preservatives.

The inventive pharmaceutical composition can also additionally contain any further compound, which is known to be immunostimulating due to its binding affinity (as ligands) to human Toll-like receptors TLR1, TLR2, TLR3, TLR4, TLR5, TLR6, TLR7, TLR8, TLR9, TLR10, or due to its binding affinity (as ligands) to murine Toll-like receptors TLR1, TLR2, TLR3, TLR4, TLR5, TLR6, TLR7, TLR8, TLR9, TLR10, TLR11, TLR12 or TLR13.

In this context it is particularly preferred that the optionally comprised adjuvant component comprises the same inventive mRNA as comprised in the inventive pharmaceutical composition as antigen-providing mRNA e.g. mRNA coding for an antigenic peptide or protein of Rabies virus or fragments, variants or derivatives thereof.

Despite, the inventive pharmaceutical composition may comprise further components for facilitating administration and uptake of components of the pharmaceutical composition. Such further components may be an appropriate carrier or vehicle, additional adjuvants for supporting any immune response, antibacterial and/or antiviral agents.

Accordingly, in a further embodiment, the inventive pharmaceutical composition furthermore comprises a pharmaceutically acceptable carrier and/or vehicle.

Such a pharmaceutically acceptable carrier typically includes the liquid or non-liquid basis of a composition comprising the components of the inventive pharmaceutical composition. If the composition is provided in liquid form, the carrier will typically be pyrogen-free water; isotonic saline or buffered (aqueous) solutions, e.g. phosphate, citrate etc. buffered solutions. The injection buffer may be hypertonic, isotonic or hypotonic with reference to the specific reference medium, i.e. the buffer may have a higher, identical or lower salt content with reference to the specific reference medium, wherein preferably such concentrations of the afore mentioned salts may be used, which do not lead to damage of cells due to osmosis or other concentration effects. Reference media are e.g. liquids occurring in "in vivo" methods, such as blood, lymph, cytosolic liquids, or other body liquids, or e.g. liquids, which may be used as reference media in "in vitro" methods, such as common buffers or liquids. Such common buffers or liquids are known to a skilled person. Ringer-Lactate solution is particularly preferred as a liquid basis.

However, one or more compatible solid or liquid fillers or diluents or encapsulating compounds, which are suitable for administration to a patient to be treated, may be used as well for the pharmaceutical composition according to the invention. The term "compatible" as used here means that these constituents of the inventive pharmaceutical composition are capable of being mixed with the components of the inventive pharmaceutical composition in such a manner that no interaction occurs which would substantially reduce the pharmaceutical effectiveness of the pharmaceutical composition under typical use conditions.

A further component of the inventive pharmaceutical composition may be an immunotherapeutic agent that can be selected from immunoglobulins, preferably IgGs, monoclonal or polyclonal antibodies, polyclonal serum or sera, etc, most preferably immunoglobulins directed against a Rabies virus, eg. Merieux P or Berirab. Preferably, such a further immunotherapeutic agent may be provided as a peptide/protein or may be encoded by a nucleic acid, preferably by a DNA or an RNA, more preferably an mRNA. Such an immunotherapeutic agent allows providing passive vaccination additional to active vaccination triggered by the inventive antigen-providing mRNA.

Furthermore, in a specific embodiment, additionally to the antigen-providing mRNA further antigens can be included in the inventive pharmaceutical composition and are typically substances such as cells, cell lysates, viruses, attenuated viruses, inactivated viruses, proteins, peptides, nucleic acids or other bio- or macromolecules or fragments thereof. Preferably, antigens may be proteins and peptides or fragments thereof, such as epitopes of those proteins or peptides, preferably having 5 to 15, more preferably 6 to 9, amino acids. Particularly, said proteins, peptides or epitopes may be derived from Glycoprotein G(RAV-G), nucleoprotein N (RAV-N), phosphoprotein P (RAV-P), matrix protein (RAV-M) or RNA polymerase L (RAV-L) of Rabies virus or from fragments, variants or derivatives thereof. Further, antigens may also comprise any other biomolecule, e.g., lipids, carbohydrates, etc. Preferably, the antigen is a protein or (poly-) peptide antigen, a nucleic acid, a nucleic acid encoding a protein or (poly-) peptide antigen, a polysaccharide antigen, a polysaccharide conjugate antigen, a lipid antigen, a glycolipid antigen, a carbohydrate antigen, a bacterium, a cell (vaccine), or killed or attenuated viruses. Particularly preferred in this context is the addition of rabies vaccines comprising inactivated virus, as e.g. Rabipur comprising inactivated Rabies virus strain Flury-LEP or "inaktivierter (HDC) Tollwutimpfstoff" comprising inactivated Rabies virus strain WISTAR PM/WI 38-1503-3M.

The inventive pharmaceutical composition or vaccine as defined herein may furthermore comprise further additives or additional compounds. Further additives which may be included in the pharmaceutical composition are emulsifiers, such as, for example, Tween®; wetting agents, such as, for example, sodium lauryl sulfate; colouring agents; taste-imparting agents, pharmaceutical carriers; tablet-forming agents; stabilizers; antioxidants; preservatives, RNase inhibitors and/or an anti-bacterial agent or an anti-viral agent. Additionally the inventive pharmaceutical composition may comprise small interfering RNA (siRNA) directed against genes of Rabies virus, e.g. siRNA directed against the gene encoding Glycoprotein G (RAV-G), nucleoprotein N (RAV-N), phosphoprotein P (RAV-P), matrix protein (RAV-M) or RNA polymerase L (RAV-L) of Rabies virus.

The inventive pharmaceutical composition typically comprises a "safe and effective amount" of the components of the inventive pharmaceutical composition, particularly of the inventive mRNA sequence(s) as defined herein. As used herein, a "safe and effective amount" means an amount of the inventive mRNA sequence(s) as defined herein as such that is sufficient to significantly induce a positive modification of a disease or disorder or to prevent a disease, preferably rabies as defined herein. At the same time, however, a "safe and effective amount" is small enough to avoid serious side-effects and to permit a sensible relationship between advantage and risk. The determination of these limits typically lies within the scope of sensible medical judgment.

The inventive pharmaceutical composition may be used for human and also for veterinary medical purposes, preferably for human medical purposes, as a pharmaceutical composition in general or as a vaccine.

According to another particularly preferred aspect, the inventive pharmaceutical composition (or the inventive mRNA sequence as defined herein or the inventive composition comprising a plurality of inventive mRNA sequences as defined herein) may be provided or used as a vaccine. Typically, such a vaccine is as defined above for pharmaceutical compositions. Additionally, such a vaccine typically contains the inventive mRNA sequence as defined herein or the inventive composition comprising a plurality of inventive mRNA sequences as defined herein.

The inventive vaccine may also comprise a pharmaceutically acceptable carrier, adjuvant, and/or vehicle as defined herein for the inventive pharmaceutical composition. In the specific context of the inventive vaccine, the choice of a pharmaceutically acceptable carrier is determined in principle by the manner in which the inventive vaccine is administered. The inventive vaccine can be administered, for example, systemically or locally. Routes for systemic administration in general include, for example, transdermal, oral, parenteral routes, including subcutaneous, intravenous, intramuscular, intraarterial, intradermal and intraperitoneal injections and/or intranasal administration routes. Routes for local administration in general include, for example, topical administration routes but also intradermal, transdermal, subcutaneous, or intramuscular injections or intralesional, intracranial, intrapulmonal, intracardial, and sublingual injections. More preferably, vaccines may be administered by an intradermal, subcutaneous, or intramuscular route. Inventive vaccines are therefore preferably formulated in liquid (or sometimes in solid) form.

Preferably, the inventive vaccine may be administered by conventional needle injection or needle-free jet injection. In a preferred embodiment the inventive vaccine may be administered by jet injection as defined herein, preferably intramuscularly or intradermally, more preferably intradermally.

The inventive vaccine can additionally contain one or more auxiliary substances in order to increase its immunogenicity or immunostimulatory capacity, if desired. Particularly preferred are adjuvants as auxiliary substances or additives as defined for the pharmaceutical composition.

In a further aspect, the invention is directed to a kit or kit of parts comprising the components of the inventive mRNA sequence, the inventive composition comprising a plurality of inventive mRNA sequences, the inventive pharmaceutical composition or vaccine and optionally technical instructions with information on the administration and dosage of the components.

Beside the components of the inventive mRNA sequence, the inventive composition comprising a plurality of inventive mRNA sequences, the inventive pharmaceutical composition or vaccine the kit may additionally contain a pharmaceutically acceptable vehicle, an adjuvant and at least one further component as defined herein, as well as means for administration and technical instructions. The components of the inventive mRNA sequence, the inventive composition comprising a plurality of inventive mRNA sequences, the inventive pharmaceutical composition or vaccine and e.g. the adjuvant may be provided in lyophilized form. In a preferred embodiment, prior to use of the kit for vaccination, the provided vehicle is than added to the lyophilized components in a predetermined amount as written e.g. in the provided technical instructions. By doing so the inventive mRNA sequence, the inventive composition comprising a plurality of inventive mRNA sequences, the inventive pharmaceutical composition or vaccine, according to the above described aspects of the invention is provided that can afterwards be used in a method as described above, also.

The present invention furthermore provides several applications and uses of the inventive mRNA sequence as defined herein, of the inventive composition comprising a plurality of inventive mRNA sequences as defined herein, of the inventive pharmaceutical composition, of the inventive vaccine, all comprising the inventive mRNA sequence as defined herein or of kits comprising same.

In a further aspect, the invention provides an mRNA sequence encoding at least one antigenic peptide or protein of Rabies virus, or a fragment, variant or derivative thereof, and a composition, a pharmaceutical composition, a vaccine and a kit, all comprising the mRNA sequence for use in a method of prophylactic (pre-exposure prophylaxis or post-exposure prophylaxis) and/or therapeutic treatment of Rabies virus infections (rabies). Consequently, in a further aspect, the present invention is directed to the first medical use of the inventive mRNA sequence, the inventive composition comprising a plurality of inventive mRNA sequences, the inventive pharmaceutical composition, the inventive vaccine, and the inventive kit as defined herein as a medicament. Particularly, the invention provides the use of an mRNA sequence encoding at least one antigenic peptide or protein of Rabies virus, or a fragment, variant or derivative thereof as defined above for the preparation of a medicament.

According to another aspect, the present invention is directed to the second medical use of the mRNA sequence encoding at least one antigenic peptide or protein of Rabies virus, or a fragment, variant or derivative thereof, as defined herein, optionally in form of a composition comprising a plurality of inventive mRNA sequences, a pharmaceutical composition or vaccine, kit or kit of parts, for the treatment of Rabies virus infections (rabies) as defined herein. Particularly, the mRNA sequence encoding at least one antigenic peptide or protein of Rabies virus, or a fragment, variant or derivative thereof to be used in a method as said above is a mRNA sequence formulated together with a pharmaceutically acceptable vehicle and an optionally additional adjuvant and an optionally additional further component as defined above e.g. a further antigen or a rabies immune globuline.

In this context the mRNA sequence used for post-exposure treatment of Rabies virus infection according to the invention can be combined with administration of rabies immune globuline.

The inventive mRNA sequence may alternatively be provided such that it is administered for preventing or treating rabies by several doses, each dose containing the inventive mRNA sequence encoding at least one antigenic peptide or protein of Rabies virus, or a fragment, variant or derivative thereof, e.g. the first dose containing at least one mRNA encoding at least one antigenic peptide or protein derived from the glycoprotein G (RAV-G) (or fragments, variants or derivatives thereof) and the second dose containing at least one mRNA sequence encoding at least one antigenic peptide or protein derived from a different antigen of Rabies virus, preferably from the nucleoprotein N (RAV-N) (or fragments, variants or derivatives thereof). By that embodiment, both doses are administered in a staggered way, i.e. subsequently, shortly one after the other, e.g. within less than 10 minutes, preferably less than 2 minutes, and at the same site of the body to achieve the same immunological effect as for administration of one single composition containing both, e.g. the mRNA encoding the glycoprotein G (RAV-G) and the mRNA encoding the nucleoprotein N (RAV-N).

According to a specific embodiment, the inventive mRNA sequence, or the inventive pharmaceutical composition or vaccine may be administered to the patient as a single dose or as at least one single dose, respectively. In certain embodiments, the inventive mRNA sequence or the inventive pharmaceutical composition or vaccine may be administered to a patient as a single dose followed by a second dose later and optionally even a third, fourth (or more) dose subsequent thereto etc. In accordance with this embodiment, booster inoculations with the inventive mRNA sequence or the inventive pharmaceutical composition or vaccine may be administered to a patient at specific time intervals, preferably as defined below, following the second (or third, fourth, etc.) inoculation. Preferably, at least one dose of the inventive mRNA sequence, pharmaceutical composition or vaccine is administered, preferably from 1 to 10 doses, more preferably from 2 to 7 doses, even more preferably from 2 to 5 doses and most preferably from 3 to 5 doses. In a particularly preferred embodiment, 3 doses are administered. In another embodiment 5 doses are administered. In this context, it is particularly preferred that several doses comprise the same mRNA sequence encoding the same antigenic peptide or protein of Rabies virus, e.g. glycoprotein G (RAV-G). In that embodiment, the doses are given in a specific time period, e.g. 20-30 or 20-60 days. The interval between the administration of two or more doses is preferably from 5 to 120 days, more preferably from 7 to 15 days or 15 to 30 days. In a preferred embodiment, the interval between the administration of two or more doses is at least 7 days, more preferably 28 days. For example, for post-exposure prophylaxis at least 5 doses of the inventive mRNA sequence or inventive pharmaceutical composition or vaccine can be administered within 20-30 days. As an example, for prophylactic treatment without exposure to the Rabies virus at least 3 doses of the inventive mRNA sequence or the inventive pharmaceutical composition or vaccine can be administered in 20-60 days.

In a preferred embodiment, a single dose of the inventive mRNA sequence, composition or vaccine comprises a specific amount of the mRNA according to the invention. Preferably, the inventive mRNA sequence is provided in an amount of at least 40 μg per dose, preferably in an amount of from 40 to 700 μg per dose, more preferably in an amount of from 80 to 400 μg per dose. More specifically, in the case of intradermal injection, which is preferably carried out by using a conventional needle, the amount of the inventive mRNA sequence comprised in a single dose is typically at least 200 μg, preferably from 200 μg to 1.000 μg, more preferably from 300 μg to 850 μg, even more preferably from 300 μg to 700 μg. In the case of intradermal injection, which is preferably carried out via jet injection (e.g. using a Tropis device), the amount of the inventive mRNA sequence comprised in a single dose is typically at least 80 μg, preferably from 80 μg to 700 μg, more preferably from 80 μg to 400 μg. Moreover, in the case of intramuscular injection, which is preferably carried out by using a conventional needle or via jet injection, the amount of the inventive mRNA sequence comprised in a single dose is typically at least 80 μg, preferably from 80 μg to 1.000 μg, more preferably from 80 μg to 850 μg, even more preferably from 80 μg to 700 μg.

More specifically, the following specific embodiments are particularly preferred:

the inventive mRNA sequence, or the inventive pharmaceutical composition or vaccine is administered to the patient, preferably intradermally, in three doses (40 μg/dose), preferably within 20-60 days, e.g. on day 0, 7 and 28 or on day 0, 28 and 56 of the treatment.

the inventive mRNA sequence, or the inventive pharmaceutical composition or vaccine is administered to the patient, preferably intradermally, in three doses (80 μg/dose), preferably within 20-60 days, e.g. on day 0, 7 and 28 or on day 0, 28 and 56 of the treatment.

the inventive mRNA sequence, or the inventive pharmaceutical composition or vaccine is administered to the patient, preferably intradermally, in three doses (160 μg/dose), preferably within 20-60 days, e.g. on day 0, 7 and 28 or on day 0, 28 and 56 of the treatment.

the inventive mRNA sequence, or the inventive pharmaceutical composition or vaccine is administered to the patient, preferably intradermally, in three doses (320 μg/dose), preferably within 20-60 days, e.g. on day 0, 7 and 28 or on day 0, 28 and 56 of the treatment.

the inventive mRNA sequence, or the inventive pharmaceutical composition or vaccine is administered to the patient, preferably intradermally by jet injection, in three doses (40 μg/dose), preferably within 20-60 days, e.g. on day 0, 7 and 28 or on day 0, 28 and 56 of the treatment.

the inventive mRNA sequence, or the inventive pharmaceutical composition or vaccine is administered to the patient, preferably intradermally by jet injection, in three doses (80 μg/dose), preferably within 20-60 days, e.g. on day 0, 7 and 28 or on day 0, 28 and 56 of the treatment.

the inventive mRNA sequence, or the inventive pharmaceutical composition or vaccine is administered to the patient, preferably intradermally by jet injection, in three doses (160 μg/dose), preferably within 20-60 days, e.g. on day 0, 7 and 28 or on day 0, 28 and 56 of the treatment.

the inventive mRNA sequence, or the inventive pharmaceutical composition or vaccine is administered to the patient, preferably intradermally by jet injection, in three doses (320 µg/dose), preferably within 20-60 days, e.g. on day 0, 7 and 28 or on day 0, 28 and 56 of the treatment.

the inventive mRNA sequence, or the inventive pharmaceutical composition or vaccine is administered to the patient, preferably intramuscularly, in three doses (40 µg/dose), preferably within 20-60 days, e.g. on day 0, 7 and 28 or on day 0, 28 and 56 of the treatment.

the inventive mRNA sequence, or the inventive pharmaceutical composition or vaccine is administered to the patient, preferably intramuscularly in three doses (80 µg/dose), preferably within 20-60 days, e.g. on day 0, 7 and 28 or on day 0, 28 and 56 of the treatment.

the inventive mRNA sequence, or the inventive pharmaceutical composition or vaccine is administered to the patient, preferably intramuscularly, in three doses (160 µg/dose), preferably within 20-60 days, e.g. on day 0, 7 and 28 or on day 0, 28 and 56 of the treatment.

the inventive mRNA sequence, or the inventive pharmaceutical composition or vaccine is administered to the patient, preferably intramuscularly, in three doses (320 µg/dose), preferably within 20-60 days, e.g. on day 0, 7 and 28 or on day 0, 28 and 56 of the treatment.

the inventive mRNA sequence, or the inventive pharmaceutical composition or vaccine is administered to the patient, preferably intramuscularly, in three doses (640 µg/dose), preferably within 20-60 days, e.g. on day 0, 7 and 28 or on day 0, 28 and 56 of the treatment.

the inventive mRNA sequence, or the inventive pharmaceutical composition or vaccine is administered to the patient, preferably intramuscularly by jet injection, in three doses (40 µg/dose), preferably within 20-60 days, e.g. on day 0, 7 and 28 or on day 0, 28 and 56 of the treatment.

the inventive mRNA sequence, or the inventive pharmaceutical composition or vaccine is administered to the patient, preferably intramuscularly by jet injection, in three doses (80 µg/dose), preferably within 20-60 days, e.g. on day 0, 7 and 28 or on day 0, 28 and 56 of the treatment.

the inventive mRNA sequence, or the inventive pharmaceutical composition or vaccine is administered to the patient, preferably intramuscularly by jet injection, in three doses (160 µg/dose), preferably within 20-60 days, e.g. on day 0, 7 and 28 or on day 0, 28 and 56 of the treatment.

the inventive mRNA sequence, or the inventive pharmaceutical composition or vaccine is administered to the patient, preferably intramuscularly by jet injection, in three doses (320 µg/dose), preferably within 20-60 days, e.g. on day 0, 7 and 28 or on day 0, 28 and 56 of the treatment.

the inventive mRNA sequence, or the inventive pharmaceutical composition or vaccine is administered to the patient, preferably intramuscularly by jet injection, in three doses (640 µg/dose), preferably within 20-60 days, e.g. on day 0, 7 and 28 or on day 0, 28 and 56 of the treatment.

In certain embodiments, such booster inoculations with the inventive mRNA sequence or inventive pharmaceutical composition or vaccine as disclosed above (second, third etc. vaccination) may utilize an additional compound or component as defined for the inventive mRNA sequence or inventive pharmaceutical composition or vaccine as defined herein.

According to a further aspect, the present invention also provides a method for expression of an encoded antigenic peptide or protein derived from glycoprotein G (RAV-G), nucleoprotein N (RAV-N), phosphoprotein P (RAV-P), matrix protein (RAV-M) or RNA polymerase L (RAV-L) of Rabies virus comprising the steps, e.g. a) providing the inventive mRNA sequence as defined herein or the inventive composition comprising a plurality of inventive mRNA sequences as defined herein, b) applying or administering the inventive mRNA sequence as defined herein or the inventive composition comprising a plurality of inventive mRNA sequences as defined herein to an expression system, e.g. to a cell-free expression system, a cell (e.g. an expression host cell or a somatic cell), a tissue or an organism. The method may be applied for laboratory, for research, for diagnostic, for commercial production of peptides or proteins and/or for therapeutic purposes. In this context, typically after preparing the inventive mRNA sequence as defined herein or of the inventive composition comprising a plurality of inventive mRNA sequences as defined herein, it is typically applied or administered to a cell-free expression system, a cell (e.g. an expression host cell or a somatic cell), a tissue or an organism, e.g. in naked or complexed form or as a pharmaceutical composition or vaccine as described herein, preferably via transfection or by using any of the administration modes as described herein. The method may be carried out in vitro, in vivo or ex vivo. The method may furthermore be carried out in the context of the treatment of a specific disease, particularly in the treatment of infectious diseases, preferably Rabies as defined herein.

In this context, in vitro is defined herein as transfection or transduction of the inventive mRNA as defined herein or of the inventive composition comprising a plurality of inventive mRNA sequences as defined herein into cells in culture outside of an organism; in vivo is defined herein as transfection or transduction of the inventive mRNA or of the inventive composition comprising a plurality of inventive mRNA sequences into cells by application of the inventive mRNA or of the inventive composition to the whole organism or individual and ex vivo is defined herein as transfection or transduction of the inventive mRNA or of the inventive composition comprising a plurality of inventive mRNA sequences into cells outside of an organism or individual and subsequent application of the transfected cells to the organism or individual.

Likewise, according to another aspect, the present invention also provides the use of the inventive mRNA sequence as defined herein or of the inventive composition comprising a plurality of inventive mRNA sequences as defined herein, preferably for diagnostic or therapeutic purposes, for expression of an encoded antigenic peptide or protein, e.g. by applying or administering the inventive mRNA sequence as defined herein or of the inventive composition comprising a plurality of inventive mRNA sequences as defined herein, e.g. to a cell-free expression system, a cell (e.g. an expression host cell or a somatic cell), a tissue or an organism. The use may be applied for laboratory, for research, for diagnostic for commercial production of peptides or proteins and/or for therapeutic purposes. In this context, typically after preparing the inventive mRNA sequence as defined herein or of the inventive composition comprising a plurality of inventive mRNA sequences as defined herein, it is typically applied or administered to a cell-free expression system, a cell (e.g. an expression host cell or a somatic cell), a tissue or an organism, preferably in naked form or complexed form, or as a pharmaceutical composition or vaccine as described herein, preferably via transfection or by using any of the administration modes as described herein. The use may be carried out in vitro, in vivo or ex vivo. The use may furthermore be carried out in the context of the treatment of a specific disease, particularly in the treatment of Rabies virus infections.

In a further aspect the invention provides a method of treatment or prophylaxis of rabies virus infections comprising the steps:
a) providing the inventive mRNA sequence, the composition comprising a plurality of inventive mRNA sequences, the pharmaceutical composition or the kit or kit of parts comprising the inventive mRNA sequence as defined above;
b) applying or administering the mRNA sequence, the composition, the pharmaceutical composition or the kit or kit of parts to a tissue or an organism;
c) optionally administering rabies immune globuline.

Taken together the invention provides in a certain aspect an mRNA sequence comprising a coding region encoding at least one antigenic peptide or protein of Rabies virus. The inventive mRNA sequence is for use in a method of prophylactic and/or therapeutic treatment of infections caused by Rabies viruses. Accordingly, the invention relates to an mRNA sequence as defined herein for use in a method of prophylactic and/or therapeutic treatment of rabies infections.

In the present invention, if not otherwise indicated, different features of alternatives and embodiments may be combined with each other, where suitable. Furthermore, the term "comprising" shall not be narrowly construed as being limited to "consisting of" only, if not specifically mentioned. Rather, in the context of the present invention, "consisting of" is an embodiment specifically contemplated by the inventors to fall under the scope of "comprising", wherever "comprising" is used herein.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

BRIEF DESCRIPTION OF THE DRAWINGS

The figures shown in the following are merely illustrative and shall describe the present invention in a further way. These figures shall not be construed to limit the present invention thereto.

FIG. 1: shows the mRNA sequence R2403 according to SEQ ID NO. 24, comprising a G/C optimized coding region coding for Rabies virus glycoprotein G (RAV-G), the 3'-UTR element muag according to SEQ ID No. 22, a poly (A) sequence consisting of 64 adenosines, a poly(C) sequence consisting of 30 cytosines and a histone stem-loop sequence according to SEQ ID No. 27, as comprised in the RAV-G mRNA vaccine.

FIG. 2: shows the mRNA sequence R2507 according to SEQ ID NO. 25, comprising a 5'-UTR element comprising the corresponding RNA sequence of the nucleic acid sequence according to SEQ ID NO. 16, a G/C optimized coding region coding for Rabies virus glycoprotein G (RAV-G), the 3'-UTR element albumin7 according to SEQ ID No. 18, a poly (A) sequence consisting of 64 adenosines, a poly(C) sequence consisting of 30 cytosines and a histone stem-loop sequence according to SEQ ID No. 27, as comprised in the RAV-G mRNA vaccine.

FIGS. 4A-B: show that RAV-G mRNA vaccine is immunogenic in mice and induces high titers of neutralizing antibodies comparable to licensed vaccines.
Female BALB/c mice were intradermally (i.d.) injected with the RAV-G mRNA vaccine (80 μg of R2403) or Ringer-Lactate (RiLa) as buffer control. Two groups were intramuscularly (i.m.) injected with ⅒ of the human dose of the licensed vaccines Rabipur® and HDC, respectively. All animals received boost injections on day 21 and blood samples were collected on day 35 for the determination of Rabies virus neutralization titers as described in Example 3.
(A) The RAV-G mRNA vaccine induced neutralizing antibody titers comparable to the HDC and Rabipur® vaccines, well above the WHO standard of 0.5 IU/ml. The line in the graph represents the median value (n=8 mice/group).
(B) The RAV-G mRNA vaccine induced long-lasting virus neutralization titers in mice well above the 0.5 IU/ml.

FIGS. 5A-C: show that RAV-G mRNA vaccine induces antigen-specific CD8$^+$ T cells.
The experiment was performed as describe in Example 4 and T cells were analysed by intracellular cytokine staining for the antigen-specific induction of cytokines. The line in the graph represents the median value (n=8 mice/group).

FIGS. 6A-C: show that RAV-G mRNA vaccine induces antigen-specific CD4$^+$ T cells at significantly higher frequencies than Rabipur®.
The experiment was performed as describe in Example 4 and T cells were analysed by intracellular cytokine staining. The line in the graph represents the median value (n=8 mice/group). Statistical differences between groups were assessed by the Mann Whitney test.

FIGS. 8A-B: show that the RAV-G mRNA vaccine protects mice against a lethal rabies virus challenge infection.
The experiment was performed as described in Example 6.
(A) Survival of rabies infected mice. All mice vaccinated with RAV-G mRNA or Rabipur® were protected against lethal challenge infection without weight loss.
(B) Weight kinetics of rabies infected mice. Several mice vaccinated with the HDC vaccine exhibited weight loss and one mouse reached defined endpoint criteria so that it was terminated before the end of the study.

FIGS. 9A-B: show that the RAV-G mRNA vaccine protects mice against a lethal virus challenge infection—Influence of immunization schedule The experiment was performed as described in Example 6.

(A) Survival of rabies infected mice, (B) Weight kinetics of rabies infected mice. Mice vaccinated three times using RAV-G mRNA in a one or three week intervals between vaccinations were protected against death and weight loss indicating that RAV-G mRNA vaccination is not limited to a fixed immunization schema. In addition, already two vaccinations using RAV-G mRNA were sufficient to protect mice against a lethal challenge infection in terms of protection against death or weight loss.

FIGS. 10A-B: show that the RAV-G mRNA vaccine is stable and immunogenic after storage for 6 months at 40° C. or 1 month at 60° C.

The experiment was performed as described in Example 7.

(A) Virus neutralization titer. The vaccine was still fully immunogenic after storage for 6 months at temperatures up to 40° C. or 1 month at 60° C.

(B) Survival of immunized mice. The vaccine was still fully protective after storage for 6 months up to 40° C. or 1 month at 60° C.

Figure 11:
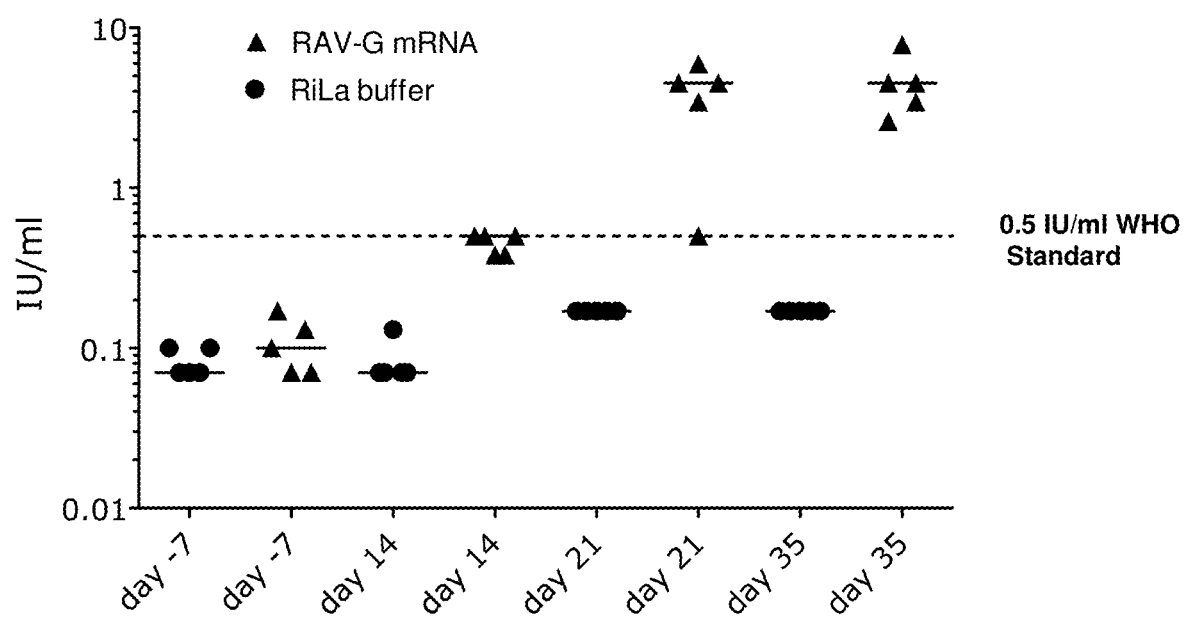

FIG. 11: shows that the RAV-G mRNA vaccine induces a protective immune response in adult pigs.

The experiment was performed as described in Example 8.

Pigs vaccinated with RAV-G mRNA showed a functional antibody response well above the 0.5 IU/ml WHO standard.

FIGS. 12A-B: show that the RAV-G mRNA vaccine induces significant virus neutralization titers in newborn pigs comparable to a benchmark vaccine (Rabipur®).

The experiment was performed as described in Example 9.

(A) Kinetics of virus neutralizing titers (mean and standard deviation, SD).

(B) Virus neutralization titers 2 weeks after boost vaccination.

Figure 13:
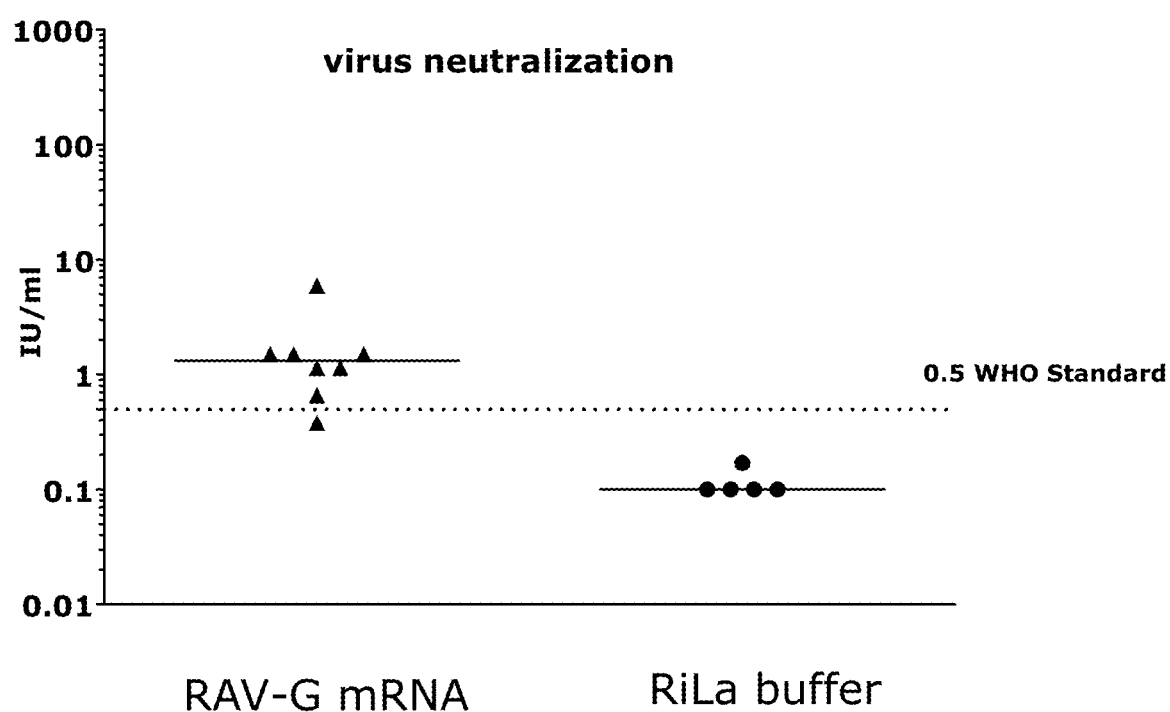

FIG. 13: shows that the RAV-G mRNA vaccine induces virus neutralization titers in mice after intramuscular injection. The experiment was performed as described in Example 10.

Figure 14:
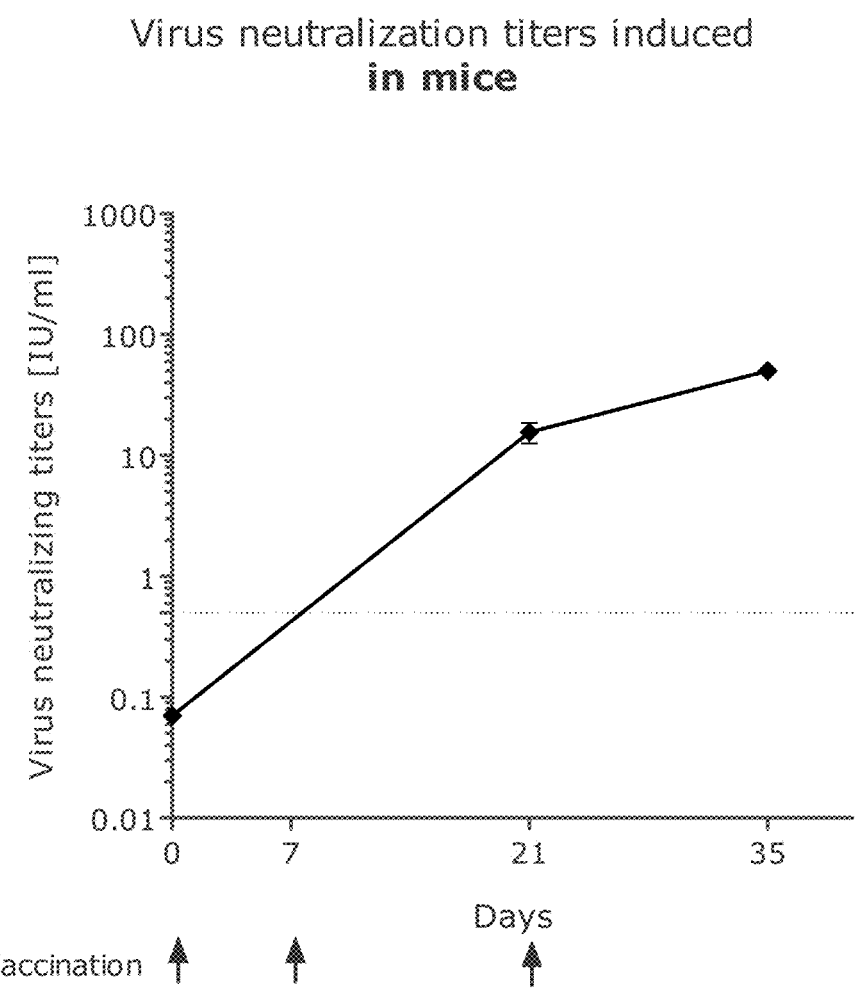

FIG. 14: shows the induction of virus neutralization titers in mice after intradermal vaccination with the RAV-G mRNA vaccine. The experiment was performed as described in Example 11.

Figure 15:
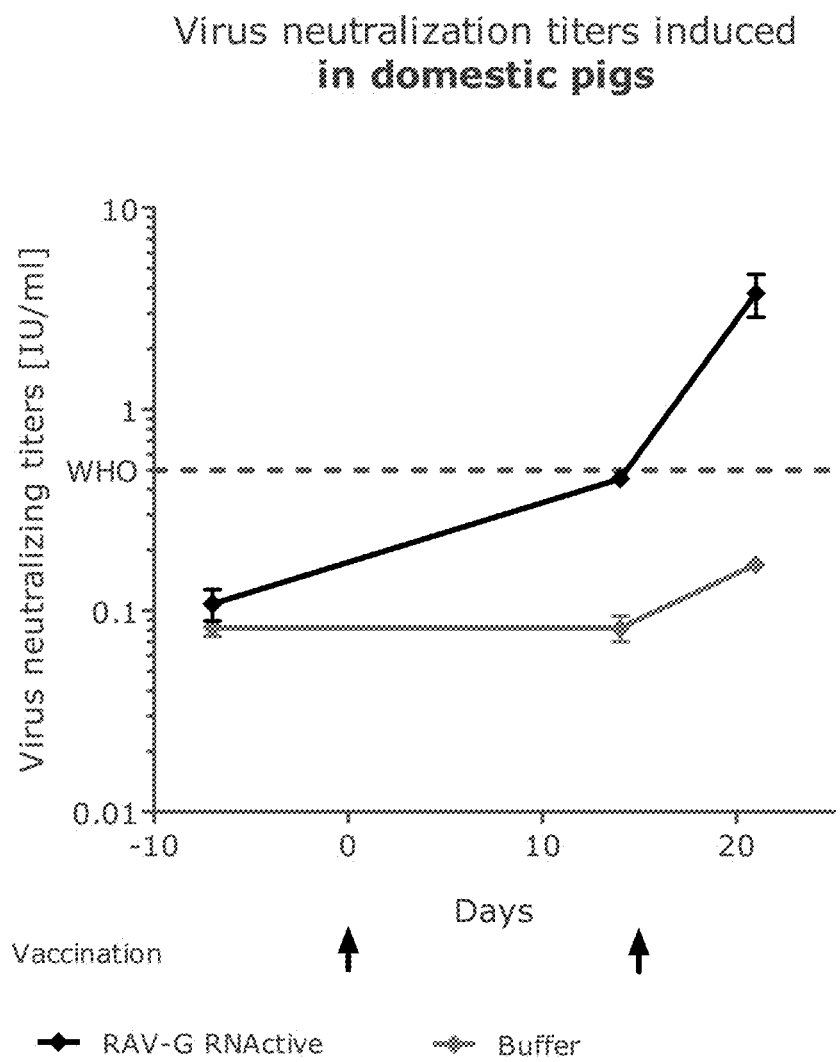

FIG. 15: shows the induction of virus neutralization titers in domestic pigs after intradermal vaccination with the RAV-G mRNA vaccine. The experiment was performed as described in Example 12.

Figure 16:
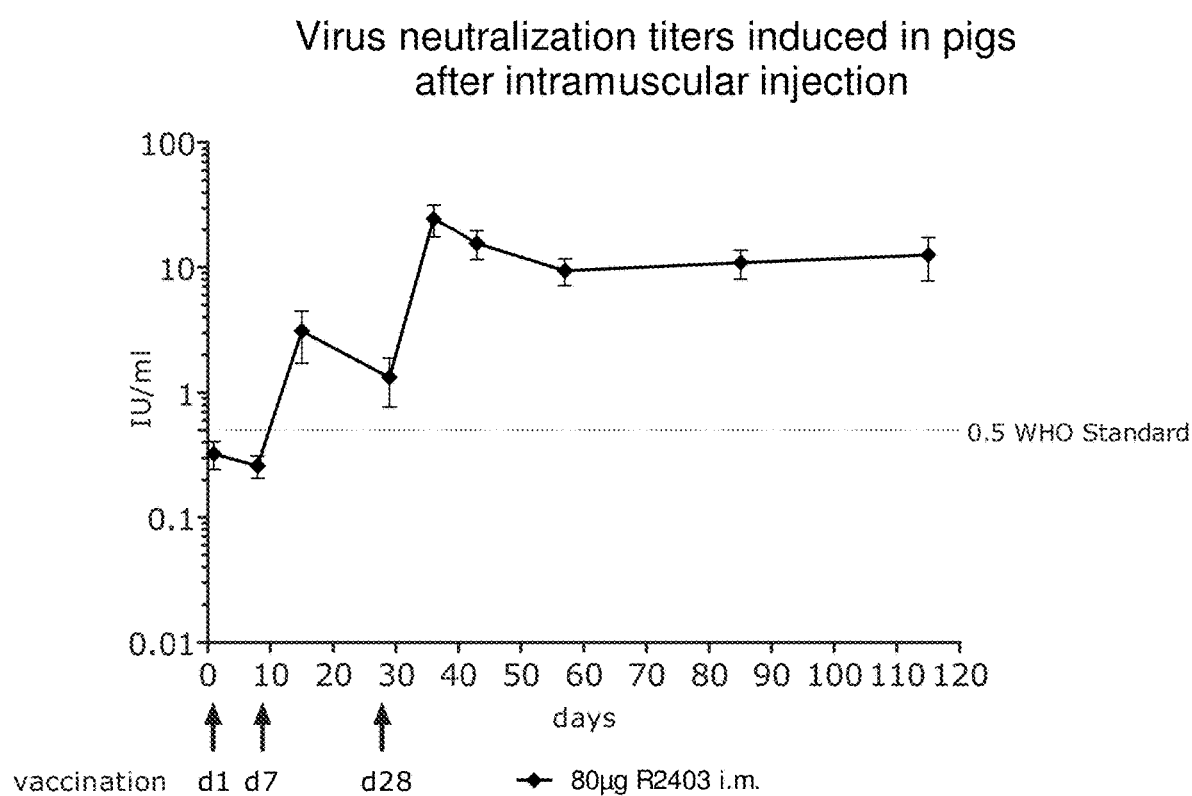

FIG. 16: shows the induction of virus neutralization titers in domestic pigs after intramuscular vaccination with the RAV-G mRNA vaccine. The experiment was performed as described in Example 13.

EXAMPLES

The examples shown in the following are merely illustrative and shall describe the present invention in a further way. These examples shall not be construed to limit the present invention thereto.

Example 1: Preparation of the Rabies mRNA Vaccine

1. Preparation of DNA and mRNA Constructs

For the present examples DNA sequences, encoding glycoprotein G (RAV-G) of the Pasteur vaccine strain were prepared and used for subsequent in vitro transcription. The corresponding mRNA sequences RAV-G(GC)-muag-A64-C30-histoneSL (R2403) and 32L-RAV-G (GC)-albumin7-A64-C30-histoneSL (R2507) are shown in FIGS. 1 and 2 according to SEQ. ID No. 24 and 25.

2. In Vitro Transcription

The respective DNA plasmids prepared according to paragraph 1 were transcribed in vitro using T7 polymerase in the presence of a CAP analogue (m$^7$GpppG). Subsequently the mRNA was purified using PureMessenger® (CureVac, Tubingen, Germany; WO 2008/077592A1).

The mRNA sequence RAV-G(GC)-muag-A64-C30-histoneSL (R2403; SEQ ID NO:24) comprises in 5'- to 3'-direction:

a.) a 5'-CAP structure consisting of m7GpppN;
b.) a G/C maximized coding region encoding the full-length protein of RAV-G of the Pasteur vaccine strain according to SEQ ID No. 1;
c.) a 3'-UTR element derived from a alpha globin gene, comprising the corresponding RNA sequence of the nucleic acid sequence according to SEQ ID NO. 22;
d.) a poly(A) sequence, comprising 64 adenosines;
e.) a poly(C) sequence, comprising 30 cytosines; and
f.) a histone-stem-loop structure, comprising the RNA sequence according to SEQ ID No 27.

The term "R2403", as used herein, refers to the mRNA sequence, which is defined by the sequence according to SEQ ID NO:24. The "R2403" mRNA may be provided in lyophilised form, which is preferably used for storage and/or transport of the inventive mRNA sequence or may be provided in the solved form in the appropriate liquid. Before administration to a subject, the mRNA according to SEQ ID NO:24, if provided in lyophilised form, is typically reconstituted in an appropriate liquid as defined herein, preferably in Ringer-Lactate, in order to obtain a liquid formulation.

The mRNA sequence 32L-RAV-G(GC)-albumin7-A64-C30-histoneSL (R2507) comprises in 5'- to 3'-direction:

a.) a 5'-CAP structure, consisting of m7GpppN;
b.) a 5'-UTR element comprising the corresponding RNA sequence of the nucleic acid sequence according to SEQ ID NO. 16;
c.) a G/C-maximized coding region encoding the full-length protein of RAV-G of the Pasteur vaccine strain according to SEQ ID No. 1;
d.) a 3'UTR element comprising the corresponding RNA sequence of a nucleic acid sequence according to SEQ ID NO. 18;
e.) a poly(A) sequence, comprising 64 adenosines;
f.) a poly(C) sequence, comprising 30 cytosines; and
g.) a histone-stem-loop structure, comprising the RNA sequence according to SEQ ID No 27.

3. Reagents

Complexation Reagent: protamine

4. Preparation of the Vaccine

The mRNA R2403 or R2507 were complexed with protamine by addition of protamine to the mRNA in the ratio (1:2) (w/w) (adjuvant component). After incubation for 10 min, the same amount of free mRNA R2403 or R2507 used as antigen-providing mRNA was added.

Example 2: In Vitro Characterization of mRNA Encoding Rabies Virus G Protein (RAV-G)

HeLa cells were seeded in a 6-well plate at a density of 300 000 cells/well in cell culture medium (RPMI, 10% FCS, 1% L-Glutamine, 1% Pen/Strep) 24 h prior to transfection. HeLa cells were transfected with 5 µg of RAV-G encoding mRNA (R2403) or influenza HA protein of A/Netherlands/602/2009 encoding mRNA (R2429) as negative control using Lipofectamine 2000 (Invitrogen) and stained 24 hours post transfection with a rabies virus specific antibody (HyTest Ltd; #11/06-R7-C5) and FITC labelled goat anti-mouse IgG antibody (Invitrogen, #871942A) and analysed by flow cytometry (FACS). The flow cytometry data are evaluated quantitatively by FlowJo software.

Figure 3:
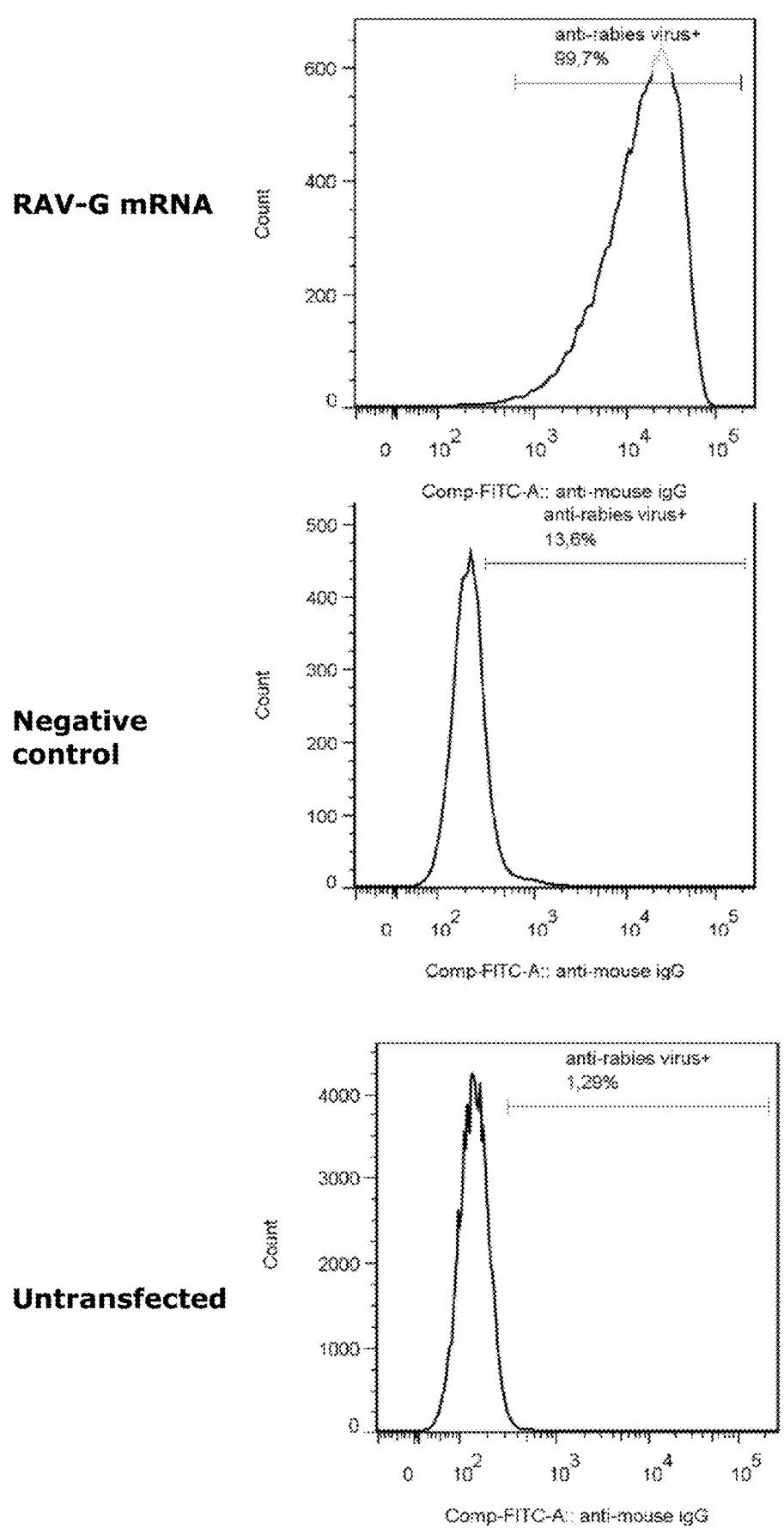
FIG. 3: shows that transfection of HeLa cells with mRNA R2403 coding for the RAV-G protein leads to the expression of the encoded RAV-G protein on the cell surface and that the protein is recognized by an anti-RAV-G antibody. Construct R2429 encoding the influenza HA protein of A/Netherlands/602/2009 served as a negative control, as well as untransfected cells. 24 hours post transfection the RAV-G proteins was stained with a rabies specific antibody and FITC-labelled secondary antibody and analysed by FACS as shown in Example 2.

FIG. 3 demonstrates that the RAV-G protein is, as expected for the Rabies G protein, expressed on the surface of transfected cells and can be recognized by an anti-rabies antibody.

Example 3: Induction of a Humoral Immune Response by the RAV-G mRNA Vaccine

Immunization

On day zero, BALB/c mice were intradermally (i.d.) injected with the mRNA vaccine comprising mRNA coding for Rabies virus glycoprotein G (RAV-G) (R2403 according to Example 1; 80 µg/mouse/vaccination day) or Ringer-lactate (RiLa) as buffer control. Two control groups were intramuscularly (i.m.) injected with 1/10 of the human dose of the licensed vaccines Rabipur® (Novartis) and HDC (human diploid cell vaccine, Sanofi Pasteur MSD GmbH), respectively. All animals received boost injections on day 21 and blood samples were collected on day 35 for the determination of virus neutralization titers.

To establish a long term kinetic of the anti-RAV-G immune response, blood samples were taken from group 1 after 15, 29, 38 and 48 weeks and virus neutralization titers were determined.

TABLE 1

Animal groups

| Group | Strain sex | Number of mice | Route volume | Vaccine dose | Vaccination schedule |
|---|---|---|---|---|---|
| 1 | BALB/c Female | 8 | i.d. 100 µl | R2403 80 µg | d0: prime, d21: boost d35: blood collection |
| 2 | BALB/c Female | 8 | i.m. 50 µl | HDC inactivated (1/10 of human dose) | d0: prime, d21: boost d35: blood collection |
| 3 | BALB/c Female | 8 | i.m. 50 µl | Rabipur ® (1/10 of human dose) | d0: prime, d21: boost d35: blood collection |
| 4 | BALB/c Female | 8 | i.d. 100 µl | 100% Ringer Lactate (RiLa) buffer | d0: prime, d21: boost d35: blood collection |

The licensed rabies vaccines Rabipur® (Novartis) and HDC (Human diploid cells, Sanofi Pasteur MSD GmbH) comprise inactivated Rabies virus.

Virus Neutralization Test

Detection of the virus neutralizing antibody response (specific B-cell immune response) was carried out by a virus neutralisation assay. The result of that assay is referred to as virus neutralization titer (VNT). According to WHO standards, an antibody titer is considered protective if the respective VNT is at least 0.5 IU/ml. Therefore, blood samples were taken from vaccinated mice on day 35 and from vaccinated humans on day 42 or as indicated after vaccination and sera were prepared. These sera were used in fluorescent antibody virus neutralisation (FAVN) test using the cell culture adapted challenge virus strain (CVS) of rabies virus as recommended by the OIE (World Organisation for Animal Health) and first described in Cliquet F., Aubert M. & Sagne L. (1998); J. Immunol. Methods, 212, 79-87. Shortly, heat inactivated sera will be tested as quadruplicates in serial two-fold dilutions as quadruplicates for their potential to neutralise 100 $TCID_{50}$ (tissue culture infectious doses 50%) of CVS in 50 µl of volume. Therefore sera dilutions are incubated with virus for 1 hour at 37° C. (in humid incubator with 5% $CO_2$) and subsequently trypsinized BHK-21 cells are added ($4 \times 10^5$ cells/ml; 50 µl per well). Infected cell cultures are incubated for 48 hours in humid incubator at 37° C. and 5% $CO_2$. Infection of cells is analysed after fixation of cells using 80% acetone at room temperature using FITC anti-rabies conjugate. Plates were washed twice using PBS and excess of PBS was removed. Cell cultures are scored positive or negative for the presence of rabies virus. Negative scored cells in sera treated wells represent neutralization of rabies virus. Each FAVN tests includes WHO or OIE standard serum (positive reference serum) that serves as reference for standardisation of the assay. Neutralization activity of test sera is calculated with reference to the standard serum provided by the WHO and displayed as International Units/ml (IU/ml).

Results

As can be seen in FIG. 4A, the RAV-G mRNA vaccine (R2403) induces neutralizing antibody titers comparable to the HDC and Rabipur® vaccines, well above the WHO standard of 0.5 IU/ml.

As can be seen from FIG. 4B, the RAV-G mRNA vaccine induces long-lasting rabies virus neutralization titers in mice.

Example 4: Induction of a Cellular Immune Response by the RAV-G mRNA Vaccine

Immunization

On day zero, BALB/c mice were intradermally (i.d.) injected with the RAV-G mRNA vaccine R2403 (80 µg/mouse/vaccination/day) or Ringer-lactate (RiLa) as buffer control. A control group was intramuscularly (i.m.) injected with 1/10 of the human dose of the licensed vaccine Rabipur®. All animals received boost injections on day 21. Serum and spleens were collected (n=8 on day 28, n=8 on day 35) for the analysis of antigen-specific T cells.

TABLE 2

Animal groups

| Group | Strain sex | Number of mice | Route volume | Vaccine dose | Vaccination schedule |
|---|---|---|---|---|---|
| 1 | BALB/c Female | 16 | i.d. 2 × 50 µl | R2403 80 µg | d0: prime, d21: boost; d28, d35: sample collection |

TABLE 2-continued

| Group | Strain sex | Number of mice | Route volume | Vaccine dose | Vaccination schedule |
|---|---|---|---|---|---|
| 2 | BALB/c Female | 16 | i.m. 4 × 25 µl | Rabipur ® (1/10 of human dose) | d0: prime, d21: boost; d28, d35: sample collection |
| 3 | BALB/c Female | 16 | i.d. 2 × 50 µl | 100% Ringer Lactate (RiLa) buffer | d0: prime, d21: boost; d28, d35: sample collection |

Intracellular Cytokine Staining

Splenocytes from vaccinated and control mice were isolated according to a standard protocol. Briefly, isolated spleens were grinded through a cell strainer and washed in PBS/1% FBS followed by red blood cell lysis. After an extensive washing step with PBS/1% FBS splenocytes were seeded into 96-well plates ($2 \times 10^6$ cells/well) and kept overnight at 4° C. The next day cells were stimulated with the RAV-G peptide library (JPT) that comprised the amino acid sequence of the Rabies G protein from Pasteur vaccine strain of Rabies virus according to SEQ ID No. 1 displayed as 15 amino acid peptides with an overlap of 11 amino acids between adjacent peptides and 2.5 µg/ml of an anti-CD28 antibody (BD Biosciences) for 6 hours at 37° C. in the presence of the mixture of GolgiPlug™/GolgiStop™ (Protein transport inhibitors containing Brefeldin A and Monensin, respectively; BD Biosciences). After stimulation cells were washed and stained for intracellular cytokines using the Cytofix/Cytoperm reagent (BD Biosciences) according to the manufacturer's instructions. The following antibodies were used for staining: CD8-PECy7 (1:200), CD3-FITC (1:200), IL2-PerCP-Cy5.5 (1:100), TNFα-PE (1:100), IFNγ-APC (1:100) (eBioscience), CD4-BD Horizon V450 (1:200) (BD Biosciences) and incubated with FcγR-block diluted 1:100. Aqua Dye was used to distinguish live/dead cells (Invitrogen). Cells were collected using a Canto II flow cytometer (Beckton Dickinson). Flow cytometry data were analysed using FlowJo software (Tree Star, Inc.). Statistical analysis was performed using GraphPad Prism software, Version 5.01. Statistical differences between groups were assessed by the Mann Whitney test.

Results

Figure 5C:
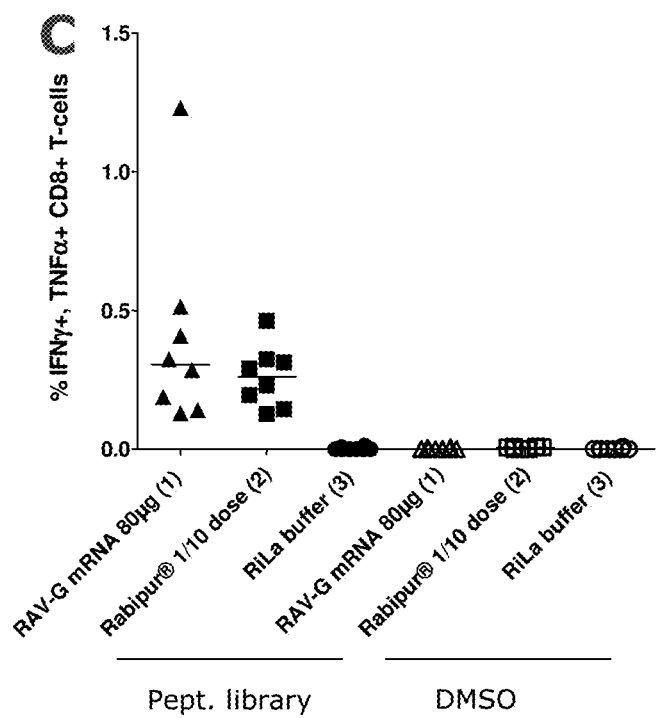

As can be seen from FIG. 5, the RAV-G mRNA vaccine (R2403) induced IFNγ positive, TNFα positive and IFNγ/TNFα double-positive multifunctional CD8+ T cells at comparable frequencies as the Rabipur® vaccine.

Figure 6C:
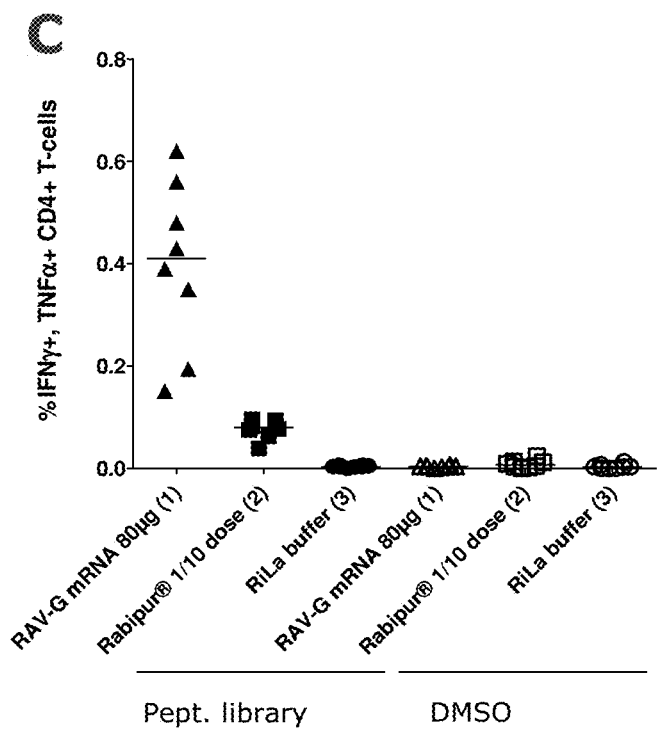
Figure 7:
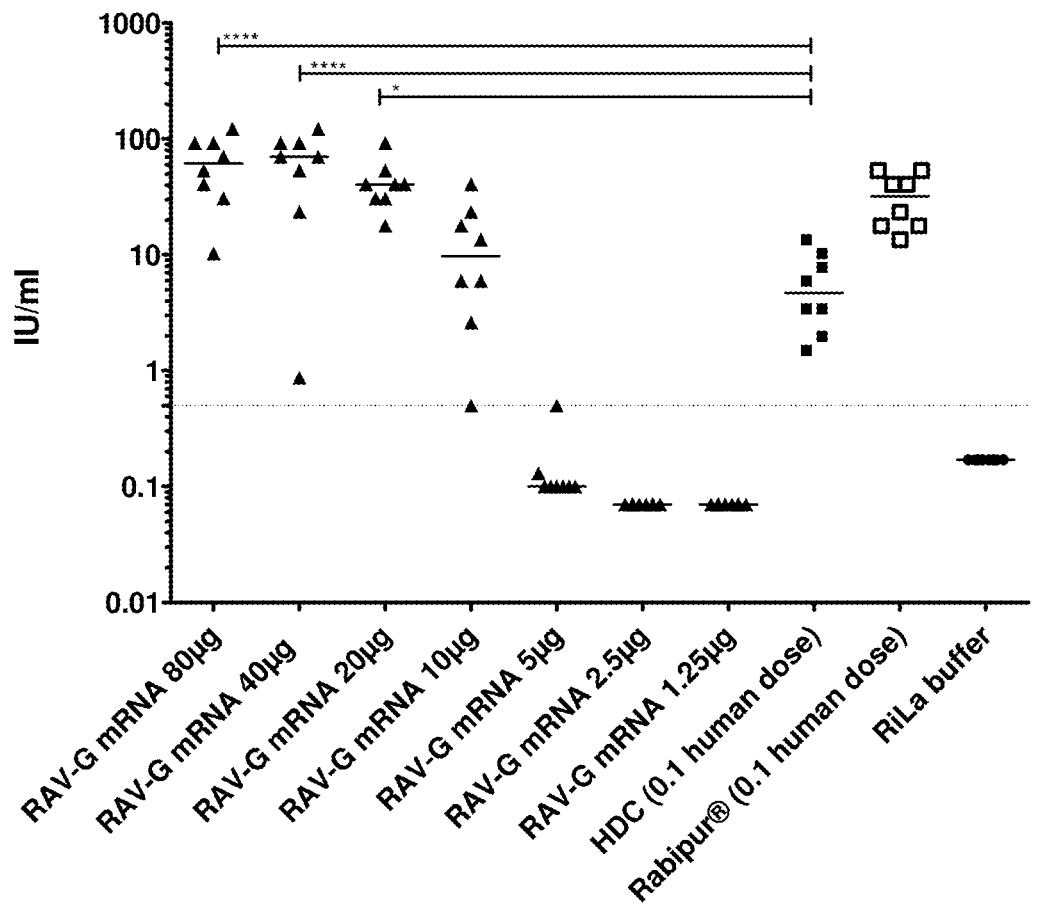
FIG. 7: shows that RAV-G mRNA vaccine induces a dose-dependent functional antibody (virus neutralisation antibody) response in C57BL/6 mice, demonstrating dose-response relationship between RAV-G mRNA and the induction of functional antibodies.
The experiment was performed as described in Example 5 and virus neutralization titers (IU/ml) were determined. The line in the graph represents the median value (n=8 mice/group). Statistical analysis: ANOVA (Kruskal-Wallis), **: p≤0.01; *: p≤0.05.

As can be seen from FIG. 6, the RAV-G mRNA vaccine (R2403) induced IFNγ positive, TNFα positive and IFNγ/TNFα double-positive multifunctional CD4+ T cells at significantly higher frequencies than the Rabipur® vaccine which comprises the whole inactivated Rabies virus.

Example 5: Induction of a Dose-Dependent Humoral Immune Response by the RAV-G mRNA Vaccine in C57BL/6 Mice Immunization On day zero, C57BL/6 mice were intradermally (i.d.) injected with different doses of the RAV-G mRNA vaccine R2403 or Ringer-lactate (RiLa) as buffer control as shown in Table 3. Two groups were intramuscularly (i.m.) injected with 1/10 of the human dose of the licensed vaccines Rabipur® and HDC, respectively. All animals received boost injections on day 21. Blood samples were taken on day 35 and sera were analysed in the fluorescent antibody virus neutralisation (FAVN) test as described in Example 3.

TABLE 3

| Group | Strain sex | Number of mice | Route volume | Vaccine dose | Vaccination schedule |
|---|---|---|---|---|---|
| 1 | C57BL/6 Female | 8 | i.d. 2 × 50 µl | R2403 80 µg | d0: prime, d21: boost d35: blood collection |
| 2 | C57BL/6 Female | 8 | i.d. 2 × 50 µl | R2403 40 µg | d0: prime, d21: boost d35: blood collection |
| 3 | C57BL/6 Female | 8 | i.d. 2 × 50 µl | R2403 20 µg | d0: prime, d21: boost d35: blood collection |
| 4 | C57BL/6 Female | 8 | i.d. 2 × 50 µl | R2403 10 µg | d0: prime, d21: boost d35: blood collection |
| 5 | C57BL/6 Female | 8 | i.d. 2 × 50 µl | R2403 5 ug | d0: prime, d21: boost d35: blood collection |
| 6 | C57BL/6 Female | 8 | i.m. 4 × 25 µl | HDC inactivated (0.1 of human dose) | d0: prime, d21: boost d35: blood collection |
| 7 | C57BL/6 Female | 8 | i.m. 4 × 25 µl | Rabipur ® (0.1 of human dose) | d0: prime, d21: boost d35: blood collection |
| 8 | C57BL/6 Female | 8 | i.d. 2 × 50 µl | 100% Ringer Lactate (RiLa) buffer | d0: prime, d21: boost d35: blood collection |

Results

As can be seen from FIG. 6, the RAV-G mRNA vaccine induces a dose-dependent antibody response. Doses of 20 µg, 40 µg and 80 µg induced significantly higher virus neutralizing antibody titers compared to 0.1 human dose of the HDC vaccine.

Example 6: Rabies Virus Challenge Infection of Mice

Immunization

Female BALB/c mice were intradermally (i.d.) injected with the RAV-G mRNA vaccine R2403 according to the schedule shown in Table 3 or Ringer-lactate (RiLa) as buffer control. Two control groups were intramuscularly (i.m.) injected with 1/10 of the human dose of the licensed vaccines Rabipur® and HDC, respectively. Sixteen days after the last immunization the animals were infected using a 40-fold LD50 dose of the CVS strain of Rabies virus intracranially (i.c.). Mice were monitored for specific symptoms of Rabies disease and body weight development.

TABLE 4

Animal groups

| Group | Strain sex | Number of mice | Route volume | Vaccine dose | Vaccination schedule |
|---|---|---|---|---|---|
| 1 | BALB/c Female | 8 | i.d. 1 × 100 μl | R2403 80 μg | d0: prime, d21: boost, d42: boost, d58: challenge (P/B/B 3 week interval) |
| 2 | BALB/c Female | 8 | i.m. 2 × 50 μl | HDC 0.1 human dose | d0: prime, d21: boost, d42: boost, d58: challenge (P/B/B 3 week interval) |
| 3 | BALB/c Female | 8 | i.m. 2 × 50 μl | Rabipur® 0.1 human dose | d0: prime, d21: boost, d42: boost, d58: challenge (P/B/B 3 week interval) |
| 4 | BALB/c Female | 8 | i.d. 1 × 100 μl | 100% RiLa buffer | d0: prime, d21: boost, d42: boost, d58: challenge (P/B/B 3 week interval) |
| 5 | BALB/c Female | 8 | i.d. 1 × 100 μl | R2403 80 μg | d28: prime, d35: boost, d42: boost, d58: challenge (P/B/B 1 week interval) |
| 6 | BALB/c Female | 8 | i.d. 1 × 100 μl | R2403 80 μg | d21: boost, d42: boost, d58: challenge (P/B 3 week interval) |

Results

As can be seen from FIG. 8A, the RAV-G mRNA vaccine protected all mice against a lethal rabies virus challenge infection. All mice vaccinated with RAV-G mRNA or Rabipur® were protected against a lethal challenge infection without weight loss.

As can be seen from FIG. 8B, several mice vaccinated with the HDC vaccine exhibited weight loss and one diseased mouse in the HDC group reached defined endpoint criteria and was therefore terminated before the end of the study.

As can be seen from FIG. 9A, two vaccinations with the RAV-G mRNA vaccine (Prime/Boost in three week interval) were sufficient to fully protect mice against a lethal challenge infection with rabies virus.

Example 7: Induction of a Humoral Immune Response by the RAV-G mRNA Vaccine after Storage To test the stability of the RAV-G mRNA vaccine, samples were stored at 5° C., 250 and 40° C. for 6 months and at 60° C. for one month. Subsequently, mice were vaccinated with these samples and their immunogenic and protective potential was evaluated.

Immunization

Female BALB/c mice were intradermally (i.d.) injected with the RAV-G mRNA vaccine R2403 according to the schedule shown in Table 5 or Ringer-lactate (RiLa) as buffer control. A control group was intramuscularly (i.m.) injected with ⅒ of the human dose of the licensed vaccine HDC (stored as recommended by the manufacture at 2-8° C.). Two weeks after the last vaccination blood samples were collected and sera were analysed in the fluorescent antibody virus neutralisation (FAVN) test as described in Example 3. Sechs weeks after the last immunization the animals were infected using 25-fold LD50 of CVS strain of Rabies virus intracranially (i.c.). Mice were monitored for specific symptoms of Rabies disease and body weight development.

TABLE 5

Animal groups

| Group | Strain sex | Number of mice | Route volume | Vaccine, dose Storage | Vaccination schedule |
|---|---|---|---|---|---|
| 1 | BALB/c Female | 5 | i.d. 2 × 50 μl | R2403, 80 μg 6 months, +5° C. | d0: prime, d21: boost; d35: blood collection |
| 2 | BALB/c Female | 5 | i.d. 2 × 50 μl | R2403, 80 μg 6 months, +25° C. | d0: prime, d21: boost; d35: blood collection |
| 3 | BALB/c Female | 5 | i.d. 2 × 50 μl | R2403, 80 μg 6 months, +40° C. | d0: prime, d21: boost; d35: blood collection |
| 4 | BALB/c Female | 5 | i.d. 2 × 50 μl | R2403, 80 μg 1 month, +60° C. | d0: prime, d21: boost; d35: blood collection |
| 5 | BALB/c Female | 5 | i.d. 2 × 50 μl | 100% Ringer Lactate (RiLa) buffer | d0: prime, d21: boost; d35: blood collection |
| 6 | BALB/c Female | 5 | i.m. 4 × 25 μl | HDC (0.1 of human dose) | d0: prime, d21: boost; d35: blood collection |

Results

As can be seen from FIG. 10A, the RAV-G mRNA vaccine is stable and immunogenic after storage for 6 months up to 40° C. or 1 month at 60° C. In addition, the vaccine is still fully protective as demonstrated in a lethal challenge infection (10B)

Example 8: Induction of a Humoral Immune Response by the RAV-G mRNA Vaccine in Pigs Immunization Two groups of pigs (Hungarian large white pig, 6 to 8 weeks old, female; n=5) were intradermally (i.d.) injected with the RAV-G mRNA vaccine R2507 or Ringer-lactate (RiLa) as buffer control according to the schedule shown in Table 6. One week before (preimmune serum) and 2, 3 and 5 weeks after the first vaccination blood samples were collected and sera were analysed in the fluorescent antibody virus neutralisation (FAVN) test as described in Example 3.

TABLE 6

Animal groups

| Group | Strain sex | Number of mice | Route volume | Vaccine dose | Vaccination schedule |
|---|---|---|---|---|---|
| 1 | Pigs | 8 | i.d. 100 μl | R2507 80 μg | d0: prime, d14: boost; blood collection: day −7, 14, 21, 35 |

TABLE 6-continued

| Group | Strain sex | Number of mice | Route volume | Vaccine dose | Vaccination schedule |
|---|---|---|---|---|---|
| 2 | Pigs | 8 | i.d. 4 × 80 μl | 100% RiLa buffer | d0: prime, d14: boost; blood collection: day −7, 14, 21, 35 |

Results

As can be seen from FIG. 11, the RAV-G mRNA vaccine induces an immune response after prime/boost vaccination well above the 0.5 IU/ml WHO standard.

Example 9: Induction of Virus Neutralization Titers by the RAV-G mRNA Vaccine in Newborn Pigs is Comparable to a Benchmark Vaccine (Rabipur®)

Immunization

On day zero, 3 to 4 day old piglets (German domestic pig, of both genders) from two litters were intradermally (i.d.) injected with the RAV-G mRNA vaccine R2403 and an unrelated control mRNA vaccine (R2402 encoding the HA protein of influenza H5N1) as shown in Table 7. A third group was intramuscularly (i.m.) injected with one human dose of the licensed vaccine Rabipur®. All animals received boost injections on day 21. Blood samples were taken on day 0 (preimmune serum) and days 21, 28, 35, 49 and 70. Sera were prepared and analysed in the fluorescent antibody virus neutralisation (FAVN) test as described in Example 3.

TABLE 7

| Group | Strain sex | Number of mice | Route volume | Vaccine dose | Vaccination schedule |
|---|---|---|---|---|---|
| 1 | Pigs | 6 | i.d. 2 × 150 μl | R2403 240 μg | d0: prime, d21: boost |
| 2 | Pigs | 5 | i.d. 2 × 150 μl | R2402 240 μg | d0: prime, d21: boost |
| 3 | Pigs | 5 | i.m. 1 × 1 ml | Rabipur ® human dose | d0: prime, d21: boost |

Results

As can be seen from FIG. 12, the RAV-G mRNA vaccine induces virus neutralizing antibodies after prime-boost vaccination of new born pigs, well above the 0.5 IU/ml WHO standard.

Example 10: Induction of Virus Neutralization Titers by the RAV-G mRNA Vaccine after Intramuscular Immunization in Mice Immunization Female BALB/c mice were intramuscularly (i.m.; *M. tibialis*) injected with the RAV-G mRNA vaccine R2507 or Ringer-lactate (RiLa) as buffer control according to the schedule shown in Table 8. One week after the last vaccination blood samples were collected and sera were analysed in the fluorescent antibody virus neutralisation (FAVN) test as described in Example 3.

TABLE 8

| Group | Strain sex | Number of mice | Route volume | Vaccine dose | Vaccination schedule |
|---|---|---|---|---|---|
| 1 | BALB/c Female | 8 | i.m. 2 × 25 μl | R2507, 20 μg | d0: prime, d7: boost, d14: blood collection |
| 5 | BALB/c Female | 8 | i.m. 2 × 25 μl | 100% Ringer Lactate (RiLa) buffer | d0: prime, d7: boost, d14: blood collection |

Results

As can be seen from FIG. 13, the RAV-G mRNA vaccine induces virus neutralization titers in mice after intramuscular injection well above the 0.5 IU/ml WHO standard.

Example 11: Induction of a Humoral Immune Response by the RAV-G mRNA Vaccine in Mice Immunization On day zero, BALB/c mice were intradermally (i.d.) injected with the mRNA vaccine comprising mRNA coding for Rabies virus glycoprotein G (RAV-G) (according to Example 1; 80 μg/mouse/vaccination day). All animals received boost injections on day 7 and 21. To establish a long term kinetic of the anti-RAV-G immune response blood samples were collected on day 0, 21 and 35 for the determination of virus neutralization titers.

Virus Neutralization Test

The virus neutralization test was performed as described in Example 3.

Results

As can be seen in FIG. 14, the RAV-G mRNA vaccine (R2403) induces already after two vaccinations neutralizing antibody titers, well above the WHO standard of 0.5 IU/ml.

Example 12: Induction of a Humoral Immune Response by the RAV-G mRNA Vaccine in Domestic Pigs Immunization Two groups of pigs (Hungarian large white pig, 6 to 8 weeks old, female; n=5) were intradermally (i.d.) injected on day 0 and 14 with the RAV-G mRNA vaccine R2507 or Ringer-lactate (RiLa) as buffer control. One week before (preimmune serum) the first vaccination (day 0) and on day 14 and 21 after the first vaccination blood samples were collected and sera were analysed in the fluorescent antibody virus neutralisation (FAVN) test as described in Example 3.

Results

As can be seen from FIG. 15, only one vaccination with the RAV-G mRNA vaccine is sufficient to reach the WHO standard of 0.5 IU/ml neutralizing antibody titers in domestic pigs.

Example 13: Induction of a Humoral Immune Response by the RAV-G mRNA Vaccine in Domestic Pigs Immunization Domestic pigs (Hungarian large white pig, 6 to 8 weeks old, female; n=5) were intramuscularly (i.m.) injected on day 1, 8 and 29 with the RAV-G mRNA vaccine R2403. Blood samples were collected on day 1, 8, 15, 29, 36, 43, 57 and 115 and sera were analysed in the fluorescent antibody virus neutralisation (FAVN) test as described in Example 3.

Results

As can be seen from FIG. 16, intramuscular vaccination with the RAV-G mRNA vaccine is able to induce neutralizing antibody titers above the WHO standard of 0.5 IU/ml in domestic pigs. The long-term kinetic shows that even 115 days after the last vaccination the neutralizing antibody titers are above the WHO standard of 0.5 IU/ml.

Example 14: Induction of a Humoral Immune Response by the RAV-G mRNA Vaccine in Humans Immunization Preliminary results obtained in an ongoing clinical trial (phase I) demonstrate safety as well as efficacy of the vaccine according to the invention. In the clinical study, human volunteers were intradermally injected via jet injection using a Tropis device on day 0, 7 and 28 with the RAV-G mRNA vaccine R2403. The mRNA was prepared as described in Example 1 herein, i.e. mRNA complexed with protamine in a ratio of 2:1 (w/w) was mixed with an equal amount of free mRNA. On each of the three vaccination days, 80 µg of mRNA were administered.

In order to assess the safety profile of the vaccine according to the invention, subjects were monitored after administration (vital signs, vaccination site tolerability assessments, hematologic analysis after the second and third injection). The preliminary results obtained in the ongoing clinical study suggest that immunization with the mRNA according to the invention is well-tolerated in humans.

The efficacy of the immunization was analysed by determination of virus neutralizing titers (VNT) in sera from six subjects. To this end, blood samples were collected on day 0 as baseline and on day 42. Sera were analysed for virus neutralizing antibodies in the fluorescent antibody virus neutralisation (FAVN) test as described in Example 3. The results are summarized in Table 9.

TABLE 9

Virus neutralizing titers after immunization of human subjects

| Subject no. | Virus neutralizing titer (VNT; IU/ml) |
| --- | --- |
| 1 | 4.0 |
| 2 | 0.7 |
| 3 | 0.2 |
| 4 | 0.7 |
| 5 | 1.4 |
| 6 | 0.5 |

In five out of six subjects (subject no. 1, 2, 4, 5 and 6), a virus neutralizing titer of at least 0.5 IU/ml was detected on day 42. According to the WHO standard, a protective antibody response has thus been achieved in these subjects, demonstrating the efficacy of the immunization with the mRNA according to the invention.

CONCLUSION

According to preliminary results from the ongoing clinical trial, the use of the mRNA according to the invention for immunization of human subjects has a favourable safety profile. The efficacy of the approach has been demonstrated by these preliminary studies with a protective antibody response (VNT≥0.5 IU/ml) achieved in five out of six investigated subjects on day 42.

The invention claimed is:

1. A method of stimulating a protective immune response to rabies virus in a subject comprising administering to the subject a pharmaceutical composition comprising a purified mRNA molecule, said mRNA comprising:

(a) a 5' Cap;

(b) an open reading frame (ORF) encoding a Rabies virus glycoprotein (RAV-G), wherein the ORF comprises a sequence having at least about 95% identity to the protein coding region of SEQ ID NO: 24; and (c) a Poly(A) sequence, wherein the composition is administered by injection.

2. The method of claim 1, wherein the composition is administered by intramuscular or intradermal injection.

3. The method of claim 2, wherein the composition is administered by intramuscular injection.

4. The method of claim 1, wherein the 5' Cap is a m7GpppN Cap.

5. The method of claim 1, wherein the mRNA comprises, from 5' to 3':

(a) a 5' Cap;

(b) an open reading frame (ORF) encoding a Rabies virus glycoprotein (RAV-G); and (c) a 3' untranslated region (UTR), including the Poly(A) sequence.

6. The method of claim 5, wherein the Poly(A) sequence comprises 50 to 250 adenosine nucleotides.

7. The method of claim 6, wherein the mRNA further comprises a 5' UTR sequence.

8. The method of claim 7, wherein the 5'UTR is derived from the 5'-UTR of a TOP gene.

9. The method of claim 6, wherein the 3' UTR further comprises a histone stem-loop sequence.

10. The method of claim 6, wherein the ORF has a G/C content that is increased compared with the G/C content an ORF from an original sequence encoding RAV-G.

11. The method of claim 6, wherein the mRNA is formulated with a cationic or polycationic compound.

12. The method of claim 11, wherein the a cationic or polycationic compound comprises a cationic lipid.

13. The method of claim 7, wherein the mRNA comprises at least one base-modified nucleotide.

14. The method of claim 7, wherein the poly(A) sequence is located at the 3' terminus of the mRNA.

15. A method of stimulating a protective immune response to rabies virus in a subject comprising administering to the subject a pharmaceutical composition comprising a purified mRNA molecule, said mRNA comprising:

(a) a 5' Cap;

(b) a 5' untranslated region (UTR);

(c) an open reading frame (ORF) encoding a Rabies virus glycoprotein (RAV-G), wherein the ORF comprises a sequence having at least about 95% identity to the protein coding region of SEQ ID NO: 24;

(d) a 3' UTR; and (e) a Poly(A) sequence, wherein the composition is administered by intramuscular injection and wherein the mRNA is formulated with cationic lipid.

16. The method of claim 15, wherein the ORF has a G/C content that is increased compared with the G/C content an ORF from an original sequence encoding RAV-G or an antigenic fragment thereof.

17. The method of claim 15, wherein the RAV-G is a full length RAV-G.

18. The method of claim 15, wherein the mRNA comprises at least one base-modified nucleotide.

* * * * *

SEQUENCE LISTING

```
<160> NUMBER OF SEQ ID NOS: 27

<210> SEQ ID NO 1
<211> LENGTH: 524
<212> TYPE: PRT
<213> ORGANISM: Rabies virus

<400> SEQUENCE: 1

Met Val Pro Gln Ala Leu Leu Phe Val Pro Leu Leu Val Phe Pro Leu
1               5                   10                  15

Cys Phe Gly Lys Phe Pro Ile Tyr Thr Ile Pro Asp Lys Leu Gly Pro
            20                  25                  30

Trp Ser Pro Ile Asp Ile His His Leu Ser Cys Pro Asn Asn Leu Val
        35                  40                  45

Val Glu Asp Glu Gly Cys Thr Asn Leu Ser Gly Phe Ser Tyr Met Glu
    50                  55                  60

Leu Lys Val Gly Tyr Ile Ser Ala Ile Lys Met Asn Gly Phe Thr Cys
65                  70                  75                  80

Thr Gly Val Val Thr Glu Ala Glu Thr Tyr Thr Asn Phe Val Gly Tyr
                85                  90                  95

Val Thr Thr Thr Phe Lys Arg Lys His Phe Arg Pro Thr Pro Asp Ala
            100                 105                 110

Cys Arg Ala Ala Tyr Asn Trp Lys Met Ala Gly Asp Pro Arg Tyr Glu
        115                 120                 125

Glu Ser Leu His Asn Pro Tyr Pro Asp Tyr His Trp Leu Arg Thr Val
    130                 135                 140
```

-continued

Lys Thr Thr Lys Glu Ser Leu Val Ile Ile Ser Pro Ser Val Ala Asp
145                 150                 155                 160

Leu Asp Pro Tyr Asp Arg Ser Leu His Ser Arg Val Phe Pro Gly Gly
            165                 170                 175

Asn Cys Ser Gly Val Ala Val Ser Ser Thr Tyr Cys Ser Thr Asn His
            180                 185                 190

Asp Tyr Thr Ile Trp Met Pro Glu Asn Pro Arg Leu Gly Met Ser Cys
            195                 200                 205

Asp Ile Phe Thr Asn Ser Arg Gly Lys Arg Ala Ser Lys Gly Ser Glu
            210                 215                 220

Thr Cys Gly Phe Val Asp Glu Arg Gly Leu Tyr Lys Ser Leu Lys Gly
225                 230                 235                 240

Ala Cys Lys Leu Lys Leu Cys Gly Val Leu Gly Leu Arg Leu Met Asp
            245                 250                 255

Gly Thr Trp Val Ala Met Gln Thr Ser Asn Glu Thr Lys Trp Cys Pro
            260                 265                 270

Pro Gly Gln Leu Val Asn Leu His Asp Phe Arg Ser Asp Glu Ile Glu
            275                 280                 285

His Leu Val Val Glu Glu Leu Val Lys Lys Arg Glu Glu Cys Leu Asp
            290                 295                 300

Ala Leu Glu Ser Ile Met Thr Thr Lys Ser Val Ser Phe Arg Arg Leu
305                 310                 315                 320

Ser His Leu Arg Lys Leu Val Pro Gly Phe Gly Lys Ala Tyr Thr Ile
            325                 330                 335

Phe Asn Lys Thr Leu Met Glu Ala Asp Ala His Tyr Lys Ser Val Arg
            340                 345                 350

Thr Trp Asn Glu Ile Ile Pro Ser Lys Gly Cys Leu Arg Val Gly Gly
            355                 360                 365

Arg Cys His Pro His Val Asn Gly Val Phe Phe Asn Gly Ile Ile Leu
            370                 375                 380

Gly Pro Asp Gly Asn Val Leu Ile Pro Glu Met Gln Ser Ser Leu Leu
385                 390                 395                 400

Gln Gln His Met Glu Leu Leu Val Ser Ser Val Ile Pro Leu Met His
            405                 410                 415

Pro Leu Ala Asp Pro Ser Thr Val Phe Lys Asn Gly Asp Glu Ala Glu
            420                 425                 430

Asp Phe Val Glu Val His Leu Pro Asp Val His Glu Arg Ile Ser Gly
            435                 440                 445

Val Asp Leu Gly Leu Pro Asn Trp Gly Lys Tyr Val Leu Leu Ser Ala
            450                 455                 460

Gly Ala Leu Thr Ala Leu Met Leu Ile Ile Phe Leu Met Thr Cys Trp
465                 470                 475                 480

Arg Arg Val Asn Arg Ser Glu Pro Thr Gln His Asn Leu Arg Gly Thr
            485                 490                 495

Gly Arg Glu Val Ser Val Thr Pro Gln Ser Gly Lys Ile Ile Ser Ser
            500                 505                 510

Trp Glu Ser Tyr Lys Ser Gly Gly Glu Thr Gly Leu
            515                 520

<210> SEQ ID NO 2
<211> LENGTH: 450
<212> TYPE: PRT
<213> ORGANISM: Rabies virus

<400> SEQUENCE: 2

```
Met Asp Ala Asp Lys Ile Val Phe Lys Val Asn Asn Gln Val Val Ser
1               5                   10                  15
Leu Lys Pro Glu Ile Ile Val Asp Gln Tyr Glu Tyr Lys Tyr Pro Ala
            20                  25                  30
Ile Lys Asp Leu Lys Lys Pro Cys Ile Thr Leu Gly Lys Ala Pro Asp
        35                  40                  45
Leu Asn Lys Ala Tyr Lys Ser Val Leu Ser Cys Met Ser Ala Ala Lys
    50                  55                  60
Leu Asp Pro Asp Val Cys Ser Tyr Leu Ala Ala Met Gln Phe
65                  70                  75                  80
Phe Glu Gly Thr Cys Pro Glu Asp Trp Thr Ser Tyr Gly Ile Val Ile
                85                  90                  95
Ala Arg Lys Gly Asp Lys Ile Thr Pro Gly Ser Leu Val Glu Ile Lys
            100                 105                 110
Arg Thr Asp Val Glu Gly Asn Trp Ala Leu Thr Gly Gly Met Glu Leu
        115                 120                 125
Thr Arg Asp Pro Thr Val Pro Glu His Ala Ser Leu Val Gly Leu Leu
    130                 135                 140
Leu Ser Leu Tyr Arg Leu Ser Lys Ile Ser Gly Gln Ser Thr Gly Asn
145                 150                 155                 160
Tyr Lys Thr Asn Ile Ala Asp Arg Ile Glu Gln Ile Phe Glu Thr Ala
                165                 170                 175
Pro Phe Val Lys Ile Val Glu His His Thr Leu Met Thr Thr His Lys
            180                 185                 190
Met Cys Ala Asn Trp Ser Thr Ile Pro Asn Phe Arg Phe Leu Ala Gly
        195                 200                 205
Thr Tyr Asp Met Phe Phe Ser Arg Ile Glu His Leu Tyr Ser Ala Ile
    210                 215                 220
Arg Val Gly Thr Val Thr Ala Tyr Glu Asp Cys Ser Gly Leu Val
225                 230                 235                 240
Ser Phe Thr Gly Phe Ile Lys Gln Ile Asn Leu Thr Ala Arg Glu Ala
                245                 250                 255
Ile Leu Tyr Phe Phe His Lys Asn Phe Glu Glu Ile Arg Arg Met
            260                 265                 270
Phe Glu Pro Gly Gln Glu Thr Ala Val Pro His Ser Tyr Phe Ile His
        275                 280                 285
Phe Arg Ser Leu Gly Leu Ser Gly Lys Ser Pro Tyr Ser Ser Asn Ala
    290                 295                 300
Val Gly His Val Phe Asn Leu Ile His Phe Val Gly Cys Tyr Met Gly
305                 310                 315                 320
Gln Val Arg Ser Leu Asn Ala Thr Val Ile Ala Ala Cys Ala Pro His
                325                 330                 335
Glu Met Ser Val Leu Gly Gly Tyr Leu Gly Glu Glu Phe Phe Gly Lys
            340                 345                 350
Gly Thr Phe Glu Arg Arg Phe Phe Arg Asp Glu Lys Glu Leu Gln Glu
        355                 360                 365
Tyr Glu Ala Ala Glu Leu Thr Lys Thr Asp Val Ala Leu Ala Asp Asp
    370                 375                 380
Gly Thr Val Asn Ser Asp Asp Glu Asp Tyr Phe Ser Gly Glu Thr Arg
385                 390                 395                 400
Ser Pro Glu Ala Val Tyr Thr Arg Ile Ile Met Asn Gly Gly Arg Leu
                405                 410                 415
```

```
Lys Arg Ser His Ile Arg Arg Tyr Val Ser Val Ser Asn His Gln
            420                 425                 430

Ala Arg Pro Asn Ser Phe Ala Glu Phe Leu Asn Lys Thr Tyr Ser Ser
            435                 440                 445

Asp Ser
    450

<210> SEQ ID NO 3
<211> LENGTH: 297
<212> TYPE: PRT
<213> ORGANISM: Rabies virus

<400> SEQUENCE: 3

Met Ser Lys Ile Phe Val Asn Pro Ser Ala Ile Arg Ala Gly Leu Ala
1               5                   10                  15

Asp Leu Glu Met Ala Glu Glu Thr Val Asp Leu Ile Asn Arg Asn Ile
            20                  25                  30

Glu Asp Asn Gln Ala His Leu Gln Gly Glu Pro Ile Glu Val Asp Asn
        35                  40                  45

Leu Pro Glu Asp Met Gly Arg Leu His Leu Asp Asp Gly Lys Ser Pro
50                  55                  60

Asn Pro Gly Glu Met Ala Lys Val Gly Glu Gly Lys Tyr Arg Glu Asp
65                  70                  75                  80

Phe Gln Met Asp Glu Gly Glu Asp Pro Ser Leu Leu Phe Gln Ser Tyr
                85                  90                  95

Leu Asp Asn Val Gly Val Gln Ile Val Arg Gln Ile Arg Ser Gly Glu
            100                 105                 110

Arg Phe Leu Lys Ile Trp Ser Gln Thr Val Glu Glu Ile Ile Ser Tyr
        115                 120                 125

Val Ala Val Asn Phe Pro Asn Pro Pro Gly Lys Ser Ser Glu Asp Lys
130                 135                 140

Ser Thr Gln Thr Thr Gly Arg Glu Leu Lys Lys Glu Thr Thr Pro Thr
145                 150                 155                 160

Pro Ser Gln Arg Glu Ser Gln Ser Ser Lys Ala Arg Met Ala Ala Gln
                165                 170                 175

Thr Ala Ser Gly Pro Pro Ala Leu Glu Trp Ser Ala Thr Asn Glu Glu
            180                 185                 190

Asp Asp Leu Ser Val Glu Ala Glu Ile Ala His Gln Ile Ala Glu Ser
        195                 200                 205

Phe Ser Lys Lys Tyr Lys Phe Pro Ser Arg Ser Ser Gly Ile Leu Leu
210                 215                 220

Tyr Asn Phe Glu Gln Leu Lys Met Asn Leu Asp Asp Ile Val Lys Glu
225                 230                 235                 240

Ala Lys Asn Val Pro Gly Val Thr Arg Leu Ala Arg Asp Gly Ser Lys
                245                 250                 255

Leu Pro Leu Arg Cys Val Leu Gly Trp Val Ala Leu Ala Asn Ser Lys
            260                 265                 270

Lys Phe Gln Leu Leu Val Glu Ser Asn Lys Leu Ser Lys Ile Met Gln
        275                 280                 285

Asp Asp Leu Asn Arg Tyr Thr Ser Cys
        290                 295

<210> SEQ ID NO 4
<211> LENGTH: 202
<212> TYPE: PRT
```

<213> ORGANISM: Rabies virus

<400> SEQUENCE: 4

```
Met Asn Phe Leu Arg Lys Ile Val Lys Asn Cys Arg Asp Glu Asp Thr
1               5                   10                  15

Gln Lys Pro Ser Pro Val Ser Ala Pro Leu Asp Asp Asp Asp Leu Trp
            20                  25                  30

Leu Pro Pro Pro Glu Tyr Val Pro Leu Lys Glu Leu Thr Ser Lys Lys
        35                  40                  45

Asn Arg Arg Asn Phe Cys Ile Asn Gly Gly Val Lys Val Cys Ser Pro
    50                  55                  60

Asn Gly Tyr Ser Phe Gly Ile Leu Arg His Ile Leu Arg Ser Phe Asp
65                  70                  75                  80

Glu Ile Tyr Ser Gly Asn His Arg Met Val Gly Leu Val Lys Val Val
                85                  90                  95

Ile Gly Leu Ala Leu Ser Gly Ala Pro Val Pro Glu Gly Met Asn Trp
            100                 105                 110

Val Tyr Lys Leu Arg Arg Thr Leu Ile Phe Gln Trp Ala Asp Ser Arg
        115                 120                 125

Gly Pro Leu Glu Gly Glu Glu Leu Glu Tyr Ser Gln Glu Ile Thr Trp
    130                 135                 140

Asp Asp Asn Thr Glu Phe Val Gly Leu Gln Ile Arg Val Ser Ala Lys
145                 150                 155                 160

Gln Cys His Ile Arg Gly Arg Ile Trp Cys Ile Asn Met Asn Ser Arg
                165                 170                 175

Ala Gly Gln Leu Trp Ser Asp Met Ser Leu Gln Thr Gln Arg Ser Glu
            180                 185                 190

Glu Asp Lys Asp Ser Ser Leu Leu Leu Glu
        195                 200
```

<210> SEQ ID NO 5
<211> LENGTH: 2142
<212> TYPE: PRT
<213> ORGANISM: Rabies virus

<400> SEQUENCE: 5

```
Met Leu Asp Pro Gly Glu Val Tyr Asp Asp Pro Ile Asp Pro Ile Glu
1               5                   10                  15

Leu Glu Ala Glu Pro Arg Gly Thr Pro Thr Val Pro Asn Ile Leu Arg
            20                  25                  30

Asn Ser Asp Tyr Asn Leu Asn Ser Pro Leu Ile Glu Asp Pro Ala Arg
        35                  40                  45

Leu Met Leu Glu Trp Leu Lys Thr Gly Asn Arg Pro Tyr Arg Met Thr
    50                  55                  60

Leu Thr Asp Asn Cys Ser Arg Ser Phe Arg Val Leu Lys Asp Tyr Phe
65                  70                  75                  80

Lys Lys Val Asp Leu Gly Ser Leu Lys Val Gly Gly Met Ala Ala Gln
                85                  90                  95

Ser Met Ile Ser Leu Trp Leu Tyr Gly Ala His Ser Glu Ser Asn Arg
            100                 105                 110

Ser Arg Arg Cys Ile Thr Asp Leu Ala His Phe Tyr Ser Lys Ser Ser
        115                 120                 125

Pro Ile Glu Lys Leu Leu Asn Leu Thr Leu Gly Asn Arg Gly Leu Arg
    130                 135                 140

Ile Pro Pro Glu Gly Val Leu Ser Cys Leu Glu Arg Val Asp Tyr Asp
```

-continued

```
            145                 150                 155                 160
Asn Ala Phe Gly Arg Tyr Leu Ala Asn Thr Tyr Ser Ser Tyr Leu Phe
                165                 170                 175
Phe His Val Ile Thr Leu Tyr Met Asn Ala Leu Asp Trp Asp Glu Glu
                180                 185                 190
Lys Thr Ile Leu Ala Leu Trp Lys Asp Leu Thr Ser Val Asp Ile Gly
                195                 200                 205
Lys Asp Leu Val Lys Phe Lys Asp Gln Ile Trp Gly Leu Leu Ile Val
                210                 215                 220
Thr Lys Asp Phe Val Tyr Ser Gln Ser Ser Asn Cys Leu Phe Asp Arg
225                 230                 235                 240
Asn Tyr Thr Leu Met Leu Lys Asp Leu Phe Leu Ser Arg Phe Asn Ser
                245                 250                 255
Leu Met Val Leu Leu Ser Pro Pro Glu Pro Arg Tyr Ser Asp Asp Leu
                260                 265                 270
Ile Ser Gln Leu Cys Gln Leu Tyr Ile Ala Gly Asp Gln Val Leu Ser
                275                 280                 285
Met Cys Gly Asn Ser Gly Tyr Glu Val Ile Lys Ile Leu Glu Pro Tyr
                290                 295                 300
Val Val Asn Ser Leu Val Gln Arg Ala Glu Lys Phe Arg Pro Leu Ile
305                 310                 315                 320
His Ser Leu Gly Asp Phe Pro Val Phe Ile Lys Asp Lys Val Ser Gln
                325                 330                 335
Leu Glu Glu Thr Phe Gly Ser Cys Ala Arg Arg Phe Phe Arg Ala Leu
                340                 345                 350
Asp Gln Phe Asp Asn Ile His Asp Leu Val Phe Val Tyr Gly Cys Tyr
                355                 360                 365
Arg His Trp Gly His Pro Tyr Ile Asp Tyr Arg Lys Gly Leu Ser Lys
                370                 375                 380
Leu Tyr Asp Gln Val His Ile Lys Lys Val Ile Asp Lys Ser Tyr Gln
385                 390                 395                 400
Glu Cys Leu Ala Ser Asp Leu Ala Arg Arg Ile Leu Arg Trp Gly Phe
                405                 410                 415
Asp Lys Tyr Ser Lys Trp Tyr Leu Asp Ser Arg Phe Leu Ala Arg Asp
                420                 425                 430
His Pro Leu Thr Pro Tyr Ile Lys Thr Gln Thr Trp Pro Pro Lys His
                435                 440                 445
Ile Val Asp Leu Val Gly Asp Thr Trp His Lys Leu Pro Ile Thr Gln
450                 455                 460
Ile Phe Glu Ile Pro Glu Ser Met Asp Pro Ser Glu Ile Leu Asp Asp
465                 470                 475                 480
Lys Ser His Ser Phe Thr Arg Thr Arg Leu Ala Ser Trp Leu Ser Glu
                485                 490                 495
Asn Arg Gly Gly Pro Val Pro Ser Glu Lys Val Ile Ile Thr Ala Leu
                500                 505                 510
Ser Lys Pro Pro Val Asn Pro Arg Glu Phe Leu Lys Ser Ile Asp Leu
                515                 520                 525
Gly Gly Leu Pro Asp Glu Asp Leu Ile Ile Gly Leu Lys Pro Lys Glu
                530                 535                 540
Arg Glu Leu Lys Ile Glu Gly Arg Phe Phe Ala Leu Met Ser Trp Asn
545                 550                 555                 560
Leu Arg Leu Tyr Phe Val Ile Thr Glu Lys Leu Leu Ala Asn Tyr Ile
                565                 570                 575
```

```
Leu Pro Leu Phe Asp Ala Leu Thr Met Thr Asp Asn Leu Asn Lys Val
            580                 585                 590

Phe Lys Lys Leu Ile Asp Arg Val Thr Gly Gln Gly Leu Leu Asp Tyr
            595                 600                 605

Ser Arg Val Thr Tyr Ala Phe His Leu Asp Tyr Glu Lys Trp Asn Asn
            610                 615                 620

His Gln Arg Leu Glu Ser Thr Glu Asp Val Phe Ser Val Leu Asp Gln
625                 630                 635                 640

Val Phe Gly Leu Lys Arg Val Phe Ser Arg Thr His Glu Phe Phe Gln
                645                 650                 655

Lys Ser Trp Ile Tyr Tyr Ser Asp Arg Ser Asp Leu Ile Gly Leu Arg
            660                 665                 670

Glu Asp Gln Ile Tyr Cys Leu Asp Ala Ser Asn Gly Pro Thr Cys Trp
            675                 680                 685

Asn Gly Gln Asp Gly Gly Leu Glu Gly Leu Arg Gln Lys Gly Trp Ser
            690                 695                 700

Leu Val Ser Leu Leu Met Ile Asp Arg Glu Ser Gln Ile Arg Asn Thr
705                 710                 715                 720

Arg Thr Lys Val Leu Ala Gln Gly Asp Asn Gln Val Leu Cys Pro Thr
                725                 730                 735

Tyr Met Leu Ser Pro Gly Leu Ser Gln Glu Gly Leu Leu Tyr Glu Leu
            740                 745                 750

Glu Ser Ile Ser Arg Asn Ala Phe Ser Ile Tyr Arg Ala Val Glu Glu
            755                 760                 765

Gly Ala Ser Lys Leu Gly Leu Ile Ile Lys Lys Glu Thr Met Cys
            770                 775                 780

Ser Tyr Asp Phe Leu Ile Tyr Gly Lys Thr Pro Leu Phe Arg Gly Asn
785                 790                 795                 800

Ile Leu Val Pro Glu Ser Lys Arg Trp Ala Arg Val Ser Cys Val Ser
                805                 810                 815

Asn Asp Gln Ile Val Asn Leu Ala Asn Ile Met Ser Thr Val Ser Thr
            820                 825                 830

Asn Ala Leu Thr Val Ala Gln His Ser Gln Ser Leu Ile Lys Pro Met
            835                 840                 845

Arg Asp Phe Leu Leu Met Ser Val Gln Ala Val Phe His Tyr Leu Leu
850                 855                 860

Phe Ser Pro Ile Leu Lys Gly Arg Val Tyr Lys Ile Leu Ser Ala Glu
865                 870                 875                 880

Gly Glu Ser Phe Leu Leu Ala Met Ser Arg Ile Ile Tyr Leu Asp Pro
                885                 890                 895

Ser Leu Gly Gly Val Ser Gly Met Ser Leu Gly Arg Phe His Ile Arg
            900                 905                 910

Gln Phe Ser Asp Pro Val Ser Glu Gly Leu Ser Phe Trp Arg Glu Ile
            915                 920                 925

Trp Leu Ser Ser His Glu Ser Trp Ile His Ala Leu Cys Gln Glu Ala
            930                 935                 940

Gly Asn Pro Asp Leu Gly Glu Arg Thr Leu Glu Ser Phe Thr Arg Leu
945                 950                 955                 960

Leu Glu Asp Pro Thr Thr Leu Asn Ile Arg Gly Gly Ala Ser Pro Thr
                965                 970                 975

Ile Leu Leu Lys Asp Ala Ile Arg Lys Ala Leu Tyr Asp Glu Val Asp
            980                 985                 990
```

```
Lys Val Glu Asn Ser Glu Phe Arg  Glu Ala Ile Leu Leu  Ser Lys Thr
    995                 1000                     1005

His Arg Asp Asn Phe Ile Leu  Phe Leu Thr Ser Val  Glu Pro Leu
    1010                1015                 1020

Phe Pro Arg Phe Leu Ser Glu  Leu Phe Ser Ser Ser  Phe Leu Gly
    1025                1030                 1035

Ile Pro Glu Ser Ile Ile Gly  Leu Ile Gln Asn Ser  Arg Thr Ile
    1040                1045                 1050

Arg Arg Gln Phe Arg Lys Ser  Leu Ser Lys Thr Leu  Glu Glu Ser
    1055                1060                 1065

Phe Tyr Asn Ser Glu Ile His  Gly Ile Ser Arg Met  Thr Gln Thr
    1070                1075                 1080

Pro Gln Arg Val Gly Gly Val  Trp Pro Cys Ser Ser  Glu Arg Ala
    1085                1090                 1095

Asp Leu Leu Arg Glu Ile Ser  Trp Gly Arg Lys Val  Val Gly Thr
    1100                1105                 1110

Thr Val Pro His Pro Ser Glu  Met Leu Gly Leu Leu  Pro Lys Ser
    1115                1120                 1125

Ser Ile Ser Cys Thr Cys Gly  Ala Thr Gly Gly Gly  Asn Pro Arg
    1130                1135                 1140

Val Ser Val Ser Val Leu Pro  Ser Phe Asp Gln Ser  Phe Phe Cys
    1145                1150                 1155

Thr Gly Pro Leu Lys Gly Tyr  Leu Gly Ser Ser Thr  Ser Met Ser
    1160                1165                 1170

Thr Gln Leu Phe His Ala Trp  Glu Lys Val Thr Asn  Val His Val
    1175                1180                 1185

Val Lys Arg Ala Leu Ser Leu  Lys Glu Ser Ile Asn  Trp Phe Ile
    1190                1195                 1200

Thr Arg Asp Ser Asn Leu Ala  Gln Thr Leu Ile Arg  Asn Ile Val
    1205                1210                 1215

Ser Leu Thr Gly Pro Asp Phe  Pro Leu Glu Glu Ala  Pro Val Phe
    1220                1225                 1230

Lys Arg Thr Gly Ser Ala Leu  His Arg Phe Lys Ser  Ala Arg Tyr
    1235                1240                 1245

Ser Glu Gly Gly Tyr Ser Ser  Val Cys Pro Asn Leu  Leu Ser His
    1250                1255                 1260

Ile Ser Val Ser Thr Asp Thr  Met Ser Asp Leu Thr  Gln Asp Gly
    1265                1270                 1275

Lys Asn Tyr Asp Phe Met Phe  Gln Pro Leu Met Leu  Tyr Ala Gln
    1280                1285                 1290

Thr Trp Thr Ser Glu Leu Val  Gln Arg Asp Thr Arg  Leu Arg Asp
    1295                1300                 1305

Ser Thr Phe His Trp His Leu  Gln Cys Asn Arg Cys  Val Arg Pro
    1310                1315                 1320

Ile Asp Asp Val Thr Leu Glu  Thr Ser Gln Ile Phe  Glu Phe Pro
    1325                1330                 1335

Asp Val Ser Lys Arg Ile Ser  Arg Met Val Ser Gly  Ala Val Pro
    1340                1345                 1350

His Phe Gln Arg Leu Pro Asp  Ile Arg Leu Arg Pro  Gly Asp Phe
    1355                1360                 1365

Glu Ser Leu Ser Gly Arg Glu  Lys Ser His His Ile  Gly Ser Ala
    1370                1375                 1380

Gln Gly Leu Leu Tyr Ser Ile  Leu Val Ala Ile His  Asp Ser Gly
```

-continued

```
                1385                1390                1395
Tyr Asn Asp Gly Thr Ile Phe Pro Val Asn Ile Tyr Gly Lys Val
                1400                1405                1410
Ser Pro Arg Asp Tyr Leu Arg Gly Leu Ala Arg Gly Val Leu Ile
                1415                1420                1425
Gly Ser Ser Ile Cys Phe Leu Thr Arg Met Thr Asn Ile Asn Ile
                1430                1435                1440
Asn Arg Pro Leu Glu Leu Ile Ser Gly Val Ile Ser Tyr Ile Leu
                1445                1450                1455
Leu Arg Leu Asp Asn His Pro Ser Leu Tyr Ile Met Leu Arg Glu
                1460                1465                1470
Pro Ser Phe Arg Glu Glu Ile Phe Ser Ile Pro Gln Lys Ile Pro
                1475                1480                1485
Ala Ala Tyr Pro Thr Thr Met Lys Glu Gly Asn Arg Ser Ile Leu
                1490                1495                1500
Cys Tyr Leu Gln His Val Leu Arg Tyr Glu Arg Glu Val Ile Thr
                1505                1510                1515
Ala Ser Pro Glu Asn Asp Trp Leu Trp Ile Phe Ser Asp Phe Arg
                1520                1525                1530
Ser Ala Lys Met Thr Tyr Leu Thr Leu Ile Thr Tyr Gln Ser His
                1535                1540                1545
Leu Leu Leu Gln Arg Val Glu Arg Asn Leu Ser Lys Ser Met Arg
                1550                1555                1560
Asp Asn Leu Arg Gln Leu Ser Ser Leu Met Arg Gln Val Leu Gly
                1565                1570                1575
Gly His Gly Glu Asp Thr Leu Glu Ser Asp Asp Asn Ile Gln Arg
                1580                1585                1590
Leu Leu Lys Asp Ser Leu Arg Arg Thr Arg Trp Val Asp Gln Glu
                1595                1600                1605
Val Arg His Ala Ala Arg Thr Met Thr Gly Asp Tyr Ser Pro Asn
                1610                1615                1620
Lys Lys Val Ser Arg Lys Val Gly Cys Ser Glu Trp Val Cys Ser
                1625                1630                1635
Ala Gln Gln Val Ala Val Ser Thr Ser Ala Asn Pro Ala Pro Val
                1640                1645                1650
Ser Glu Leu Asp Ile Arg Ala Leu Ser Lys Arg Phe Gln Asn Pro
                1655                1660                1665
Leu Ile Ser Gly Leu Arg Val Val Gln Trp Ala Thr Gly Ala His
                1670                1675                1680
Tyr Lys Leu Lys Pro Ile Leu Asp Asp Leu Asn Val Phe Pro Ser
                1685                1690                1695
Leu Cys Leu Val Val Gly Asp Gly Ser Gly Gly Ile Ser Arg Ala
                1700                1705                1710
Val Leu Asn Met Phe Pro Asp Ala Lys Leu Val Phe Asn Ser Leu
                1715                1720                1725
Leu Glu Val Asn Asp Leu Met Ala Ser Gly Thr His Pro Leu Pro
                1730                1735                1740
Pro Ser Ala Ile Met Arg Gly Gly Asn Asp Ile Val Ser Arg Val
                1745                1750                1755
Ile Asp Phe Asp Ser Ile Trp Glu Lys Pro Ser Asp Leu Arg Asn
                1760                1765                1770
Leu Ala Thr Trp Lys Tyr Phe Gln Ser Val Gln Lys Gln Val Asn
                1775                1780                1785
```

-continued

Met Ser Tyr Asp Leu Ile Ile Cys Asp Ala Glu Val Thr Asp Ile
1790            1795                1800

Ala Ser Ile Asn Arg Ile Thr Leu Leu Met Ser Asp Phe Ala Leu
1805            1810                1815

Ser Ile Asp Gly Pro Leu Tyr Leu Val Phe Lys Thr Tyr Gly Thr
1820            1825                1830

Met Leu Val Asn Pro Asn Tyr Lys Ala Ile Gln His Leu Ser Arg
1835            1840                1845

Ala Phe Pro Ser Val Thr Gly Phe Ile Thr Gln Val Thr Ser Ser
1850            1855                1860

Phe Ser Ser Glu Leu Tyr Leu Arg Phe Ser Lys Arg Gly Lys Phe
1865            1870                1875

Phe Arg Asp Ala Glu Tyr Leu Thr Ser Ser Thr Leu Arg Glu Met
1880            1885                1890

Ser Leu Val Leu Phe Asn Cys Ser Ser Pro Lys Ser Glu Met Gln
1895            1900                1905

Arg Ala Arg Ser Leu Asn Tyr Gln Asp Leu Val Arg Gly Phe Pro
1910            1915                1920

Glu Glu Ile Ile Ser Asn Pro Tyr Asn Glu Met Ile Ile Thr Leu
1925            1930                1935

Ile Asp Ser Asp Val Glu Ser Phe Leu Val His Lys Met Val Asp
1940            1945                1950

Asp Leu Glu Leu Gln Arg Gly Thr Leu Ser Lys Val Ala Ile Ile
1955            1960                1965

Ile Ala Ile Met Ile Val Phe Ser Asn Arg Val Phe Asn Val Ser
1970            1975                1980

Lys Pro Leu Thr Asp Pro Leu Phe Tyr Pro Pro Ser Asp Pro Lys
1985            1990                1995

Ile Leu Arg His Phe Asn Ile Cys Cys Ser Thr Met Met Tyr Leu
2000            2005                2010

Ser Thr Ala Leu Gly Asp Val Pro Ser Phe Ala Arg Leu His Asp
2015            2020                2025

Leu Tyr Asn Arg Pro Ile Thr Tyr Tyr Phe Arg Lys Gln Val Ile
2030            2035                2040

Leu Gly Asn Val Tyr Leu Ser Trp Ser Trp Ser Asn Asp Thr Ser
2045            2050                2055

Val Phe Lys Arg Val Ala Cys Asn Ser Ser Leu Ser Leu Ser Ser
2060            2065                2070

His Trp Ile Arg Leu Ile Tyr Lys Ile Val Lys Thr Thr Arg Leu
2075            2080                2085

Val Gly Ser Ile Lys Asp Leu Ser Gly Glu Val Glu Arg His Leu
2090            2095                2100

His Arg Tyr Asn Arg Trp Ile Thr Leu Glu Asn Ile Arg Ser Arg
2105            2110                2115

Ser Ser Leu Leu Asp Tyr Ser Cys Leu Cys Ile Gly Tyr Ser Trp
2120            2125                2130

Lys Pro Ala His Ala Lys Thr Leu Val
2135            2140

<210> SEQ ID NO 6
<211> LENGTH: 524
<212> TYPE: PRT
<213> ORGANISM: Rabies virus

```
<400> SEQUENCE: 6

Met Val Pro Gln Val Leu Leu Phe Val Pro Leu Leu Gly Phe Ser Leu
1               5                   10                  15

Cys Phe Gly Lys Phe Pro Ile Tyr Thr Ile Pro Asp Lys Leu Gly Pro
            20                  25                  30

Trp Ser Pro Ile Asp Ile His His Leu Ser Cys Pro Asn Asn Leu Val
        35                  40                  45

Val Glu Asp Glu Gly Cys Thr Asn Leu Ser Glu Phe Ser Tyr Met Glu
    50                  55                  60

Leu Lys Val Gly Tyr Ile Ser Ala Ile Lys Val Asn Gly Phe Thr Cys
65                  70                  75                  80

Thr Gly Val Val Thr Glu Ala Glu Thr Tyr Thr Asn Phe Val Gly Tyr
                85                  90                  95

Val Thr Thr Thr Phe Lys Arg Lys His Phe Arg Pro Thr Pro Asp Ala
                100                 105                 110

Cys Arg Ala Ala Tyr Asn Trp Lys Met Ala Gly Asp Pro Arg Tyr Glu
            115                 120                 125

Glu Ser Leu His Asn Pro Tyr Pro Asp Tyr His Trp Leu Arg Thr Val
    130                 135                 140

Lys Thr Thr Lys Glu Ser Leu Val Ile Ile Ser Pro Ser Val Thr Asp
145                 150                 155                 160

Leu Asp Pro Tyr Asp Lys Ser Leu His Ser Arg Val Phe Pro Gly Gly
                165                 170                 175

Asn Cys Ser Gly Ile Thr Val Ser Ser Thr Tyr Cys Ser Thr Asn His
            180                 185                 190

Asp Tyr Thr Ile Trp Met Pro Glu Asn Leu Arg Leu Gly Thr Ser Cys
    195                 200                 205

Asp Ile Phe Thr Asn Ser Arg Gly Lys Arg Ala Ser Lys Gly Gly Lys
210                 215                 220

Thr Cys Gly Phe Val Asp Glu Arg Gly Leu Tyr Lys Ser Leu Lys Gly
225                 230                 235                 240

Ala Cys Lys Leu Lys Leu Cys Gly Val Leu Gly Leu Arg Leu Met Asp
                245                 250                 255

Gly Thr Trp Val Ala Met Gln Thr Ser Asp Glu Thr Lys Trp Cys Pro
                260                 265                 270

Pro Gly Gln Leu Val Asn Leu His Asp Phe Arg Ser Asp Glu Ile Glu
            275                 280                 285

His Leu Val Val Glu Glu Leu Val Lys Lys Arg Glu Glu Cys Leu Asp
    290                 295                 300

Ala Leu Glu Ser Ile Met Thr Thr Lys Ser Val Ser Phe Arg Arg Leu
305                 310                 315                 320

Ser His Leu Arg Lys Leu Val Pro Gly Phe Gly Lys Ala Tyr Thr Ile
                325                 330                 335

Phe Asn Lys Thr Leu Met Glu Ala Asp Ala His Tyr Lys Ser Val Arg
                340                 345                 350

Thr Trp Asn Glu Ile Ile Pro Ser Lys Gly Cys Leu Arg Val Gly Gly
                355                 360                 365

Arg Cys His Pro His Val Asn Gly Val Phe Phe Asn Gly Ile Ile Leu
            370                 375                 380

Gly Ser Asp Gly His Val Leu Ile Pro Glu Met Gln Ser Ser Leu Leu
385                 390                 395                 400

Gln Gln His Met Glu Leu Leu Glu Ser Ser Val Ile Pro Leu Met His
                405                 410                 415
```

```
Pro Leu Ala Asp Pro Ser Thr Val Phe Lys Asp Gly Asp Glu Val Glu
                420                 425                 430

Asp Phe Val Glu Val His Leu Pro Asp Val His Glu Gln Val Ser Gly
            435                 440                 445

Val Glu Leu Gly Leu Pro Asn Trp Gly Lys Tyr Val Leu Met Ile Ala
450                 455                 460

Gly Ala Leu Ile Ala Leu Met Leu Ile Ile Phe Leu Met Thr Cys Cys
465                 470                 475                 480

Arg Arg Val Asn Arg Pro Glu Ser Thr Gln Ser Ser Leu Gly Glu Thr
                485                 490                 495

Gly Arg Asn Val Ser Val Thr Ser Gln Ser Gly Lys Val Ile Ser Ser
                500                 505                 510

Trp Glu Ser Tyr Lys Ser Gly Gly Glu Thr Arg Leu
                515                 520

<210> SEQ ID NO 7
<211> LENGTH: 450
<212> TYPE: PRT
<213> ORGANISM: Rabies virus

<400> SEQUENCE: 7

Met Asp Ala Asp Lys Ile Val Phe Lys Val Asn Asn Gln Val Val Ser
1               5                   10                  15

Leu Lys Pro Glu Ile Ile Val Asp Gln Tyr Glu Tyr Lys Tyr Pro Ala
                20                  25                  30

Ile Lys Asp Leu Lys Lys Pro Cys Ile Thr Leu Gly Lys Ala Pro Asp
            35                  40                  45

Leu Asn Lys Ala Tyr Lys Ser Val Leu Ser Gly Met Asn Ala Ala Lys
        50                  55                  60

Leu Asp Pro Asp Asp Val Cys Ser Tyr Leu Ala Ala Ala Met Gln Phe
65                  70                  75                  80

Phe Glu Gly Thr Cys Pro Glu Asp Trp Thr Ser Tyr Gly Ile Leu Ile
                85                  90                  95

Ala Arg Lys Gly Asp Lys Ile Thr Pro Asp Ser Leu Val Glu Ile Lys
                100                 105                 110

Arg Thr Asp Val Glu Gly Asn Trp Ala Leu Thr Gly Gly Met Glu Leu
            115                 120                 125

Thr Arg Asp Pro Thr Val Ser Glu His Ala Ser Leu Val Gly Leu Leu
        130                 135                 140

Leu Ser Leu Tyr Arg Leu Ser Lys Ile Ser Gly Gln Asn Thr Gly Asn
145                 150                 155                 160

Tyr Lys Thr Asn Ile Ala Asp Arg Ile Glu Gln Ile Phe Glu Thr Ala
                165                 170                 175

Pro Phe Val Lys Ile Val Glu His His Thr Leu Met Thr Thr His Lys
                180                 185                 190

Met Cys Ala Asn Trp Ser Thr Ile Pro Asn Phe Arg Phe Leu Ala Gly
            195                 200                 205

Thr Tyr Asp Met Phe Phe Ser Arg Ile Glu His Leu Tyr Ser Ala Ile
        210                 215                 220

Arg Val Gly Thr Val Val Thr Ala Tyr Glu Asp Cys Ser Gly Leu Val
225                 230                 235                 240

Ser Phe Thr Gly Phe Ile Lys Gln Ile Asn Leu Thr Ala Arg Glu Ala
                245                 250                 255

Ile Leu Tyr Phe Phe His Lys Asn Phe Glu Glu Glu Ile Arg Arg Met
```

```
                260                 265                 270
Phe Glu Pro Gly Gln Glu Thr Ala Val Pro His Ser Tyr Phe Ile His
        275                 280                 285
Phe Arg Ser Leu Gly Leu Ser Gly Lys Ser Pro Tyr Ser Ser Asn Ala
        290                 295                 300
Val Gly His Val Phe Asn Leu Ile His Phe Val Gly Cys Tyr Met Gly
305                 310                 315                 320
Gln Val Arg Ser Leu Asn Ala Thr Val Ile Ala Ala Cys Ala Pro His
                325                 330                 335
Glu Met Ser Val Leu Gly Gly Tyr Leu Gly Glu Glu Phe Phe Gly Lys
            340                 345                 350
Gly Thr Phe Glu Arg Arg Phe Phe Arg Asp Glu Lys Glu Leu Gln Glu
        355                 360                 365
Tyr Glu Ala Ala Glu Leu Thr Lys Thr Asp Val Ala Leu Ala Asp Asp
    370                 375                 380
Gly Thr Val Asn Ser Asp Asp Glu Asp Tyr Phe Ser Gly Glu Thr Arg
385                 390                 395                 400
Ser Pro Glu Ala Val Tyr Thr Arg Ile Met Met Asn Gly Gly Arg Leu
                405                 410                 415
Lys Arg Ser His Ile Arg Arg Tyr Val Ser Val Ser Ser Asn His Gln
                420                 425                 430
Ala Arg Pro Asn Ser Phe Ala Glu Phe Leu Asn Lys Thr Tyr Ser Ser
            435                 440                 445
Asp Ser
    450

<210> SEQ ID NO 8
<211> LENGTH: 297
<212> TYPE: PRT
<213> ORGANISM: Rabies virus

<400> SEQUENCE: 8

Met Ser Lys Ile Phe Val Asn Pro Ser Ala Ile Arg Ala Gly Leu Ala
1               5                   10                  15
Asp Leu Glu Met Ala Glu Glu Thr Val Asp Leu Ile Asn Arg Asn Ile
            20                  25                  30
Glu Asp Asn Gln Ala His Leu Gln Gly Glu Pro Ile Glu Val Asp Asn
        35                  40                  45
Leu Pro Glu Asp Met Arg Gln Phe His Leu Gly Asp Glu Lys Leu Ser
    50                  55                  60
Asn Leu Gly Glu Met Val Arg Val Gly Glu Gly Lys Tyr Arg Glu Asp
65                  70                  75                  80
Phe Gln Met Asp Glu Gly Glu Asp Pro Asn Leu Leu Phe Gln Ser Tyr
                85                  90                  95
Leu Asp Asn Val Gly Val Gln Ile Val Arg Gln Met Arg Ser Gly Glu
            100                 105                 110
Arg Phe Leu Lys Ile Trp Ser Gln Thr Val Glu Glu Ile Ile Ser Tyr
        115                 120                 125
Val Thr Val Asn Phe Pro Asn Pro Pro Gly Arg Ser Ser Glu Asp Lys
    130                 135                 140
Ser Thr Gln Thr Thr Gly Arg Glu Leu Lys Lys Glu Thr Thr Ser Thr
145                 150                 155                 160
Leu Ser Gln Arg Glu Ser Gln Pro Ser Lys Ala Gly Met Val Ala Gln
                165                 170                 175
```

```
Val Ala Ser Gly Pro Pro Ser Leu Glu Trp Ser Ala Thr Asn Glu Glu
            180                 185                 190

Asp Asp Leu Ser Val Glu Ala Glu Ile Ala His Gln Ile Ala Glu Ser
        195                 200                 205

Phe Ser Lys Lys Tyr Lys Phe Pro Ser Arg Ser Ser Gly Ile Phe Leu
    210                 215                 220

Tyr Asn Phe Glu Gln Leu Glu Met Asn Leu Asp Asp Ile Val Lys Glu
225                 230                 235                 240

Ala Lys Asn Val Pro Gly Val Thr Arg Leu Ala His Asp Gly Ser Lys
                245                 250                 255

Ile Pro Leu Arg Cys Val Leu Gly Trp Val Ala Leu Ala Asn Ser Lys
            260                 265                 270

Lys Phe Gln Leu Ile Val Glu Ala Asp Lys Leu Ser Lys Ile Met Gln
    275                 280                 285

Asp Asp Leu Asp Arg Tyr Thr Ser Cys
        290                 295
```

<210> SEQ ID NO 9
<211> LENGTH: 202
<212> TYPE: PRT
<213> ORGANISM: Rabies virus

<400> SEQUENCE: 9

```
Met Asn Phe Leu Cys Lys Ile Val Lys Asn Cys Arg Asp Glu Asp Thr
1               5                   10                  15

Gln Lys Pro Ser Pro Val Ser Ala Pro Pro Asp Gly Asp Asp Leu Trp
            20                  25                  30

Leu Pro Pro Pro Glu Tyr Val Pro Leu Lys Glu Leu Thr Ser Lys Lys
        35                  40                  45

Asn Met Arg Asn Phe Cys Ile Asn Gly Glu Val Lys Val Cys Ser Pro
    50                  55                  60

Asn Gly Tyr Ser Phe Arg Ile Leu Arg His Ile Leu Arg Ser Phe Asp
65                  70                  75                  80

Glu Ile Tyr Ser Gly Asn His Arg Met Ile Gly Leu Val Lys Val Val
                85                  90                  95

Ile Gly Leu Ala Leu Ser Gly Ala Pro Val Pro Glu Gly Met Asn Trp
            100                 105                 110

Val Tyr Lys Leu Arg Arg Thr Leu Ile Phe Gln Trp Ala Asp Ser Arg
        115                 120                 125

Gly Pro Leu Glu Gly Glu Glu Leu Glu His Ser Gln Glu Ile Thr Trp
    130                 135                 140

Asp Asp Asp Thr Glu Phe Val Gly Leu Gln Met Arg Val Ser Ala Arg
145                 150                 155                 160

Gln Cys His Ile Gln Gly Arg Ile Trp Cys Ile Asn Met Asn Ser Arg
                165                 170                 175

Ala Cys Gln Leu Trp Ser Asp Met Ser Leu Gln Thr Gln Arg Ser Glu
            180                 185                 190

Glu Asp Lys Asp Ser Ser Leu Leu Leu Glu
        195                 200
```

<210> SEQ ID NO 10
<211> LENGTH: 2127
<212> TYPE: PRT
<213> ORGANISM: Rabies virus

<400> SEQUENCE: 10

```
Met Leu Asp Pro Gly Glu Val Tyr Asp Asp Pro Ile Asp Pro Ile Glu
1               5                   10                  15

Ser Glu Ala Glu Pro Arg Gly Thr Pro Thr Val Pro Asn Ile Leu Arg
            20                  25                  30

Asn Ser Asp Tyr Asn Leu Asn Ser Pro Leu Ile Glu Asp Ser Ala Lys
        35                  40                  45

Leu Met Leu Glu Trp Leu Lys Thr Gly Asn Arg Pro Tyr Arg Met Thr
    50                  55                  60

Leu Thr Asp Asn Cys Ser Arg Ser Tyr Lys Val Leu Lys Asp Tyr Phe
65                  70                  75                  80

Lys Lys Val Asp Leu Gly Ser Leu Lys Val Gly Gly Thr Ala Ala Gln
                85                  90                  95

Ser Met Ile Ser Leu Trp Leu Tyr Gly Ala His Ser Glu Ser Asn Arg
            100                 105                 110

Ser Arg Arg Cys Ile Thr Asp Leu Ala His Phe Tyr Ser Lys Ser Ser
        115                 120                 125

Pro Ile Glu Lys Leu Leu Asn Cys Thr Leu Gly Asn Arg Gly Leu Arg
    130                 135                 140

Ile Pro Pro Glu Gly Val Leu Ser Cys Leu Glu Arg Val Asp Tyr Asp
145                 150                 155                 160

Lys Ala Phe Gly Arg Tyr Leu Ala Asn Thr Tyr Ser Ser Tyr Leu Phe
                165                 170                 175

Phe His Val Ile Thr Leu Tyr Met Asn Ala Leu Asp Trp Glu Glu
                180                 185                 190

Lys Thr Ile Leu Ala Leu Trp Lys Asp Leu Thr Ser Val Asp Thr Gly
            195                 200                 205

Lys Asp Leu Val Lys Phe Lys Asp Gln Ile Trp Gly Leu Leu Val Val
    210                 215                 220

Thr Lys Asp Phe Val Tyr Ser Gln Ser Ser Asn Cys Leu Phe Asp Arg
225                 230                 235                 240

Asn Tyr Thr Leu Met Leu Lys Asp Leu Phe Leu Ser Arg Phe Asn Ser
                245                 250                 255

Leu Met Ile Leu Leu Ser Pro Pro Glu Pro Arg Tyr Ser Asp Asp Leu
            260                 265                 270

Ile Ser Gln Leu Cys Gln Leu Tyr Ile Ala Gly Asp Gln Val Leu Ser
    275                 280                 285

Leu Cys Gly Asn Ser Gly Tyr Glu Val Ile Lys Ile Leu Glu Pro Tyr
        290                 295                 300

Val Val Asn Ser Leu Val Gln Arg Ala Glu Lys Phe Arg Pro Leu Ile
305                 310                 315                 320

His Ser Leu Gly Asp Phe Pro Met Phe Ile Lys Asp Lys Val Asn Gln
                325                 330                 335

Leu Glu Gly Thr Phe Gly Pro Ser Ala Lys Arg Phe Arg Val Leu
            340                 345                 350

Asp Gln Phe Asp Asn Ile His Asp Leu Val Phe Val Tyr Gly Cys Tyr
    355                 360                 365

Arg His Trp Gly His Pro Tyr Ile Asp Tyr Arg Lys Gly Leu Ser Lys
        370                 375                 380

Leu Tyr Asp Gln Val His Ile Lys Lys Val Ile Asp Lys Ser Tyr Gln
385                 390                 395                 400

Glu Cys Leu Ala Ser Asp Leu Ala Arg Arg Ile Leu Arg Trp Gly Phe
                405                 410                 415

Asp Lys Tyr Ser Lys Trp Tyr Leu Asp Ser Arg Phe Leu Ala Leu Asp
```

-continued

```
                420             425             430
His Pro Leu Ala Pro Tyr Ile Lys Thr Gln Thr Trp Pro Lys His
            435             440             445
Ile Val Asp Leu Val Gly Asp Thr Trp His Lys Leu Pro Ile Thr Gln
450             455             460
Ile Phe Glu Ile Pro Glu Ser Met Asp Pro Ser Glu Ile Leu Asp Asp
465             470             475             480
Lys Ser His Ser Phe Thr Arg Thr Arg Leu Ala Ser Trp Leu Ser Glu
            485             490             495
Asn Arg Gly Gly Pro Val Pro Ser Glu Lys Val Ile Ile Thr Ala Leu
            500             505             510
Ser Lys Pro Pro Val Asn Pro Arg Glu Phe Leu Lys Ser Ile Asp Leu
            515             520             525
Gly Gly Leu Pro Asp Asp Leu Ile Ile Gly Leu Arg Pro Lys Glu
            530             535             540
Arg Glu Leu Lys Ile Glu Gly Arg Phe Phe Ala Leu Met Ser Trp Asn
545             550             555             560
Leu Arg Leu Tyr Phe Val Ile Thr Glu Lys Leu Leu Ala Asn Tyr Ile
            565             570             575
Leu Pro Leu Phe Asp Ala Leu Thr Met Thr Asp Asn Leu Asn Lys Val
            580             585             590
Phe Lys Lys Leu Ile Asp Arg Val Thr Gly Gln Gly Leu Leu Asp Tyr
            595             600             605
Ser Arg Val Thr Tyr Ala Phe His Leu Asp Tyr Glu Lys Trp Asn Asn
            610             615             620
His Gln Arg Leu Glu Ser Thr Glu Asp Val Phe Ser Val Leu Asp Gln
625             630             635             640
Val Phe Gly Leu Lys Arg Val Phe Ser Arg Thr His Glu Phe Phe Gln
            645             650             655
Lys Ser Trp Ile Tyr Tyr Ser Asp Arg Ser Asp Leu Ile Gly Leu Arg
            660             665             670
Glu Asp Gln Ile Tyr Cys Leu Asp Met Ser Asn Gly Pro Thr Cys Trp
            675             680             685
Asn Gly Gln Asp Gly Gly Leu Glu Gly Leu Arg Gln Lys Gly Trp Ser
            690             695             700
Leu Val Ser Leu Leu Met Ile Asp Arg Glu Ser Gln Thr Arg Asn Thr
705             710             715             720
Arg Thr Lys Ile Leu Ala Gln Gly Asp Asn Gln Val Leu Cys Pro Thr
            725             730             735
Tyr Met Leu Ser Pro Gly Leu Ser Gln Glu Gly Leu Leu Tyr Glu Leu
            740             745             750
Glu Ser Ile Ser Arg Asn Ala Leu Ser Ile Tyr Arg Ala Ile Glu Glu
            755             760             765
Gly Ala Ser Lys Leu Gly Leu Ile Ile Lys Lys Glu Glu Thr Met Cys
            770             775             780
Ser Tyr Asp Phe Leu Ile Tyr Gly Lys Thr Pro Leu Phe Arg Gly Asn
785             790             795             800
Ile Leu Val Pro Glu Ser Lys Arg Trp Ala Arg Val Ser Cys Ile Ser
            805             810             815
Asn Asp Gln Ile Val Asn Leu Ala Asn Ile Met Ser Thr Val Ser Thr
            820             825             830
Asn Ala Leu Thr Val Ala Gln His Ser Gln Ser Leu Ile Lys Pro Met
            835             840             845
```

-continued

```
Arg Asp Phe Leu Leu Met Ser Val Gln Ala Val Phe His Tyr Leu Leu
850                 855                 860
Phe Ser Pro Ile Leu Lys Gly Arg Val Tyr Lys Ile Leu Ser Ala Glu
865                 870                 875                 880
Gly Glu Ser Phe Leu Leu Ala Met Ser Arg Ile Ile Tyr Leu Asp Pro
                    885                 890                 895
Ser Leu Gly Gly Val Ser Gly Met Ser Leu Gly Arg Phe His Ile Arg
                900                 905                 910
Gln Phe Ser Asp Pro Val Ser Glu Gly Leu Ser Phe Trp Arg Glu Ile
        915                 920                 925
Trp Leu Ser Ser His Glu Ser Trp Ile His Ala Leu Cys Gln Glu Ala
930                 935                 940
Gly Asn Pro Asp Leu Gly Glu Arg Thr Leu Glu Ser Phe Thr Arg Leu
945                 950                 955                 960
Leu Glu Asp Pro Thr Thr Leu Asn Ile Lys Gly Gly Ala Ser Pro Thr
                965                 970                 975
Ile Leu Leu Lys Asp Ala Ile Arg Lys Ala Leu Tyr Asp Glu Val Asp
                980                 985                 990
Lys Val Glu Asn Ser Glu Phe Arg  Glu Ala Ile Leu Leu  Ser Lys Thr
                995                 1000                 1005
His Arg  Asp Asn Phe Ile Leu  Phe Leu Lys Ser Val  Glu Pro Leu
    1010                 1015                 1020
Phe Pro  Arg Phe Leu Ser Glu  Leu Phe Ser Ser  Phe Leu Gly
    1025                 1030                 1035
Ile Pro  Glu Ser Ile Ile Gly  Leu Ile Gln Asn Ser  Arg Thr Ile
    1040                 1045                 1050
Arg Arg  Gln Phe Arg Lys Ser  Leu Ser Arg Thr Leu  Glu Glu Ser
    1055                 1060                 1065
Phe Tyr  Asn Ser Glu Ile His  Gly Ile Asn Arg Met  Thr Gln Thr
    1070                 1075                 1080
Pro Gln  Arg Val Gly Arg Val  Trp Pro Cys Ser Ser  Glu Arg Ala
    1085                 1090                 1095
Asp Leu  Leu Arg Glu Ile Ser  Trp Gly Arg Lys Val  Val Gly Thr
    1100                 1105                 1110
Thr Val  Pro His Pro Ser Glu  Met Leu Gly Leu Leu  Pro Lys Ser
    1115                 1120                 1125
Ser Ile  Ser Cys Thr Cys Gly  Ala Thr Gly Gly Gly  Asn Pro Arg
    1130                 1135                 1140
Val Ser  Val Ser Val Leu Pro  Ser Phe Asp Gln Ser  Phe Phe Ser
    1145                 1150                 1155
Arg Gly  Pro Leu Lys Gly Tyr  Leu Gly Ser Ser Thr  Ser Met Ser
    1160                 1165                 1170
Thr Gln  Leu Phe His Ala Trp  Glu Lys Val Thr Asn  Val His Val
    1175                 1180                 1185
Val Lys  Arg Ala Ile Ser Leu  Lys Glu Ser Ile Asn  Trp Phe Ile
    1190                 1195                 1200
Asn Arg  Asn Ser Asn Leu Ala  Gln Thr Leu Ile Arg  Asn Ile Met
    1205                 1210                 1215
Ser Leu  Thr Gly Pro Asp Phe  Pro Leu Glu Glu Ala  Pro Val Phe
    1220                 1225                 1230
Lys Arg  Thr Gly Ser Ala Leu  His Arg Phe Lys Ser  Ala Arg Tyr
    1235                 1240                 1245
```

-continued

```
Ser Glu Gly Gly Tyr Ser Ser Val Cys Pro Asn Leu Leu Ser His
    1250                1255                1260

Ile Ser Val Ser Thr Asp Thr Met Ser Asp Leu Thr Gln Asp Gly
    1265                1270                1275

Lys Asn Tyr Asp Phe Met Phe Gln Pro Leu Met Leu Tyr Ala Gln
    1280                1285                1290

Thr Trp Thr Ser Glu Leu Val Gln Arg Asp Thr Arg Leu Arg Asp
    1295                1300                1305

Ser Thr Phe His Trp His Leu Arg Cys Asn Arg Cys Val Arg Pro
    1310                1315                1320

Ile Glu Asp Ile Thr Leu Glu Thr Ser Gln Ile Phe Glu Phe Pro
    1325                1330                1335

Asp Val Ser Lys Arg Ile Ser Arg Met Val Ser Gly Ala Val Pro
    1340                1345                1350

His Phe Gln Lys Leu Pro Asp Ile Arg Leu Arg Pro Gly Asp Phe
    1355                1360                1365

Glu Ser Leu Ser Gly Arg Glu Lys Ser Arg His Ile Gly Ser Ala
    1370                1375                1380

Gln Gly Leu Leu Tyr Ser Ile Leu Val Ala Ile His Asp Ser Gly
    1385                1390                1395

Tyr Asn Asp Gly Thr Ile Phe Pro Val Asn Ile Tyr Gly Lys Val
    1400                1405                1410

Ser Pro Arg Asp Tyr Leu Arg Gly Leu Ala Arg Gly Ile Leu Ile
    1415                1420                1425

Gly Ser Ser Ile Cys Phe Leu Thr Arg Met Thr Asn Ile Asn Ile
    1430                1435                1440

Lys Arg Pro Leu Glu Leu Ile Ser Gly Val Ile Ser Tyr Ile Leu
    1445                1450                1455

Leu Arg Leu Asp Asn His Pro Ser Leu Tyr Ile Met Leu Arg Glu
    1460                1465                1470

Pro Ser Leu Arg Gly Glu Ile Phe Ser Ile Pro Gln Lys Ile Pro
    1475                1480                1485

Ala Ala Tyr Pro Thr Thr Met Lys Glu Gly Asn Arg Ser Ile Leu
    1490                1495                1500

Cys Tyr Leu Gln His Val Leu Arg Tyr Glu Arg Glu Val Ile Thr
    1505                1510                1515

Ala Ser Pro Glu Asn Asp Trp Leu Trp Ile Phe Ser Asp Phe Arg
    1520                1525                1530

Ser Ala Lys Met Thr Tyr Leu Thr Leu Ile Thr Tyr Gln Ser His
    1535                1540                1545

Leu Leu Leu Gln Arg Val Glu Arg Asn Leu Ser Lys Ser Met Arg
    1550                1555                1560

Ala Thr Leu Arg Gln Met Gly Ser Leu Met Arg Gln Val Leu Gly
    1565                1570                1575

Gly His Gly Glu Asp Thr Leu Glu Ser Asp Asp Ile Gln Arg
    1580                1585                1590

Leu Leu Lys Asp Ser Leu Arg Arg Thr Arg Trp Val Asp Gln Glu
    1595                1600                1605

Val Arg His Ala Ala Arg Thr Met Ser Gly Asp Tyr Ser Pro Asn
    1610                1615                1620

Lys Arg Val Ser Arg Lys Ala Gly Cys Ser Glu Trp Val Cys Ser
    1625                1630                1635

Ala Gln Gln Val Ala Val Ser Thr Ser Ala Asn Pro Ala Pro Val
```

-continued

```
                1640                1645                1650

Ser  Glu  Leu  Asp  Ile  Arg  Ala  Leu  Ser  Lys  Arg  Phe  Gln  Asn  Pro
     1655                1660                1665

Leu  Ile  Ser  Gly  Leu  Arg  Val  Val  Gln  Trp  Ala  Thr  Gly  Ala  His
     1670                1675                1680

Tyr  Lys  Leu  Lys  Pro  Ile  Leu  Asp  Asp  Leu  Asn  Val  Phe  Pro  Ser
     1685                1690                1695

Leu  Cys  Leu  Val  Val  Gly  Asp  Gly  Ser  Gly  Ile  Ser  Arg  Ala
     1700                1705                1710

Val  Leu  Asn  Met  Phe  Pro  Asp  Ser  Lys  Leu  Val  Phe  Asn  Ser  Leu
     1715                1720                1725

Leu  Glu  Val  Asn  Asp  Leu  Met  Ala  Ser  Gly  Thr  His  Pro  Leu  Pro
     1730                1735                1740

Pro  Ser  Ala  Ile  Met  Ser  Gly  Gly  Asp  Asp  Ile  Ile  Ser  Arg  Val
     1745                1750                1755

Ile  Asp  Phe  Asp  Ser  Ile  Trp  Glu  Lys  Pro  Ser  Asp  Leu  Arg  Asn
     1760                1765                1770

Leu  Ala  Thr  Trp  Arg  Tyr  Phe  Gln  Ser  Val  Gln  Lys  Gln  Val  Asn
     1775                1780                1785

Met  Ser  Tyr  Asp  Leu  Ile  Val  Cys  Asp  Ala  Glu  Val  Thr  Asp  Ile
     1790                1795                1800

Ala  Ser  Ile  Asn  Arg  Ile  Thr  Leu  Leu  Met  Ser  Asp  Phe  Ala  Leu
     1805                1810                1815

Ser  Ile  Asp  Gly  Pro  Leu  Tyr  Leu  Val  Phe  Lys  Thr  Tyr  Gly  Thr
     1820                1825                1830

Met  Leu  Val  Asn  Pro  Asp  Tyr  Lys  Ala  Ile  Gln  His  Leu  Ser  Arg
     1835                1840                1845

Ala  Phe  Pro  Ser  Val  Thr  Gly  Phe  Ile  Thr  Gln  Val  Thr  Ser  Ser
     1850                1855                1860

Phe  Ser  Ser  Glu  Leu  Tyr  Leu  Arg  Phe  Ser  Lys  Arg  Gly  Lys  Phe
     1865                1870                1875

Phe  Arg  Asp  Ala  Glu  Tyr  Leu  Thr  Ser  Ser  Thr  Leu  Arg  Glu  Met
     1880                1885                1890

Ser  Leu  Val  Leu  Phe  Asn  Cys  Ser  Ser  Pro  Lys  Ser  Glu  Met  Gln
     1895                1900                1905

Arg  Ala  Arg  Ser  Leu  Asn  Tyr  Gln  Asp  Leu  Val  Arg  Gly  Phe  Pro
     1910                1915                1920

Glu  Glu  Ile  Ile  Ser  Asn  Pro  Tyr  Asn  Glu  Met  Ile  Ile  Thr  Leu
     1925                1930                1935

Ile  Asp  Ser  Asp  Val  Glu  Ser  Phe  Leu  Val  His  Lys  Met  Val  Asp
     1940                1945                1950

Asp  Leu  Glu  Leu  Gln  Arg  Gly  Thr  Leu  Ser  Lys  Val  Ala  Ile  Ile
     1955                1960                1965

Ile  Ser  Ile  Met  Ile  Val  Phe  Ser  Asn  Arg  Val  Phe  Asn  Ile  Ser
     1970                1975                1980

Lys  Pro  Leu  Thr  Asp  Pro  Leu  Phe  Tyr  Pro  Pro  Ser  Asp  Pro  Lys
     1985                1990                1995

Ile  Leu  Arg  His  Phe  Asn  Ile  Cys  Cys  Ser  Thr  Met  Met  Tyr  Leu
     2000                2005                2010

Ser  Thr  Ala  Leu  Gly  Asp  Val  Pro  Ser  Phe  Ala  Arg  Leu  His  Asp
     2015                2020                2025

Leu  Tyr  Asn  Arg  Pro  Ile  Thr  Tyr  Tyr  Phe  Arg  Lys  Gln  Val  Ile
     2030                2035                2040
```

```
Arg Gly Asn Ile Tyr Leu Ser Trp Ser Trp Ser Asp Asp Thr Pro
    2045              2050                2055

Val Phe Lys Arg Val Ala Cys Asn Ser Ser Leu Ser Leu Ser Ser
    2060              2065                2070

His Trp Ile Arg Leu Ile Tyr Lys Ile Val Lys Thr Thr Arg Leu
    2075              2080                2085

Val Gly Ser Ile Glu Asp Leu Ser Gly Glu Val Glu Arg His Leu
    2090              2095                2100

His Gly Tyr Asn Arg Trp Ile Thr Leu Glu Asp Ile Arg Ser Arg
    2105              2110                2115

Ser Ser Leu Leu Asp Tyr Ser Cys Leu
    2120              2125

<210> SEQ ID NO 11
<211> LENGTH: 1575
<212> TYPE: RNA
<213> ORGANISM: Rabies virus

<400> SEQUENCE: 11
```

| | | | | | |
|---|---|---|---|---|---|
| augguuccuc | aggcucuccu | guuuguaccc | cuucugguuu | uuccauugug | uuuugggaaa | 60 |
| uucccuauuu | acacgauacc | agacaagcuu | gguccccugga | gcccgauuga | cauacaucac | 120 |
| cucagcugcc | caaacaauuu | gguaguggag | gacgaaggau | gcaccaaccu | gucagggouc | 180 |
| uccuacaugg | aacuuaaagu | uggauacauc | ucagccauaa | aaaugaacgg | guucacuugc | 240 |
| acaggcguug | ugacggaggc | ugaaaccuac | acuaacuucg | uggguuaugu | cacaaccacg | 300 |
| uucaaaagaa | agcauuuccg | cccaacacca | gaugcaugua | gagccgcgua | caacuggaag | 360 |
| auggccggug | accccagaua | ugaagagucu | cuacacaauc | cguacccuga | cuaccacugg | 420 |
| cuucgaacug | uaaaaaccac | caaggagucu | cucguuauca | uaucuccaag | ugguggcagau | 480 |
| uuggacccau | augacagauc | ccuucacucg | agggucuucc | cuggcgggaa | uugcucagga | 540 |
| guagcggugu | cuucuaccua | cugcuccacu | aaccacgauu | acaccauuug | gaugcccgag | 600 |
| aauccgagac | uagggauguc | uugugacauu | uuuaccaaua | guagagggaa | gagagcaucc | 660 |
| aaagggagug | agacuugcgg | cuuuguagau | gaaagaggcc | uauauaaguc | uuuaaaagga | 720 |
| gcaugcaaac | ucaaguuaug | uggaguucua | ggacuuagac | uuauggaugg | aacauggggu | 780 |
| gcgaugcaaa | caucaaauga | aaccaaaugg | ugcccucccg | gucaguuggu | gaauuugcac | 840 |
| gacuuucgcu | cagacgaaau | ugagcaccuu | guguagagg | aguuggucaa | gaagagagag | 900 |
| gaguguccugg | augcacuaga | guccaucaug | accaccaagu | cagugaguuu | cagacgucuc | 960 |
| agucauuuaa | gaaacuuagu | cccugggouu | ggaaaagcau | auaccauauu | caacaagacc | 1020 |
| uugauggaag | ccgaugcuca | cuacaaguca | gucagaacuu | ggaaugagau | caucccuuca | 1080 |
| aaaggugguu | uaagaguugg | ggggaggugu | cauccucaug | uaaacggggu | auuuucaau | 1140 |
| gguauaauau | uaggaccuga | cgcaaugcuc | uuaauccccag | agaugcaauc | aucccuccuc | 1200 |
| cagcaacauu | uggaguuguu | gguauccucg | guuaucccc | uuaugcaccc | ccuggcagac | 1260 |
| ccgucuaccg | uuucaagaa | cgguggacgag | gcugaggauu | uguuggaagu | ucaccuuccc | 1320 |
| gaugugcacg | aacggaucuc | aggaguugac | uugggcuccc | cgaacugggg | gaaguaugua | 1380 |
| uuacugagug | cagggggccou | gacugccuug | auguugauaa | uuuuccugau | gacaugcugg | 1440 |
| agaagaguca | aucgaucgga | accuacacaa | cacaaucuca | gagggacagg | gagggaggug | 1500 |
| ucaggucacuc | cccaaagcgg | gaagaucaua | ucuucauggg | aaucauacaa | gagcgggggu | 1560 |

|  |  |
|---|---:|
| gagaccggac uguga | 1575 |

<210> SEQ ID NO 12
<211> LENGTH: 1353
<212> TYPE: RNA
<213> ORGANISM: Rabies virus

<400> SEQUENCE: 12

|  |  |
|---|---:|
| auggaugccg acaagauugu auucaaaguc aauaaucagg uggucucuuu gaagccugag | 60 |
| auuaucgugg aucaauauga guacaaguac ccugccauca aagauuugaa aaagcccugu | 120 |
| auaacucuag gaaaggcucc cgauuuaaau aaagcauaca agucaguuuu aucaugcaug | 180 |
| agcgccgcca aacuugaucc ugacgaugua guuccuauu uggcggcggc aaugcaguuu | 240 |
| uuugagggga cauguccgga agacuggacc agcuauggaa ucgugauugc acgaaaagga | 300 |
| gauaagauca ccccagguuc ucugguggag auaaaacgua cugauguaga agggaauugg | 360 |
| gcucugacag gaggcaugga acugacaaga gaccccacug ucccugagca ugcguccuua | 420 |
| gucggucuuc ucuugagucu guauagguug agcaaaauau ccgggcaaag cacugguaac | 480 |
| uauaagacaa acauugcaga caggauagag cagauuuuug agacagcccc uuuuguuaaa | 540 |
| aucgugaac accauacucu aaugacaacu cacaaaaugu gugcuaauug gaguacuaua | 600 |
| ccaaacuuca gauuuuuggc cggaaccuau gacauguuuu ucccggau ugagcaucua | 660 |
| uauucagcaa ucagaguggg cacaguuguc acugcuuaug aagacuguuc aggacuggug | 720 |
| ucauuuacug gguucauaaa acaaaucaau cucaccgcua gagaggcaau acuauauuuc | 780 |
| uuccacaaga acuuugagga agagauaaga agaauguuug agccagggca ggagacagcu | 840 |
| guuccucacu cuuauuucau ccacuuccgu ucacuaggcu ugaguggaa aucuccuuau | 900 |
| ucaucaaaug cuguuggca cguguucaau ucauucacu uguaggaug cuauauggggu | 960 |
| caagucagau cccuaaaugc aacgguuauu gcugcaugug cuccucauga aaugucuguu | 1020 |
| cuaggggcu aucugggaga ggaauucuuc gggaaaggga cauuugaaag aagauucuuc | 1080 |
| agagaugaga aagaacuuca gaaauacgag gcggcugaac ugacaaagac ugacguagca | 1140 |
| cuggcagaug auggaacugu caacucugac gacgaggacu acuucucagg ugaaaccaga | 1200 |
| aguccggaag cuguuuauac ucgaaucaua augaauggag ucgacugaa gagaucgcac | 1260 |
| auacggagau augucucagu caguccaauu caucaagcuc guccaaacuc auucgccgag | 1320 |
| uuucuaaaca agacauauuc gagugacuca uaa | 1353 |

<210> SEQ ID NO 13
<211> LENGTH: 894
<212> TYPE: RNA
<213> ORGANISM: Rabies virus

<400> SEQUENCE: 13

|  |  |
|---|---:|
| augagcaaga cuuugucaa uccuagugcu auuagagccg gucuggccga ucuugagaug | 60 |
| gcugaagaaa cuguugaucu gaucaauaga aauaucgaag acaaucaggc ucaucuccaa | 120 |
| gggaaccca uagaagugga caaucucccu gaggauaugg ggcgacuuca ccuggaugau | 180 |
| ggaaaaucgc ccaacccugg ugagauggcc aaggugggaa aagcaaguaa ucgagaggac | 240 |
| uuucagaugg augaaggaga ggauccuagc cuccuguucc agcauaccu ggacaauguu | 300 |
| ggaguccaaa uagucagaca aauaagguca ggagagagau uucucaagau augguacag | 360 |
| accguagaag agauuauauc cuaugucgcg gucaacuuc ccaaccccuc aggaaagucu | 420 |
| ucagaggaua aaucaacccca gacuaccggc cgagagcuca agaaggagac aacacccacu | 480 |

```
ccuucucaga gagaaagcca auccucgaaa gccaggaugg cggcucaaac ugcuucuggc      540
ccuccagccc uugaaugguc ggccaccaau gaagaggaug aucuaucagu ggaggcugag      600
aucgcucacc agauugcaga aaguuucucc aaaaaauaua aguuucccuc ucgauccuca      660
gggauacucu uguauaauuu ugagcaauug aaaaugaacc uugaugauau aguuaaagag      720
gcaaaaaaug uaccaggugu gacccguuua gcccgugacg gguccaaacu ccccuaaga       780 uguuacugg gauggucgc cuggccaac ucuaagaaau ccaguuguu agucgaaucc          840 aacaagcuga guaaaaucau gcaagaugac uugaaucgcu auacaucuug cuaa            894

<210> SEQ ID NO 14
<211> LENGTH: 609
<212> TYPE: RNA
<213> ORGANISM: Rabies virus

<400> SEQUENCE: 14
augaacuuuc uacguaagau agugaaaaau ugcagggacg aggacacuca aaaacccucu       60
cccgugucag cccccucugga ugacgaugac uuguggcuuc acccccuga auacgucccg      120 cuaaaagaac uuacaagcaa gaagaacagg aggaacuuuu guaucaacgg aggggguuaaa    180 gguguagcc cgaaugguua cucguucggg auccugcggc acauucugag aucauucgac      240
gagauauauu cugggaauca uaggauggue ggguuaguca aguaguauu uggacuggcu      300 uugucaggag cuccaguccc ugagggcaug aacuggguau acaaguugag gagaacccuu     360
aucuuccagu gggcugauuc caggggcccu cuugaagggg aggaguugga auacucucag     420
gagaucacuu gggaugauaa uacgagguuc gucggauugc aaauaagagu gagugcaaaa     480 caguguacaua uccggggcag aaucggugu aucaacauga acucgagagc aggucaacua     540
uggucugaca ugucucuuca gacacaaagg uccgaagagg acaaagauuc cucucugcuu     600
cuagaauaa                                                             609

<210> SEQ ID NO 15
<211> LENGTH: 6429
<212> TYPE: RNA
<213> ORGANISM: Rabies virus

<400> SEQUENCE: 15
augcucgauc cuggagaggu cuaugaugac ccuauugacc caaucgaguu agaggcugaa       60
cccagaggaa cccccacugu ccccaacauc uugaggaacu cugacuacaa ucucaacucu      120
ccuuugauag aagauccugc uagcuaaug uuagaauggu aaaaacagg gaauagaccu        180 uaucggauga cucuaacaga caauugcucc aggucuuuca gaguuugaa agauuauuuc       240 aagaagguag auugggguuc ccucaaggug ggcggaaugg cugcacaguc aaugauuucu      300
cucugguuau auggugccca cucugaaucc aacaggagcc ggagauguau aacagacuug      360
gcccauuucu auuccaaguc gucccccaua gagaagcugu aaaucucac gcuaggaaau      420 agagggcuga gaauccccc agagggagug uuaaguugcc uugagagggu ugauuaugau     480
aaugcauuug gaagguaucu ugccaacacg uauuccucuu acuguucuu ccauguaauc       540 accuuauaca ugaacgcccu agacugggau gaagaaaaga ccauccuagc auuauggaaa     600
gauuuaaccu caguggacau cggaaggac uugguaaagu caaagaccaa aauaugggga     660
cugcugaucg ugcaaaagga cuuuguuuac ucccaaaguu ccaauugucu uuugacaga      720 aacuacacac uuaugcuaaa agaucuuuuc uugcucgcu ucaacuccuu aauggucuua      780
```

| | |
|---|---|
| cuuucucccc cagagcsccg auacucagau gacuugauau cucagcuaug ccagcuguac | 840 |
| auugcugggg aucaagucuu gucuaugugu ggaaacuccg gcuaugaagu caucaaaaua | 900 |
| uuggagccau augucgugaa uaguuuaguc cagagagcag aaaaguuuag gccucucauu | 960 |
| cauuccuugg gagacuuucc uguauuuaua aaagacaagg uaagucaacu cgaagagacg | 1020 |
| uucgguuccu gugcaagaag guucuuuagg gcucuggauc aauucgacaa cauacaugac | 1080 |
| uugguuuuug uguauggcug uuacaggcau uggggggcacc cauauauga uuaucgaaag | 1140 |
| ggucugucaa aacuauauga ucagguucac auuaaaaaag ugauagauaa guccuaccag | 1200 |
| gagugcuuag caagcgaccu agccaggagg auccuuagau gggguuuuga uaaguacucc | 1260 |
| aagugguauc uggauucacg auuccuagcc cgagaccacc ccuugacucc uuauaucaaa | 1320 |
| acccaaacau ggccacccaa acauauugua gauuuggugg gggauacaug gcacaagcuc | 1380 |
| ccgaucacgc aaaucuuuga gauuccugaa ucaauggauc caucagaaau auuggaugac | 1440 |
| aaaucacauu cuuucaccag aacgagacua gcuucuuggc ugucagaaaa ccgagggggg | 1500 |
| ccuguuccua gcgaaaaagu uauuaucacg gcccugucua agccgccugu caaucccga | 1560 |
| gaguuucuga agucuauaga ccucggagga uugccagaug aagacuugau aauuggccuc | 1620 |
| aagccaaagg aacgggaauu gaagauugaa ggucgauucu uugcucuaau gcaguggaau | 1680 |
| cuaagauugu auuuugucau cacugaaaaa cucuuggcca acuacaucuu gccacuuuuu | 1740 |
| gacgcgcuga cuaugacaga caaccugaac aaggugguuua aaaagcugau cgacaggguc | 1800 |
| accgggcaag ggcuucugga cuauucaagg gucacauaug cauuucaccu ggacuaugaa | 1860 |
| aagugggaaca accaucaaag auuagaguca acagaggaug uauuuucugu ccuagaucaa | 1920 |
| guguuuggau ugaagagagu guuuucuaga acacgagu uuuucagaa guccuggauc | 1980 |
| uauuauucag acagaucaga ccucaucggg uuacgggagu aucaaauaua cugcuuagau | 2040 |
| gcguccaacg gcccaaccug uuggaauggc caggauggcg ggcuagaagg cuuacggcag | 2100 |
| aagggcugga gucuagucag cuuauugaug auagauagag aaucucaaau caggaacaca | 2160 |
| agaaccaaag uacuagcuca aggagacaac cagguuuuau guccgacaua uauguugucg | 2220 |
| ccagggcuau cucaagaggg gcccucuau gaauuggaga gcauaucaag gaaugcauuu | 2280 |
| ucgauauaca gagccgucga ggaaggggca ucuaaacuag ggcugaucau caagaaagaa | 2340 |
| gagaccaugu guaguuauga cuccucaau uauggaaaaa ccccuuguguu uagagguaac | 2400 |
| auauuggugc cugaguccaa aagaugggcc agagucucuu gcgucucuaa ugaccaaaua | 2460 |
| gucaaccucg ccaauauaau gucgacagug uccaccaacg cgcuaacagu ggcacaacac | 2520 |
| ucucaaucuu ugaucaaacc gaugagggau uuucugcuca gucaguaca ggcagucuuu | 2580 |
| cacuaccugc uauuuagccc aaucuuaaag ggaagaguuu acaagauucu gagcgcugaa | 2640 |
| ggggagagcu uucuccuagc caugucaagg auaaucuauc uagauccuuc uuugggaggg | 2700 |
| guaucuggaa ugucccucgg aagauuccau auacgacagu ucucagaccc ugucucugaa | 2760 |
| ggguuauccu ucuggagaga gaucgguuua agcccacg aguccggau ucacgcguug | 2820 |
| ugcaagagg cuggaaaccc agaucuugga gagagaacac ucgagagcuu cacucgccuu | 2880 |
| cuagaagauc cuaccaccuu aaauaucaga ggaggggcca guccuaccau ucuacucaag | 2940 |
| gaugcaauca gaaaggcuuu auaugacgag guggacaagg uggagaacuc agaguuucga | 3000 |
| gaggcaaucc uguugccaa gacccauaga gauaauuuua uacucuucu aacaucuguu | 3060 |
| gagccucugu uccucgauu ucucagagag cuauucaguu cgucuuuuu gggaaucccc | 3120 |
| gagucaauca uuggacugau acaaaacucc cgaacgauaa gaaggcaguu uagaaagagu | 3180 |

```
cucucaaaaa cuuuagaaga auccuucuac aacucagaga uccacgggau uagucggaug    3240
acccagacac cucagagggu uggggggug uggccuugcu cuucagagag ggcagaucua     3300 cuuaggggaga ucucuugggg aagaaaagug guaggcacga caguuccuca cccuucugag   3360
auguuggggu uacuucccaa guccucuauu ucuugcacuu guggagcaac aggaggaggc    3420
aauccuagag uuucuguauc aguacucccg ucuuugauc agucauuuuu uugcacgggg    3480 cccccuaaagg gguacuuggg cucguccacc ucuaugucga cccagcuauu ccaugcaugg   3540
gaaaaaguca cuaauguuca uguggugaag agagcucuau cguuaaaaga aucuauaaac    3600
ugguucauua cuagagauuc caacuuggcu caaacucuaa uuaggaacau ugugucucug    3660
acaggcccug auucccucu agaggaggcc ccuguuuuca aaaggacggg gucagccuug     3720
cauagguuca agucugccag auacagcgaa ggaggguauu cuucuguaug cccgaaccuc    3780
cucucucaua uuucuguuag acagacacc augucugauu ugacccaaga cgggaagaac     3840
uacgauuuca uguccagcc auugaugcuu uaugcacaga cauggacauc agagcuggua    3900
cagagagaca caaggcuaag agacucuacg uuucauuggc accuccaaug caacaggugu    3960
gugagaccca uugacgacgu gacccuggag acccucucaga ucuucgaguu ccggaugug   4020 ucgaaaagaa uauccagaau gguuucuggg gcugugccuc acuuccagag gcuucccgau   4080
auccgucuga gaccaggaga uuugaaucu cuaagcggua gagaaaaguc ucaccauauc    4140
ggaucagcuc agggcucuuu auacucaauc uuaguggcaa uucacgacuc aggauacaau   4200
gauggaacca ucuucccugu caacauauac ggcaagguuu ccccuagaga cuauuugaga   4260
gggcucgcaa ggggaguauu gauaggaucc ucgauuugcu ucuugacgag aaugacaaau    4320
aucaauauua auagaccucu gaauugauc ucaggggguaa ucuauauau ucuccugagg    4380 cuagauaacc aucccuccuu guacauaaug ucagagaaac cgucuuuuag agaagagaua    4440 uuuucuauc cucagaaaau ccccgccgcu uauccaacca cuaugaaaga aggcaacaga    4500
ucaaucuugu guuaucucca acaugugcua cgcuaugagc gagagguaau cacggcgucu    4560
ccagagaaug acuggcuaug gaucuuuuca gacuuuagaa gugccaaaau gacgaaccua    4620
acccucauua cuuccaguc ucaucuucua uccagagggg uugagagaaa ccuaucuaag    4680
aguaugagag auaaccugcg acaauugagu uccuugauga ggcaggugcu gggcgggcac   4740
ggagaagaua ccuuagaguc agacgacaac auucaacgac uacuaaaaga ucuuuuacga   4800
aggacaagau ggguggauca agaggugcgc caugcagcua gaaccaugac uggagauuac   4860
agccccaaca gaaggugguc ccguaaggua ggauguucag aaugggucug cucugcuaa    4920 cagguugcag ucucuaccuc agcaaacccg gccccugucu cggagcuuga cauaagggcc   4980
cucucuaaga gguuccagaa cccuuugauc ucgggcuuga gaguguuuca gugggcaacc   5040
ggugcucauu auaagcuuaa gccauucuua gaugaucuca auguuuccc aucucucugc    5100 cuuguaguu gggacgggguc agggggggaua ucaaggcag uccucaacau guuuccagau   5160
gccaagcuug uguucaacag ucuuuuagag gugaaugacc ugauggcuuc cggaacacau    5220
ccacugccuc cuucagcaau caugagggga ggaaaugaua ucgucuccag agugauagau    5280
uuugacucaa ucugggaaaa accgccgac uugagaaaacu uggcuaccug gaaauacuuc    5340 cagucaguccc aaaagcaggu caacaugucc uaugaccuca uuauugcga ugcagaaguu    5400 acugacauug caucuaucaa ccggauaacc cguuaauugu ccgauuuugc auugucuaua    5460
gauggaccac ucuauuuggu cuucaaaacu uaugggacua ugcuaguaaa uccaaacuac    5520
```

| | |
|---|---|
| aaggcuauuc aacaccuguc aagagcguuc cccucgguca caggguuuau cacccaagua | 5580 |
| acuucgucuu uuucaucuga gcucuaccuu cgauucucca aacgagggaa guuuuucaga | 5640 |
| gaugcugagu acuugaccuc uuccacccuu cgagaaauga gccuugucuu auucaauugu | 5700 |
| agcagcccca agagugagau gcagagagcu cguuccuuga acuaucagga ucuugugaga | 5760 |
| ggauuuccug aagaaaucau aucaaauccu acaaugaga ugaucauaac ucugauugac | 5820 |
| agugauguag aaucuuuucu aguccacaag augguggaug aucuugaguu acagagggga | 5880 |
| acucugucua aaguggcuau cauuauagcc aucaugauag uuuucuccaa cagagucuuc | 5940 |
| aacguuucca aaccccuaac ugaccccuug uucuauccac cgucugaucc caaaauccug | 6000 |
| aggcacuuca acauauguug caguacuaug auguaucuau cuacugcuuu aggugacguc | 6060 |
| ccuagcuucg caagacuuca cgaccuguau aacagaccua uaacuuauua cuucagaaag | 6120 |
| caagucauuc uagggaacgu uuaucuaucu uggaguuggu ccaacgacac cucaguguuc | 6180 |
| aaaaggguag ccuguaauuc uagccugagu cugucaucuc acuggaucag guugauuuac | 6240 |
| aagauaguga agacuaccag acucguuggc agcaucaagg aucuauccgg agaaguggaa | 6300 |
| agacaccuuc auagguacaa caggugagau cccuagagag auaucagauc uagaucaucc | 6360 |
| cuacuagacu acaguugccu gugcaucgga uacuccugga agccugccca ugcuaagacu | 6420 |
| cuuguguga | 6429 |

```
<210> SEQ ID NO 16
<211> LENGTH: 42
<212> TYPE: DNA
<213> ORGANISM: Artificial Sequence
<220> FEATURE:
<223> OTHER INFORMATION: 5'-UTR of human ribosomal protein Large 32
      lacking the 5' terminal oligopyrimidine tract

<400> SEQUENCE: 16
```

| | |
|---|---|
| ggcgctgcct acggaggtgg cagccatctc cttctcggca tc | 42 |

```
<210> SEQ ID NO 17
<211> LENGTH: 186
<212> TYPE: DNA
<213> ORGANISM: Homo sapiens

<400> SEQUENCE: 17
```

| | |
|---|---|
| catcacattt aaaagcatct cagcctacca tgagaataag agaaagaaaa tgaagatcaa | 60 |
| aagcttattc atctgttttt cttttcgtt ggtgtaaagc caacaccctg tctaaaaaac | 120 |
| ataaatttct ttaatcattt tgcctctttt ctctgtgctt caattaataa aaaatggaaa | 180 |
| gaatct | 186 |

```
<210> SEQ ID NO 18
<211> LENGTH: 186
<212> TYPE: DNA
<213> ORGANISM: Homo sapiens

<400> SEQUENCE: 18
```

| | |
|---|---|
| catcacattt aaaagcatct cagcctacca tgagaataag agaaagaaaa tgaagatcaa | 60 |
| tagcttattc atctcttttt cttttcgtt ggtgtaaagc caacaccctg tctaaaaaac | 120 |
| ataaatttct ttaatcattt tgcctctttt ctctgtgctt caattaataa aaaatggaaa | 180 |
| gaacct | 186 |

```
<210> SEQ ID NO 19
```

```
<211> LENGTH: 110
<212> TYPE: DNA
<213> ORGANISM: Homo sapiens

<400> SEQUENCE: 19
gctggagcct cggtggccat gcttcttgcc ccttgggcct cccccagcc cctcctcccc      60 ttcctgcacc cgtaccccg tggtctttga ataaagtctg agtgggcggc                110

<210> SEQ ID NO 20
<211> LENGTH: 108
<212> TYPE: DNA
<213> ORGANISM: Homo sapiens

<400> SEQUENCE: 20
gctggagcct cggtagccgt tcctcctgcc cgctgggcct cccaacgggc cctcctcccc      60
tccttgcacc ggcccttcct ggtctttgaa taaagtctga gtgggcag                 108

<210> SEQ ID NO 21
<211> LENGTH: 132
<212> TYPE: DNA
<213> ORGANISM: Homo sapiens

<400> SEQUENCE: 21
gctcgctttc ttgctgtcca atttctatta aaggttcctt tgttccctaa gtccaactac      60
taaactgggg gatattatga agggccttga gcatctggat tctgcctaat aaaaaacatt    120
tattttcatt gc                                                        132

<210> SEQ ID NO 22
<211> LENGTH: 44
<212> TYPE: DNA
<213> ORGANISM: Artificial Sequence
<220> FEATURE:
<223> OTHER INFORMATION: Center, alpha-complex-binding portion of the
      3'UTR of an alpha-globin gene (muag)

<400> SEQUENCE: 22
gcccgatggg cctcccaacg ggccctcctc ccctccttgc accg                       44

<210> SEQ ID NO 23
<211> LENGTH: 24
<212> TYPE: DNA
<213> ORGANISM: Artificial Sequence
<220> FEATURE:
<223> OTHER INFORMATION: particular preferred histone stem-loop sequence

<400> SEQUENCE: 23
caaaggctct tttcagagcc acca                                             24

<210> SEQ ID NO 24
<211> LENGTH: 1792
<212> TYPE: RNA
<213> ORGANISM: Artificial Sequence
<220> FEATURE:
<223> OTHER INFORMATION: RAV-G(GC)-muag-A64-C30-histoneSL

<400> SEQUENCE: 24
gggagaaagc uuaccauggu gccccaggcc cugcucuucg uccgcgcu gguguucccc       60 cucugcuucg gcaaguuccc caucuacacc auccccgaca gcugggggcc guggagcccc    120
aucgacaucc accaccuguc cugcccaac aaccucgugg ucgaggacga gggcugcacc    180
aaccugagcg gguucuccua caugagcugc aagguggcu acaucagcgc caucaagaug    240
```

```
aacggguuca cgugcaccgg cguggucacc gaggcggaga ccuacacgaa cuucgugggc      300
uacgugacca ccaccuucaa gcggaagcac uuccgcccca cgccggacgc cugccgggcc      360
gccuacaacu ggaagauggc cggggacccc cgcuacgagg aguccuucca caaccccuac      420
cccgacuacc acuggcugcg gaccgucaag accaccaagg agagccuggu gaucaucucc      480
ccgagcgugg cggaccucga ccccuacgac cgcucccugc acagccgggu cuuccccggc      540
gggaacugcu ccggcguggc cgugagcucc acguacugca gccaaccca cgacuacacc       600 aucuggaugc ccgagaaccc gcgccugggg auguccugcg acaucuucac caacagccgg      660
ggcaagcgcg ccuccaaggg cagcgagacg ugcggguucg ucgacgagcg gggccucuac      720
aagucccuga aggggccug caagcugaag cucucgcggc ugcugggccu cgccucaug       780 gacgggaccu ggguggcgau gcagaccagc aacgagacca aguggugccc ccccggccag      840
cuggucaacc ugcacgacuu ccggagcgac gagaucgagc accucguggu ggaggagcug      900
gucaagaagc gcgaggagug ccuggacgcc cucgagucca ucaugacgac caagagcgug      960
uccuuccggc gccugagcca ccugcggaag cucgugcccg gguucggcaa ggccuacacc     1020
aucuucaaca gacccugau ggaggccgac gcccacuaca aguccguccg cacguggaac      1080
gagaucaucc cgagcaaggg gugccugcgg gguggcggcc gcugccaccc ccacgucaac     1140 ggggguguucu caacggcau caucucggg cccgacggca acgugcugau ccccgagaug      1200 cagucccagcc ugcuccagca gcacauggag cugcuggucu ccagcugau cccgcucaug     1260 caccccccugg cggacccucc caccguguuc aagaacgggg acgaggccga ggacuucguc     1320
gaggugcacc ugcccgacgu gcacgagcgg aucagcggcg ucgaccucgg ccugccgaac     1380 uggggggaagu acgugcugcu cuccgccggc gcccugaccg cccugaugcu gaucaucuuc     1440
cucaugaccu gcuggcgccg ggugaaccgg agcgagccca cgcagcacaa ccugcgcggg     1500
accggccggg aggucuccgu gaccccgcag agcgggaaga ucaucuccag cugggagucc     1560
uacaagagcg gcgcgagac cgggcuguga ggacuaguua uaagacugac ugcccgaug      1620 ggccucccaa cgggccucuc uccccuccuu gcaccgagau uaauaaaaaa aaaaaaaaaa     1680
aaaaaaaaaa aaaaaaaaaa aaaaaaaaaa aaaaaaaaa aaaaaaaug cauccccccc     1740 cccccccccc ccccccccc cccaaaggc ucuuucaga gccaccagaa uu              1792
```

<210> SEQ ID NO 25
<211> LENGTH: 1957
<212> TYPE: RNA
<213> ORGANISM: Artificial Sequence
<220> FEATURE:
<223> OTHER INFORMATION: 32L-RAV-G(GC)-albumin7-A64-C30-histoneSL

<400> SEQUENCE: 25

```
ggggcgcugc cuacggaggu ggcagccauc uccuucucgg caucaagcuu accaugguge      60 cccaggcccu gcucuucguc ccgcugcugg uguccccccu cugcuucggc aaguucccca     120
ucuacaccau ccccgacaag cuggggccgu ggagccccau cgacaucccac caccugucccc    180 gccccaacaa ccucgugguc gaggacgagg gcugcaccaa ccugagcggg uucuccuaca     240
uggagcugaa ggugggcuac aucagcgcca ucaagaugaa cgggucacg ugcaccggcg      300 uggucaccga ggcggagacc uacacgaacu ucgugggcua cgugaccacc accuucaagc     360
ggaagcacuu ccgccccacg ccggacgccu gccgggccgc cuacaacugg aagauggccg     420 ggacccccg cuacgaggag ucccuccaca accccuaccc cgacuaccac uggcugcgga     480
ccgucaagac caccaaggag agccuggugg ucauccccc gagcguggcg gaccucgacc     540
```

-continued

```
ccuacgaccg cucccugcac agccgggucu uccccggcgg gaacugcucc ggcguggccg    600
ugagcuccac guacugcagc accaaccacg acuacaccau cuggaugccc gagaacccgc    660
gccuggggau guccugcgac aucuucacca acagccgggg caagcgcgcc uccaagggca    720
gcgagacgug cggguucguc gacgagcggg gccucuacaa gucccugaag gggggccugca    780 agcugaagcu cugcggcgug cugggccugc gccucaugga cgggaccugg guggcgaugc    840
agaccagcaa cgagaccaag uggugccccc ccggccagcu ggucaaccug cacgacuucc    900
ggagcgacga gaucgagcac cucguggugg aggagcuggu caagaagcgc gaggagugcc    960
uggacgcccu cgaguccauc augacgacca agagcguguc cuuccggcgc cugagccacc   1020
ugcggaagcu cgugcccggg uucggcaagg ccuacaccau cuucaacaag acccugaugg   1080
aggccgacgc ccacuacaag uccguccgca cguggaacga gaucaucccg agcaaggggu   1140
gccugcgggu gggcggccgc ugccaccccc acgucaacgg gguguucuuc aacggcauca   1200
uccucgggcc cgacggcaac gugcugaucc ccgagaugca guccagccug cuccagcagc   1260
acauggagcu gcuggucucc agcgugaucc cgcucaugca cccccuggcg gaccccucca   1320
ccguguucaa gaacggggac gaggccgagg acuucgucga ggugcaccug cccgacgugc   1380
acgagcggau cagcggcguc gaccucggcc ugccgaacug ggggaaguac gugcugcucu   1440
ccgccggcgc ccugaccgcc cugaugcuga ucaucuuccu caugaccugc uggcgccggg   1500
ugaaccggag cgagcccacg cagcacaacc ugcgcgggac cggccgggag gucuccguga   1560
ccccgcagag cgggaagauc aucuccagcu gggaguccua caagagcggc ggcgagaccg   1620
ggcugugagg acuagugcau cacauuuaaa agcaucucag ccuaccauga gaauaagaga   1680
aagaaaauga agaucaauag cuuauucauc ucuuuuucuu uuucguuggu guaaagccaa   1740
cacccugucu aaaaaacaua aauuucuuua aucauuuugc cucuuuucuc ugugcuucaa   1800
uuaauaaaaa auggaaagaa ccuagaucua aaaaaaaaaa aaaaaaaaaa aaaaaaaaaa   1860
aaaaaaaaaa aaaaaaaaaa aaaaaaaaaa aaaugcaucc cccccccccc cccccccccc   1920
ccccccccca aaggcucuuu ucagagccac cagaauu                            1957

<210> SEQ ID NO 26
<211> LENGTH: 75
<212> TYPE: DNA
<213> ORGANISM: Homo sapiens

<400> SEQUENCE: 26
gcggctcggc cattttgtcc cagtcagtcc ggaggctgcg gctgcagaag taccgcctgc     60
ggagtaactg caaag                                                      75

<210> SEQ ID NO 27
<211> LENGTH: 24
<212> TYPE: RNA
<213> ORGANISM: Artificial Sequence
<220> FEATURE:
<223> OTHER INFORMATION: histone stem-loop sequence

<400> SEQUENCE: 27
caaaggcucu uuucagagcc acca                                            24
```